(12) United States Patent
DiBenedetto et al.

(10) Patent No.: US 8,056,268 B2
(45) Date of Patent: *Nov. 15, 2011

(54) INTELLIGENT FOOTWEAR SYSTEMS

(75) Inventors: Christian DiBenedetto, North Plain, OR (US); Mark Arthur Oleson, Portland, OR (US)

(73) Assignee: adidas International Marketing B.V., Amsterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 12/614,969

(22) Filed: Nov. 9, 2009

(65) Prior Publication Data

US 2010/0050478 A1    Mar. 4, 2010

Related U.S. Application Data

(63) Continuation of application No. 11/387,752, filed on Mar. 23, 2006, now Pat. No. 7,631,382, which is a continuation-in-part of application No. 11/047,550, filed on Jan. 31, 2005, now Pat. No. 7,225,565, which is a continuation-in-part of application No. 10/385,300, filed on Mar. 10, 2003, now Pat. No. 7,188,439.

(60) Provisional application No. 60/557,902, filed on Mar. 30, 2004.

(51) Int. Cl.
*A43B 5/00* (2006.01)
*A43B 13/14* (2006.01)
*A43B 13/20* (2006.01)

(52) U.S. Cl. ............... 36/132; 36/93; 36/29; 36/25 R

(58) Field of Classification Search ............ 36/132, 36/93, 29, 28, 136, 30 R, 25 R; 600/592; 73/172

See application file for complete search history.

(56) References Cited

U.S. PATENT DOCUMENTS

| | | | |
|---|---|---|---|
| 4,703,445 A | 10/1987 | Dassler |
| 4,771,394 A | 9/1988 | Cavanagh |
| 4,814,661 A | 3/1989 | Ratzlaff et al. |
| 4,891,797 A | 1/1990 | Woodfalks |
| 5,179,792 A | 1/1993 | Brantingham |
| 5,269,081 A | 12/1993 | Gray |
| 5,325,869 A | 7/1994 | Stokes |
| 5,335,188 A | 8/1994 | Brisson |
| 5,357,696 A | 10/1994 | Gray et al. |
| 5,373,651 A | 12/1994 | Wood |

(Continued)

FOREIGN PATENT DOCUMENTS

DE    1 013 126    8/1957

(Continued)

OTHER PUBLICATIONS

European Search Report dated Dec. 27, 2010 in related Serial No. 10 17 9310.

(Continued)

*Primary Examiner* — Ted Kavanaugh
(74) *Attorney, Agent, or Firm* — Kilpatrick Townsend & Stockton

(57) ABSTRACT

The invention is directed to intelligent systems for articles of footwear that adjust automatically in response to a measured performance characteristic. The intelligent systems include one or more adjustable elements coupled to a mechanism that actuates the adjustable elements in response to a signal from a sensor to modify the performance characteristic of the article of footwear. The intelligent system adjusts the performance characteristics of the article of footwear without human intervention.

18 Claims, 56 Drawing Sheets

| Pin 19 | Pin 18 | Pin 17 | Electro-luminescent element(s) On |
|---|---|---|---|
| Z | 1 | 0 | D1 |
| 1 | Z | 0 | D2 |
| 1 | 0 | Z | D3 |
| Z | 0 | 1 | D4 |
| 0 | Z | 1 | D5 |
| 1 | 1 | 0 | D1, D2 |
| 1 | 0 | 0 | D2, D3 |
| 1 | 0 | 1 | D3, D4 |
| 0 | 0 | 1 | D4, D5 |

U.S. PATENT DOCUMENTS

| | | | |
|---|---|---|---|
| 5,383,290 A | | 1/1995 | Grim |
| 5,471,405 A | * | 11/1995 | Marsh .......................... 702/41 |
| 5,557,865 A | | 9/1996 | Sjosvard et al. |
| 5,566,479 A | | 10/1996 | Gray et al. |
| 5,596,652 A | | 1/1997 | Piatek et al. |
| 5,598,849 A | | 2/1997 | Browne et al. |
| 5,636,146 A | | 6/1997 | Flentov et al. |
| 5,720,200 A | | 2/1998 | Anderson et al. |
| 5,724,265 A | | 3/1998 | Hutchings |
| 5,724,667 A | | 3/1998 | Furuno et al. |
| 5,793,882 A | | 8/1998 | Piatek et al. |
| 5,794,361 A | | 8/1998 | Sadler et al. |
| 5,813,142 A | | 9/1998 | Demon |
| 5,815,954 A | | 10/1998 | Huang |
| 5,890,997 A | | 4/1999 | Roth |
| 5,918,502 A | | 7/1999 | Bishop |
| 5,929,332 A | | 7/1999 | Brown |
| 5,931,763 A | | 8/1999 | Alessandri et al. |
| 5,937,462 A | | 8/1999 | Huang et al. |
| 5,955,667 A | | 9/1999 | Fyfe et al. |
| 5,960,380 A | | 9/1999 | Flentov et al. |
| 6,013,007 A | | 1/2000 | Root et al. |
| 6,018,705 A | | 1/2000 | Gaudet et al. |
| 6,052,654 A | | 4/2000 | Gaudet et al. |
| 6,077,193 A | | 6/2000 | Buhler et al. |
| 6,122,340 A | | 9/2000 | Darley et al. |
| 6,160,254 A | | 12/2000 | Zimmerman et al. |
| 6,203,501 B1 | | 3/2001 | Bowman |
| 6,230,501 B1 | | 5/2001 | Bailey, Sr. et al. |
| 6,266,623 B1 | | 7/2001 | Vock et al. |
| 6,266,632 B1 | | 7/2001 | Kato et al. |
| 6,278,378 B1 | | 8/2001 | Feiner et al. |
| 6,298,314 B1 | | 10/2001 | Blackadar et al. |
| 6,336,365 B1 | | 1/2002 | Blackadar et al. |
| 6,357,147 B1 | | 3/2002 | Darley et al. |
| 6,375,612 B1 | | 4/2002 | Guichon et al. |
| 6,396,413 B2 | | 5/2002 | Hines et al. |
| 6,424,264 B1 | | 7/2002 | Giraldin et al. |
| 6,430,843 B1 | | 8/2002 | Potter et al. |
| 6,493,652 B1 | | 12/2002 | Ohlenbusch et al. |
| 6,496,787 B1 | | 12/2002 | Flentov et al. |
| 6,498,994 B2 | | 12/2002 | Vock et al. |
| 6,499,000 B2 | | 12/2002 | Flentov et al. |
| 6,516,284 B2 | | 2/2003 | Flentov et al. |
| 6,526,158 B1 | | 2/2003 | Goldberg |
| 6,531,963 B1 | | 3/2003 | Nyfelt et al. |
| 6,536,139 B2 | | 3/2003 | Darley et al. |
| 6,539,336 B1 | | 3/2003 | Vock et al. |
| 6,560,903 B1 | | 5/2003 | Darley |
| 6,569,092 B1 | | 5/2003 | Guichon et al. |
| 6,600,407 B2 | | 7/2003 | Paek et al. |
| 6,611,789 B1 | | 8/2003 | Darley |
| 6,614,392 B2 | | 9/2003 | Howard |
| 6,661,782 B1 | | 12/2003 | Mustajarvi et al. |
| 6,788,200 B1 | * | 9/2004 | Jamel et al. ............... 340/539.13 |
| 6,795,017 B1 | * | 9/2004 | Puranik et al. ............ 342/357.77 |
| 6,807,753 B2 | | 10/2004 | Steszyn et al. |
| 6,813,586 B1 | | 11/2004 | Vock et al. |
| 6,825,777 B2 | | 11/2004 | Vock et al. |
| 6,856,934 B2 | | 2/2005 | Vock et al. |
| 6,865,825 B2 | | 3/2005 | Bailey, Sr. et al. |
| 6,876,947 B1 | | 4/2005 | Darley et al. |
| 6,882,955 B1 | | 4/2005 | Ohlenbusch et al. |
| 6,885,971 B2 | | 4/2005 | Vock et al. |
| 6,898,550 B1 | | 5/2005 | Blackadar et al. |
| 6,959,259 B2 | | 10/2005 | Vock et al. |
| 6,963,818 B2 | | 11/2005 | Flentov et al. |
| 7,007,412 B2 | | 3/2006 | Munster |
| 7,072,789 B2 | | 7/2006 | Vock et al. |
| 7,092,846 B2 | | 8/2006 | Vock et al. |
| 7,107,706 B1 | | 9/2006 | Bailey, Sr. et al. |
| 7,158,912 B2 | | 1/2007 | Vock et al. |
| 7,162,392 B2 | | 1/2007 | Vock et al. |
| 7,171,331 B2 | | 1/2007 | Vock et al. |
| 7,188,439 B2 | | 3/2007 | DiBenedetto et al. |
| 7,200,517 B2 | | 4/2007 | Darley et al. |
| 7,204,041 B1 | | 4/2007 | Bailey, Sr. et al. |
| 7,219,449 B1 | | 5/2007 | Hoffberg et al. |
| 7,225,565 B2 | | 6/2007 | DiBenedetto et al. |
| 7,506,460 B2 | | 3/2009 | DiBenedetto et al. |
| 7,631,382 B2 | | 12/2009 | DiBenedetto et al. |
| 7,676,960 B2 | * | 3/2010 | DiBenedetto et al. .......... 36/132 |
| 7,676,961 B2 | | 3/2010 | DiBenedetto et al. |
| 2001/0054014 A1 | | 12/2001 | Noda et al. |
| 2002/0022551 A1 | | 2/2002 | Watterson et al. |
| 2002/0077883 A1 | | 6/2002 | Lancos et al. |
| 2002/0080198 A1 | | 6/2002 | Giraldin et al. |
| 2002/0091796 A1 | | 7/2002 | Higginson et al. |
| 2002/0142887 A1 | | 10/2002 | O'Malley |
| 2002/0147629 A1 | | 10/2002 | Alsafadi et al. |
| 2002/0147642 A1 | | 10/2002 | Avallone et al. |
| 2002/0152645 A1 | | 10/2002 | Darley et al. |
| 2002/0156677 A1 | | 10/2002 | Peters et al. |
| 2002/0165758 A1 | | 11/2002 | Hind et al. |
| 2002/0173407 A1 | | 11/2002 | Bowman |
| 2002/0174025 A1 | | 11/2002 | Hind et al. |
| 2003/0009308 A1 | | 1/2003 | Kirtley |
| 2003/0009382 A1 | | 1/2003 | D'Arbeloff et al. |
| 2003/0009913 A1 | | 1/2003 | Potter et al. |
| 2003/0040922 A1 | | 2/2003 | Bodin |
| 2003/0056401 A1 | | 3/2003 | Kwon |
| 2003/0090386 A1 | | 5/2003 | Giraldin et al. |
| 2003/0097878 A1 | | 5/2003 | Farringdon et al. |
| 2003/0120353 A1 | | 6/2003 | Christensen |
| 2003/0160732 A1 | | 8/2003 | Van Heerden et al. |
| 2003/0163287 A1 | | 8/2003 | Vock et al. |
| 2004/0064974 A1 | | 4/2004 | Schuster |
| 2004/0177531 A1 | | 9/2004 | DiBenedetto et al. |
| 2005/0080566 A1 | | 4/2005 | Vock et al. |
| 2005/0183292 A1 | | 8/2005 | DiBenedetto et al. |
| 2005/0184878 A1 | | 8/2005 | Grold et al. |
| 2006/0014645 A1 | | 1/2006 | Yavitz |
| 2006/0020421 A1 | | 1/2006 | Darley et al. |
| 2006/0031039 A1 | | 2/2006 | Flentov et al. |
| 2006/0052983 A1 | | 3/2006 | Vock et al. |
| 2006/0235642 A1 | | 10/2006 | Vock et al. |
| 2007/0000154 A1 | | 1/2007 | DiBenedetto et al. |
| 2007/0006489 A1 | | 1/2007 | Case et al. |
| 2007/0011920 A1 | | 1/2007 | DiBenedetto et al. |
| 2007/0024306 A1 | | 2/2007 | Jeddeloh et al. |
| 2007/0180736 A1 | | 8/2007 | DiBenedetto et al. |
| 2007/0180737 A1 | | 8/2007 | DiBenedetto et al. |
| 2007/0247306 A1 | | 10/2007 | Case |
| 2009/0265958 A1 | | 10/2009 | DiBenedetto et al. |
| 2009/0267783 A1 | | 10/2009 | Vock et al. |

FOREIGN PATENT DOCUMENTS

| | | |
|---|---|---|
| DE | 35 06 055 | 8/1986 |
| DE | 297 01 308 | 5/1997 |
| DE | 10201134 | 7/2003 |
| EP | 0472110 | 2/1992 |
| EP | 1457128 | 9/2004 |
| FR | 2 743 701 | 7/1997 |
| WO | WO-90-00866 | 2/1990 |
| WO | WO-94-05177 | 3/1994 |
| WO | WO-00-33031 | 6/2000 |
| WO | WO-01-80678 | 11/2001 |

OTHER PUBLICATIONS

European Search Report for Application No. EP 04 00 5660, mailed from the European Patent Office on Oct. 7, 2004 (6 pages).

* cited by examiner

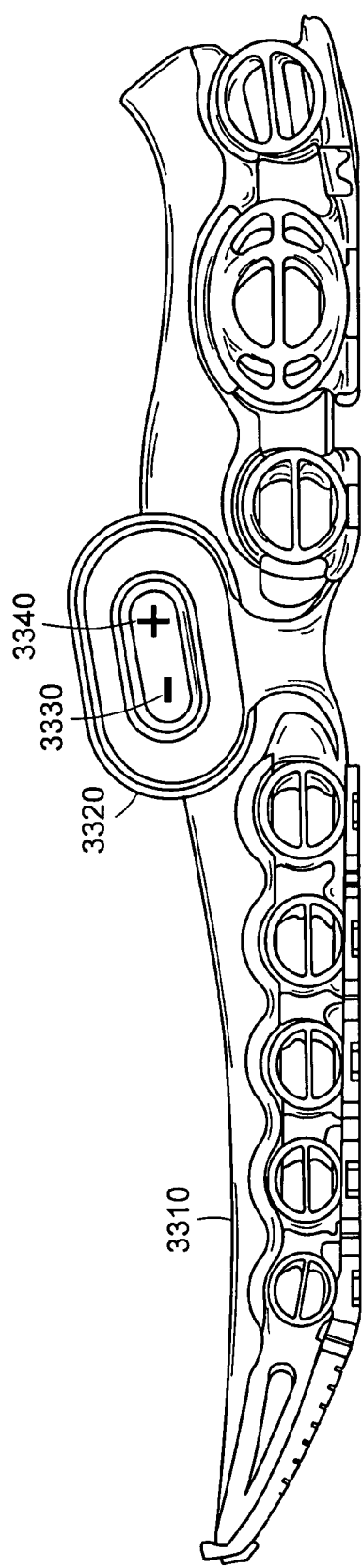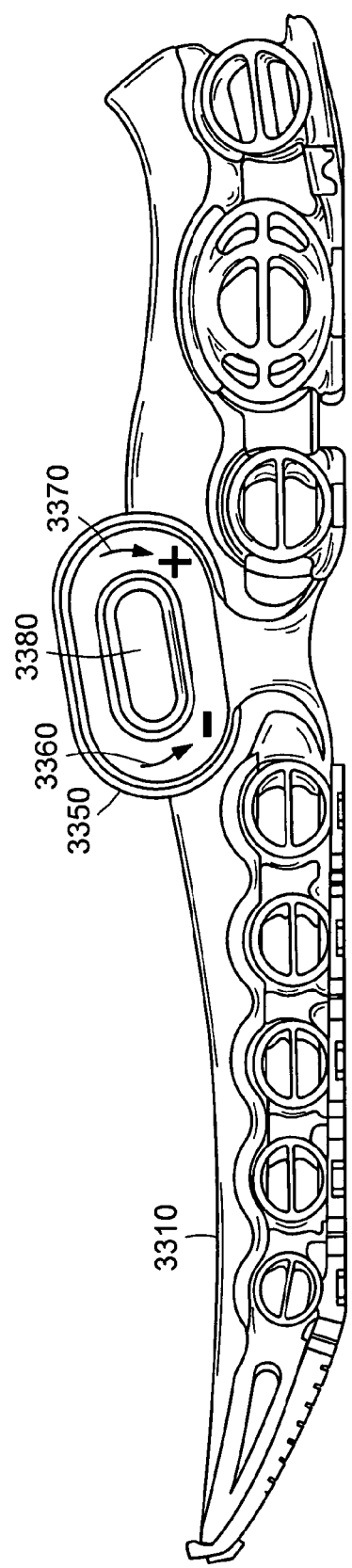

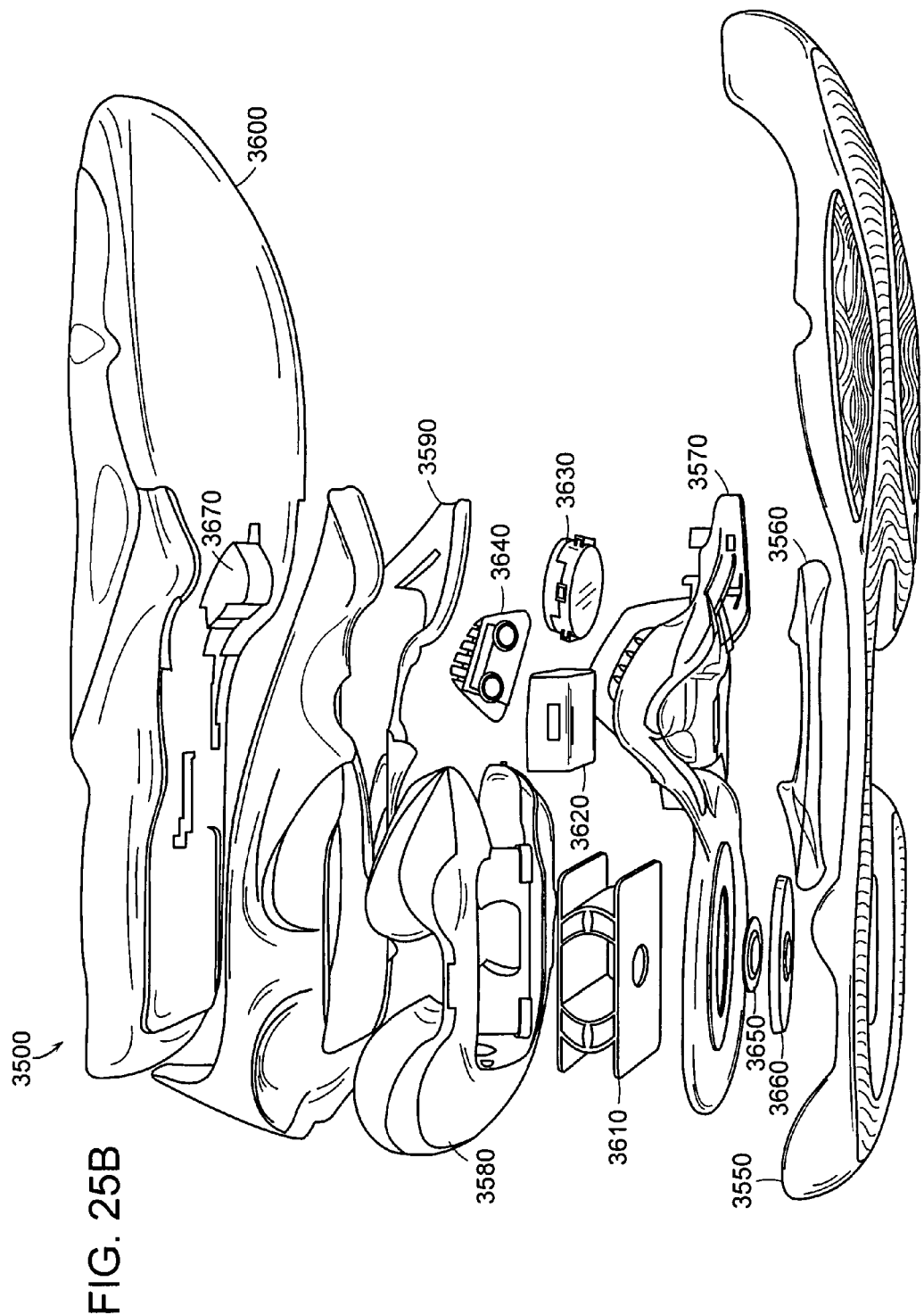

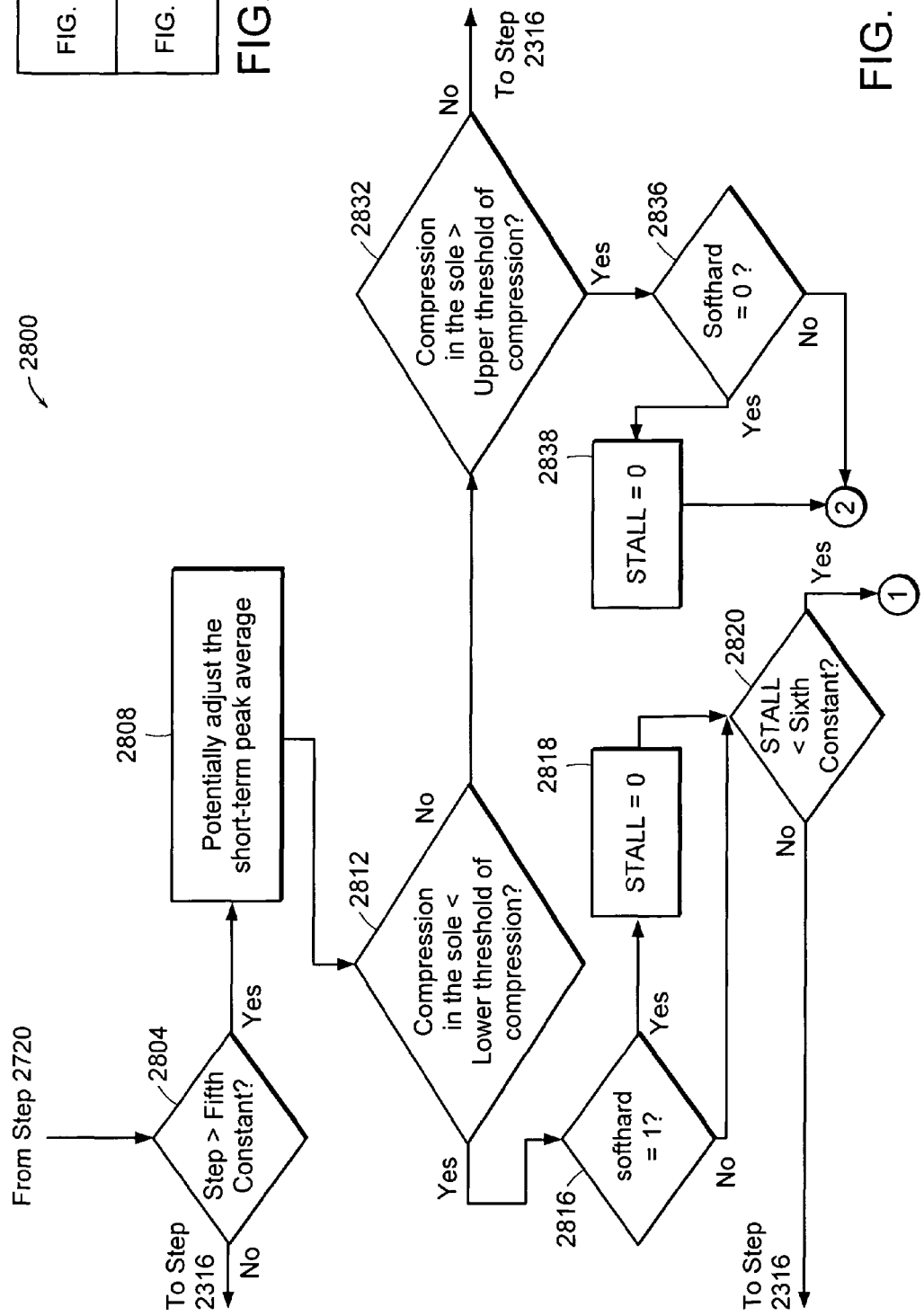

| Pin 19 | Pin 18 | Pin 17 | Electro-luminescent element(s) On |
|---|---|---|---|
| Z | 1 | 0 | D1 |
| 1 | Z | 0 | D2 |
| 1 | 0 | Z | D3 |
| Z | 0 | 1 | D4 |
| 0 | Z | 1 | D5 |
| 1 | 1 | 0 | D1, D2 |
| 1 | 0 | 0 | D2, D3 |
| 1 | 0 | 1 | D3, D4 |
| 0 | 0 | 1 | D4, D5 |

FIG. 37

| Motor Control Forward (Pin 12) | Motor Control Reverse (Pin 10) | Motor Drive Forward | Motor Drive Return |
|---|---|---|---|
| High | Low | Vbat | GND |
| Low | High | GND | Vbat |
| High | High | GND | GND |
| Low | Low | Vbat | Vbat |

FIG. 38

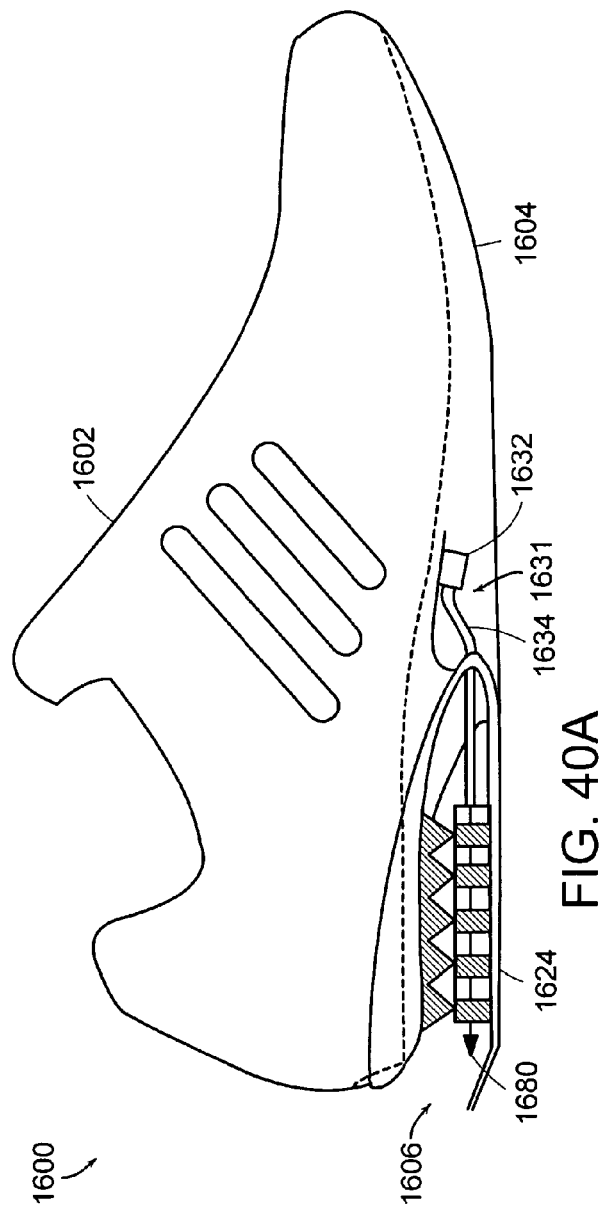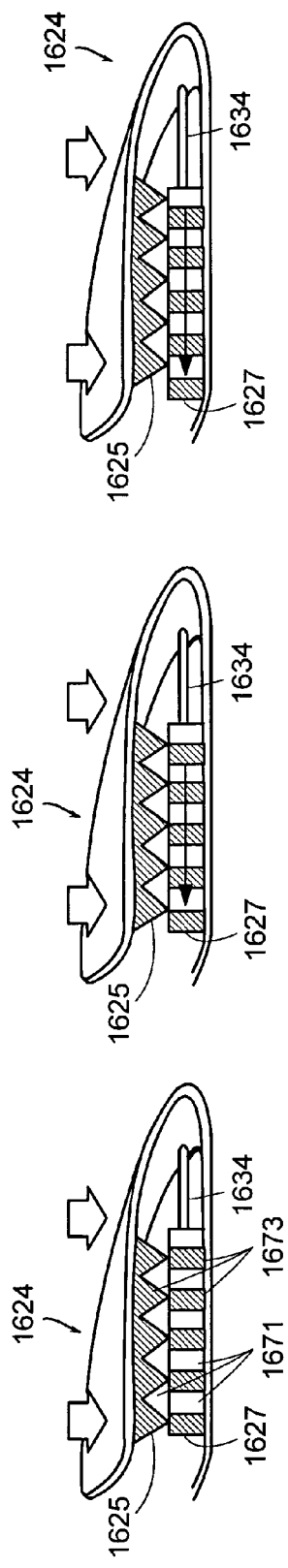

INTELLIGENT FOOTWEAR SYSTEMS

CROSS-REFERENCE TO RELATED APPLICATIONS

This application is a continuation of U.S. application Ser. No. 11/387,752, filed on Mar. 23, 2006, which is a continuation-in-part of U.S. patent application Ser. No. 11/047,550, filed on Jan. 31, 2005, now U.S. Pat. No. 7,225,565, which is a continuation-in-part of U.S. patent application Ser. No. 10/385,300, filed on Mar. 10, 2003, now U.S. Pat. No. 7,188,439, the entire disclosures of which are hereby incorporated herein by reference. This application also claims priority to U.S. Provisional Patent Application Ser. No. 60/557,902, filed on Mar. 30, 2004, the disclosure of which is hereby incorporated herein by reference in its entirety.

TECHNICAL FIELD

The invention generally relates to intelligent systems for articles of footwear. In particular, the invention relates to automatic, self-adjusting systems that modify a performance characteristic of the article of footwear.

BACKGROUND INFORMATION

Conventional athletic shoes include an upper and a sole. The material of the sole is usually chosen with a view towards optimizing a particular performance characteristic of the shoe, for example, stability or stiffness. Typically, the sole includes a midsole and an outsole, either of which can include a resilient material to protect a wearer's foot and leg. One drawback with conventional shoes is that performance characteristics, such as cushioning and stiffness, are not adjustable. The wearer must, therefore, select a specific shoe for a specific activity. For example, for activities requiring greater cushioning, such as running, the wearer must select one type of shoe and for activities requiring greater stiffness for support during lateral movement, such as basketball, the wearer must select a different type of shoe.

Some shoes have been designed to allow for adjustment in the degree of cushioning or stiffness provided by the sole. Many of these shoes employ a fluid bladder that can be inflated or deflated as desired. A disadvantage presented by these shoes is that one or more of the bladders can fail, rendering the cushioning system effectively useless. Moreover, many of the shoes employing fluid bladders do not allow for small-scale changes to the degree of cushioning provided by the sole. Often, the change to the degree of cushioning provided by the sole in pressurizing or depressurizing, or in partially pressurizing or partially depressurizing, a bladder will be larger than that desired by the wearer. In other words, bladders are typically not capable of fine adjustments.

A further disadvantage of many of the shoes designed to allow for adjustment in the degree of cushioning or stiffness provided by the sole is that they are only manually adjustable. Accordingly, in order to adjust such shoes the wearer is required to interrupt the specific activity in which he/she is engaged. With some shoes, the wearer may also be required to partially disassemble the shoe, re-assemble the shoe, and even exchange shoe parts. Moreover, the wearer, to his or her dissatisfaction, may be limited in the amount of adjustment that can be made.

Some shoes have been designed to automatically adjust the degree of cushioning or stiffness provided by the sole. These shoes measure the amount of force or pressure exerted on the sole by the wearer's foot when the wearer's foot strikes the ground. Through analysis and investigation, it has been discovered that the mere measurement of force or pressure alone, however, is too limited, as it provides no information relating to the performance of the shoe. For example, measuring force provides no indication as to whether the sole has either over-compressed or under-compressed for that particular wearer without prior investigation into the normal forces exerted by the wearer during the activity. If the sole is either over-compressed or under-compressed, the shoe is poorly matched to the wearer's activity and needs. In essence, the wearer's body has to adapt to the shoe. The biomechanical needs of the wearer are poorly met, if at all.

In sum, shoes that have been designed to allow for some adjustment in the degree of cushioning or stiffness provided by the sole still fall short of accommodating the wearer's needs. Specifically, they are not fully adjustable throughout the range of the biomechanical needs of the particular wearer or lack the ability to sense the true needs of the wearer. As a result, the wearer must still, in some way, adapt his or her body to the environment presented by the shoe.

There is, therefore, a need for a shoe that senses the biomechanical needs of the wearer, automatically adjusts a performance characteristic of the shoe to accommodate the biomechanical needs of the wearer, for example the degree of cushioning or stiffness provided by the sole, and avoids the drawbacks of bladder cushioning or manually adjustable shoes.

SUMMARY OF THE INVENTION

The invention is directed to intelligent systems for articles of footwear that adjust a feature of the footwear in response to the footwear's environment, without human interaction. In other words, the footwear is adaptive. For example, the intelligent system can continuously sense the biomechanical needs of the wearer and concomitantly modify the footwear to an optimal configuration. The intelligent system includes a sensing system, a control system, and an actuation system. Further, the intelligent system can sense the conditions of use of the article of footwear, understand under what condition the article of footwear is being used, and adapt the article of footwear accordingly.

The sensing system measures a performance characteristic of the article of footwear and sends a signal to the control system. The signal is representative of the measured performance characteristic. The control system processes the signal to determine if, for example, the performance characteristic deviates from an acceptable range or exceeds a predetermined threshold. The control system sends a signal to the actuation system relative to the deviation. The actuation system modifies a feature of the footwear in order to obtain an optimal performance characteristic.

In one aspect, the invention relates to an intelligent system for an article of footwear. The system includes a control system, a power source electrically coupled to the control system, an adjustable element, and a driver coupled to the adjustable element. The driver adjusts the adjustable element in response to a signal from the control system.

In another aspect, the invention relates to an article of footwear including an upper coupled to a sole and an intelligent system at least partially disposed in the sole. The system includes a control system, a power source electrically coupled to the control system, an adjustable element, and a driver coupled to the adjustable element. The driver adjusts the adjustable element in response to a signal from the control system.

In various embodiments of the foregoing aspects, the system modifies a performance characteristic of the article of footwear, such as compressibility, resiliency, compliancy, elasticity, damping, energy storage, cushioning, stability, comfort, velocity, acceleration, jerk, stiffness, or combinations thereof. In one embodiment, the adjustable element is adjusted by at least one of translation, rotation, reorientation, modification of a range of motion, or combinations thereof. The system may include a limiter for limiting a range of motion of the adjustable element. The control system includes a sensor and electrical circuitry. The sensor may be a pressure sensor, a force transducer, a hall effect sensor, a strain gauge, a piezoelectric element, a load cell, a proximity sensor, an optical sensor, an accelerometer, a hall element or sensor, a capacitance sensor, an inductance sensor, an ultrasonic transducer and receiver, a radio frequency emitter and receiver, a magneto-resistive element, or a giant magneto-resistive element. In various embodiments, the driver may be a worm drive, a lead screw, a rotary actuator, a linear actuator, a gear train, a linkage, a cable driving system, a latching mechanism, a piezo material based system, a shape memory material based system, a system using a magnetorheological fluid, a system using an inflatable bladder(s), or combinations thereof.

In still other embodiments, the adjustable element may be at least partially disposed in at least one of a forefoot portion, a midfoot portion, and a rearfoot portion of the article of footwear. In one embodiment, the article of footwear has a sole including an outsole and a midsole and the adjustable element is disposed at least partially in the midsole. In various embodiments, the adjustable element may be generally longitudinally disposed within the article of footwear, or the adjustable element may be generally laterally disposed within the article of footwear, or both. For example, the adjustable element may extend from a heel region to an arch region of the article of footwear or from an arch region to a forefoot region of the article of footwear or from a forefoot region to a heel region of the article of footwear. Furthermore, the adjustable element may be at least partially disposed in a lateral side, or a medial side, or both of the article of footwear.

In another aspect, the invention relates to a method of modifying a performance characteristic of an article of footwear during use. The method includes the steps of monitoring the performance characteristic of the article of footwear, generating a corrective driver signal, and adjusting an adjustable element based on the driver signal to modify the performance characteristic of the article of footwear. In one embodiment, the steps are repeated until a threshold value of the performance characteristic is obtained.

In various embodiments of the foregoing aspect, the generating step includes the substeps of comparing the monitored performance characteristic to a desired performance characteristic to generate a deviation and outputting a corrective driver signal magnitude based on the deviation. In one embodiment, the corrective driver signal has a predetermined magnitude. Further, the monitoring step may include the substeps of measuring a magnetic field of a magnet with a proximity sensor, wherein at least one of the magnet and the sensor are at least partially disposed within the sole and are vertically spaced apart in an unloaded state, and comparing the magnetic field measurement during compression to a threshold value. In one embodiment, the monitoring step involves taking multiple measurements of the magnetic field during compression and comparing an average magnetic field measurement to the threshold value.

In additional embodiments, the method may include the step of limiting a range of motion of the adjustable element with a limiter and the adjusting step may include adjusting the limiter a predetermined distance. The adjustment step may be performed when the article of footwear is in an unloaded state. In one embodiment, the adjustment step is terminated when a threshold value of the performance characteristic is reached.

In various embodiments of all of the foregoing aspects of the invention, the adjustable element may be an expansion element, a multiple density foam, a skeletal element, a multidensity plate, or combinations thereof. The adjustable element may exhibit an anisotropic property. In one embodiment, the adjustable element may be a generally elliptically-shaped expansion element. Further, the system may include a manual adjustment for altering or biasing the performance characteristic of the adjustable element, or an indicator, or both. The manual adjustment may also alter a threshold value of the performance characteristic. The indicator may be audible, visual, or both. For example, the indicator may be a series of electro-luminescent elements.

In another aspect, the invention relates to a system for measuring compression within an article of footwear. The system includes a sensor at least partially disposed within a sole of the article of footwear and a magnet generally aligned with and spaced from the sensor. The sensor may be a hall effect sensor, a proximity sensor, a hall element or sensor, a capacitance sensor, an inductance sensor, an ultrasonic transducer and receiver, a radio frequency emitter and receiver, a magneto-resistive element, or a giant magneto-resistive element. The system may include a processor. In one embodiment, the sensor measures a magnetic field generated by the magnet and the processor converts the magnetic field measurement into a distance measurement representing an amount of compression of the sole in correlation with respective time measurements. The processor may convert the distance measurements into a jerk value, a value representing acceleration, a value representing optimal compression, and/or a value representing a compression force.

In various embodiments of the foregoing aspect, the system further includes a driver coupled to the sensor and an adjustable element coupled to the driver. The system may include a limiter for limiting a range of motion of the adjustable element. In one embodiment, a performance characteristic of the article of footwear is modified in response to a signal from the sensor. In one embodiment, the signal corresponds to an amount of compression of the sole.

In another aspect, the invention relates to a method of providing comfort in an article of footwear. The method includes the steps of providing an adjustable article of footwear and determining a jerk value, a value representing acceleration, a value representing optimal compression, and/or a value representing a compression force. The method may further include the step of modifying a performance characteristic of the adjustable article of footwear based on the jerk value, the value representing acceleration, the value representing optimal compression, or the value representing a compression force.

In another aspect, the invention relates to a method for modifying a performance characteristic of an article of footwear during use. The method includes the steps of measuring a sensor signal from a sensor at least partially disposed within a sole of the article of footwear, and determining whether the sole has compressed. The method also includes, upon determining that the sole has compressed, the step of determining whether adjustment of the sole is required, and, upon determining that adjustment of the sole is required, the step of adjusting the sole.

In various embodiments of the foregoing aspect, the method further includes the steps of receiving a user input related to adjustment of the sole from a user of the article of footwear, adjusting a hardness setting for the sole in response to receiving the user input, and displaying the hardness setting for the sole by activating at least one electro-luminescent element, such as a light-emitting diode (LED) or an organic light emitting diode (OLED), disposed on the article of footwear. The method may also include the step of calculating at least one threshold of compression in response to receiving the user input. The at least one threshold of compression, which may be a lower threshold of compression and/or an upper threshold of compression, may be for use in determining whether adjustment of the sole is required.

In one embodiment, the step of measuring the sensor signal includes sampling the sensor signal a plurality of times. The step of measuring the sensor signal may also include calculating an average value for the sensor signal by averaging a subset of the plurality of samples of the sensor signal.

In another embodiment, the step of measuring the sensor signal is repeated at least once to obtain a plurality of measurements of the sensor signal. In one such embodiment, the step of determining whether the sole has compressed includes calculating a difference between an average of a plurality of previously obtained measurements of the sensor signal and the most recently obtained measurement of the sensor signal. The step of determining whether the sole has compressed may also include calculating this difference each time a new measurement of the sensor signal is obtained and/or determining whether a predetermined number of those calculated differences is greater than a predetermined constant.

In yet another embodiment, the step of measuring the sensor signal includes measuring compression in the sole. In one such embodiment, the step of determining whether adjustment of the sole is required includes determining the maximum amount of measured compression in the sole.

In still another embodiment, the step of determining whether adjustment of the sole is required includes determining whether there is a change in a surface condition on which the article of footwear is used. In one embodiment, the step of determining whether there is a change in the surface condition on which the article of footwear is used includes determining whether there is a change in a first parameter over time and substantially no change in a second parameter over time. In other embodiments, the step of determining whether there is a change in the surface condition on which the article of footwear is used includes determining whether there is a change in an absolute compression in the sole over time and substantially no change in a deviation of the compression in the sole over time, or alternatively, determining whether there is a change in the deviation of the compression in the sole over time and substantially no change in the absolute compression in the sole over time.

The surface condition on which the article of footwear is used may be determined to have changed from a hard ground surface to a soft ground surface. Alternatively, the surface condition may be determined to have changed from a soft ground surface to a hard ground surface. In one embodiment, the determination of whether there is a change in the surface condition on which the article of footwear is used is made after a wearer of the article of footwear has taken a plurality of steps.

In a further embodiment, the step of determining whether adjustment of the sole is required includes determining that the compression in the sole is less than a lower threshold of compression. In such a case, the step of adjusting the sole includes softening the sole. Alternatively, in another embodiment, the step of determining whether adjustment of the sole is required includes determining that the compression in the sole is greater than an upper threshold of compression. In this latter case, the step of adjusting the sole includes hardening the sole. In one embodiment, the adjustment of the sole is made after a wearer of the article of footwear has taken a plurality of steps.

Additionally, the step of adjusting the sole may include actuating a motor located within the sole. In one such embodiment, the method further includes the step of determining the status of the motor located within the sole. Determining the status of the motor may include sampling a battery voltage or using a potentiometer, an encoder, or any other suitable type of measuring device.

In another aspect, the invention relates to a controller for modifying a performance characteristic of an article of footwear during use. The controller includes a receiver configured to receive a first signal representing an output from a sensor at least partially disposed within a sole of the article of footwear, a determination module configured to determine whether the sole has compressed and to determine whether adjustment of the sole is required, and a transmitter configured to transmit a second signal for adjusting the sole.

In another aspect, the invention relates to an article of footwear that includes an upper coupled to a sole and a controller at least partially disposed within the sole. The controller includes means for receiving a first signal representing an output from a sensor at least partially disposed within the sole, means for determining whether the sole has compressed and for determining whether adjustment of the sole is required, and means for transmitting a second signal for adjusting the sole.

In another aspect, the invention relates to a method for modifying a performance characteristic of an article of footwear during use. The method includes the steps of measuring a sensor signal from a sensor at least partially disposed within a sole of the article of footwear, determining whether the article of footwear has experienced a peak condition, if so, determining whether adjustment of the article of footwear is required, and, if so, adjusting a performance characteristic of the article of footwear.

In various embodiments of the method, the peak condition is based on a change in state of the article of footwear as a result of an activity resulting in a compression criterion, such as a jump, a landing, a sprint, a turn, a cut, a push-off, and a stop. In some embodiments, the activity may cause an irregular profile. The change in state of the article can be represented by at least one of absolute compression, rate of compression, frequency of compression, change in rate of compression, uneven compression, velocity, acceleration, jerk, and combinations thereof. For example, if a wearer of an article of footwear embodying the invention experiences excessive pronation, the system senses uneven compression across the sole and can stiffen the sole, or portions thereof, as necessary to compensate therefor. Additionally, changes in the rate of compression may indicate that the wearer is changing pace from walking to sprinting, thereby warranting changing a performance characteristic of the shoe to compensate therefor. The method can further include the step of adjusting a threshold value for determining the peak condition. The method can include the step of evaluating when the peak condition is over and returning the threshold value to its previous setting. Various embodiments of the method can also include tracking a plurality of peak conditions experienced by the article of footwear and determining a new threshold value for determining whether the article of footwear has experienced a peak condition based on the plurality of peak conditions experienced. For example, the threshold setting for a particular user may be too low for the particular activity engaged, which can be determined by the system analyzing the plurality of peak conditions. The system can then adjust the threshold value or performance characteristic as necessary.

The method can further include the steps of monitoring a state of the article of footwear, determining if the article is inactive and, if so, enabling a sleep mode in the intelligent system. The step of monitoring the state of the article of footwear can include sampling the sensor signal at set intervals and, in one embodiment, determining whether the sensor signal has remained substantially constant for a set time period. The step of enabling a sleep mode in the intelligent system can include reducing power to at least one portion of the intelligent system. The intelligent system can be reactivated upon an indication of use of the article of footwear, such as a vibration, a force, acceleration, velocity, and an increase in temperature within the shoe or a change in electric or other field strength within the shoe (such as a change in capacitance). In addition, the method can include the steps of receiving a user input related to an adjustment of the performance characteristic through a user interface and adjusting an adjustable element at least partially disposed within the article of footwear in response to the user input. In one embodiment, the user interface can be a capacitive user interface, a button, a switch, a slider, a dial, or combinations thereof. The method can include providing an indication of a setting of the performance characteristic through an indicator, for example at least one electro-luminescent element disposed on the article of footwear.

In another aspect, the invention relates to an intelligent system for adjusting a performance characteristic of an article of footwear. The system includes a control system, a power source electrically coupled to the control system, an adjustable element, a driver coupled to the adjustable element for adjusting the adjustable element in response to a signal from the control system, and at least one user interface. The user interface can be a capacitive user interface, a button, a switch, a slider, a dial, or combinations thereof. A setting of the performance characteristic can be adjusted based on an input through the user interface.

In various embodiments, the driver includes a motor shaft and a sensor for determining an angular position or rotation counts of the motor shaft or number of shaft rotations. The sensor can be a magnetic sensor, any field sensor, a mechanical sensor, an optical sensor, or combinations thereof. The control system, power source, adjustable element, and driver can be arranged in a substantially horizontal orientation within a sole of the article of footwear. Such an arrangement can be used to reduce the overall height of the sole of the article of footwear.

In one embodiment, at least one of the control system, power source, adjustable element, and driver can be housed in a waterproof casing. In this embodiment, the waterproof casing can enable the intelligent system to perform when subjected to high levels of moisture. An assembly of the control system, the power source, the adjustable element, and the driver can also include a plurality of gaskets to render the assembly waterproof.

These and other objects, along with advantages and features of the present invention herein disclosed, will become apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 23A is a schematic side view of a sole and user input for an article of footwear including an intelligent system, in accordance with one embodiment of the invention;

FIG. 23B is a schematic side view of the sole of FIG. 23A with an alternative user input;

FIG. 25B is an exploded schematic perspective view of the sole of FIG. 25A;

FIG. 37 is a table that lists the states of the input/output at certain pins of the microcontroller of FIG. 35 that are required to turn on several combinations of the electro-luminescent elements of FIG. 35;

FIG. 38 is a table that lists the output that is required at certain pins of the microcontroller of FIG. 35 to drive the motor of the intelligent system;

FIG. 40A is a schematic side view of an article of footwear including yet another alternative embodiment of an intelligent system in accordance with the invention;

FIGS. 40B-40D are schematic side views of the intelligent system of FIG. 40A in various orientations;

DETAILED DESCRIPTION

Embodiments of the present invention are described below. It is, however, expressly noted that the present invention is not limited to these embodiments, but rather the intention is that modifications that are apparent to the person skilled in the art are also included. In particular, the present invention is not intended to be limited to any particular performance characteristic or sensor type or arrangement. Further, only a left or right shoe is depicted in any given figure; however, it is to be understood that the left and right shoes are typically mirror images of each other and the description applies to both left and right shoes. In certain activities that require different left and right shoe configurations or performance characteristics, the shoes need not be mirror images of each other.

Figure 1:
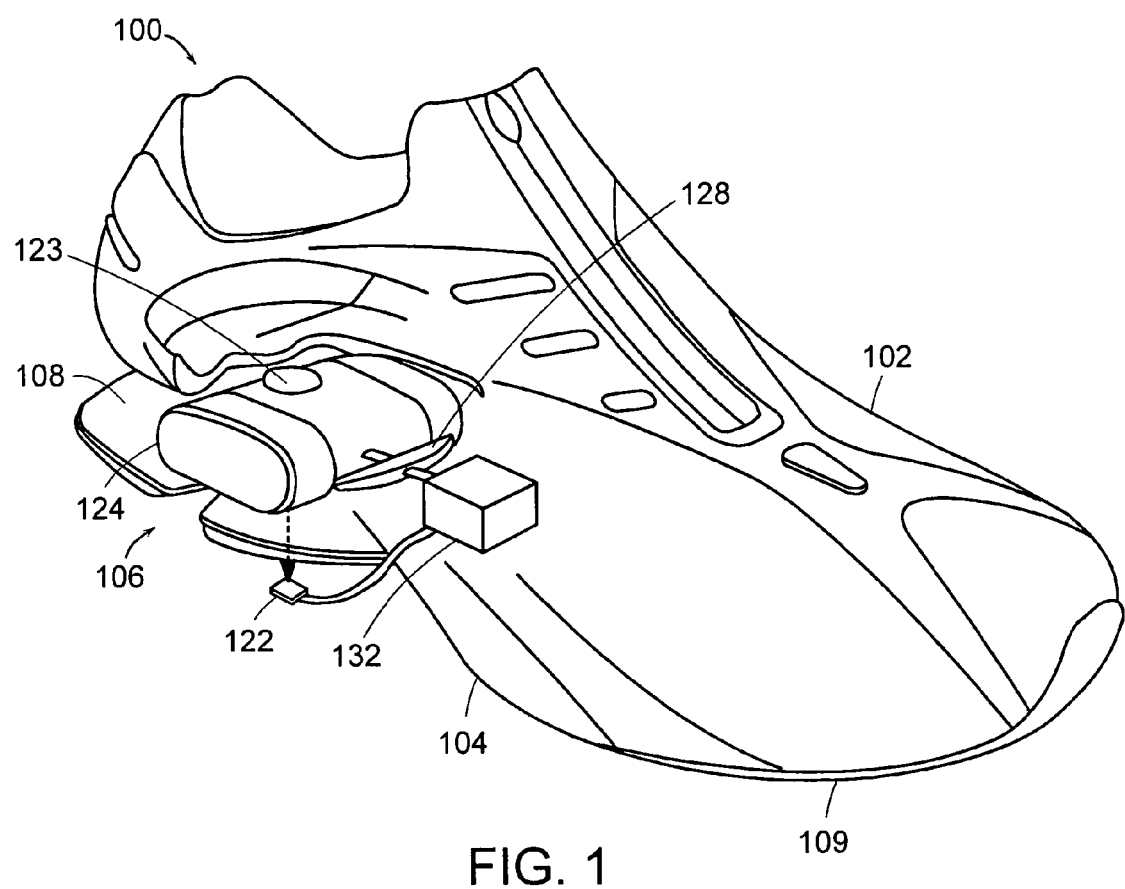
FIG. 1 is a partially exploded schematic perspective view of an article of footwear including an intelligent system in accordance with one embodiment of the invention.

FIG. 1 depicts an article of footwear 100 including an upper 102, a sole 104, and an intelligent system 106. The intelligent system 106 is laterally disposed in a rearfoot portion 108 of the article of footwear 100. The intelligent system 106 could be disposed anywhere along the length of the sole 104 and in essentially any orientation. In one embodiment, the intelligent system 106 is used to modify the compressibility of a heel area of the article of footwear 100. In another embodiment, the intelligent system 106 can be located in a forefoot portion 109 and can be moved into and out of alignment with a flex line or otherwise configured to vary a push-off characteristic of the footwear 100. In yet another embodiment, the footwear 100 could include multiple intelligent systems 106 disposed in multiple areas of the footwear 100. The intelligent system 106 is a self-adjusting system that modifies one or more performance characteristics of the article of footwear 100. The operation of the intelligent system 106 is described in detail hereinbelow.

Figure 2A:
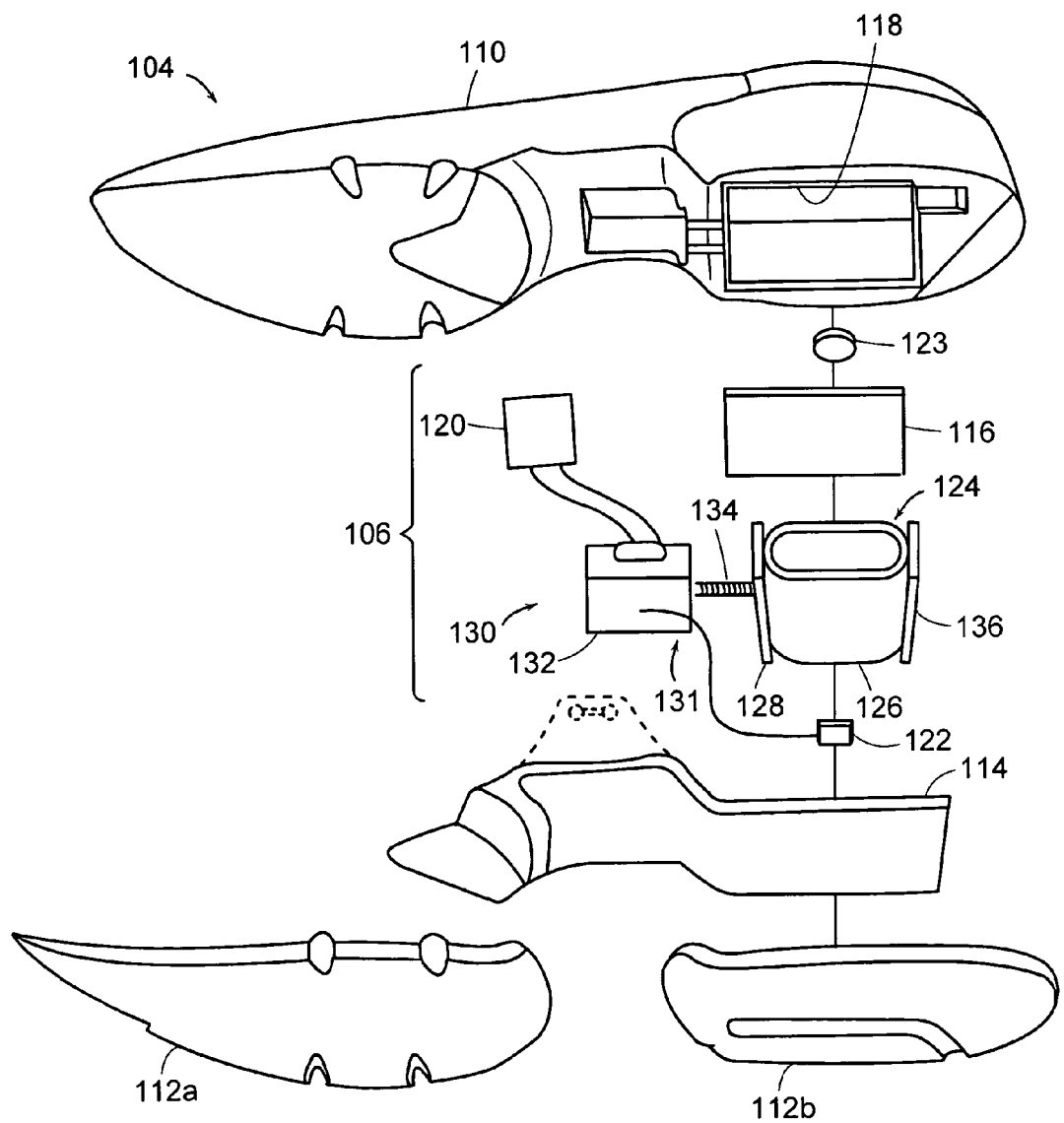
FIG. 2A is an exploded schematic perspective view of a sole of the article of footwear of FIG. 1 in accordance with one embodiment of the invention.

FIG. 2A depicts an exploded view of a portion of the sole 104 of FIG. 1. The sole 104 includes a midsole 110, an outsole 112a, 112b, an optional lower support plate 114, an optional upper support plate 116, and the intelligent system 106. The upper and lower support plates may, among other purposes, be included to help constrain the intelligent system 106 in a particular orientation. The intelligent system 106 is disposed within a cavity 118 formed in the midsole 110. In one embodiment, the midsole 110 is a modified conventional midsole and has a thickness of about 10 mm to about 30 mm, preferably about 20 mm in the heel portion. The intelligent system 106 includes a control system 120 and an actuation system 130 in electrical communication therewith, both of which are described in greater detail hereinbelow. The actuation system 130 includes a driver 131 and an adjustable element 124. The control system 120 includes a sensor 122, for example a proximity sensor, a magnet 123, and electrical circuitry (see FIGS. 29-30). In the embodiment shown, the sensor 122 is disposed below the adjustable element 124 and the magnet 123 is vertically spaced from the sensor 122. In this particular embodiment, the magnet 123 is disposed above the adjustable element 124 and is a Neodymium Iron Bore type magnet. The actual position and spacing of the sensor 122 and magnet 123 will vary to suit a particular application, for example, measuring and modifying the compressibility of the sole. In this particular embodiment, the sensor 122 and magnet 123 are located in a spot that corresponds generally to where maximum compression occurs in the rearfoot portion 108 of the footwear 100. Typically, the spot is under the wearer's calcaneous. In such an embodiment, the sensor 122 and magnet 123 are generally centered between a lateral side and a medial side of the sole 104 and are between about 25 mm and about 45 mm forward of a posterior aspect of the wearer's foot.

Figure 2B:
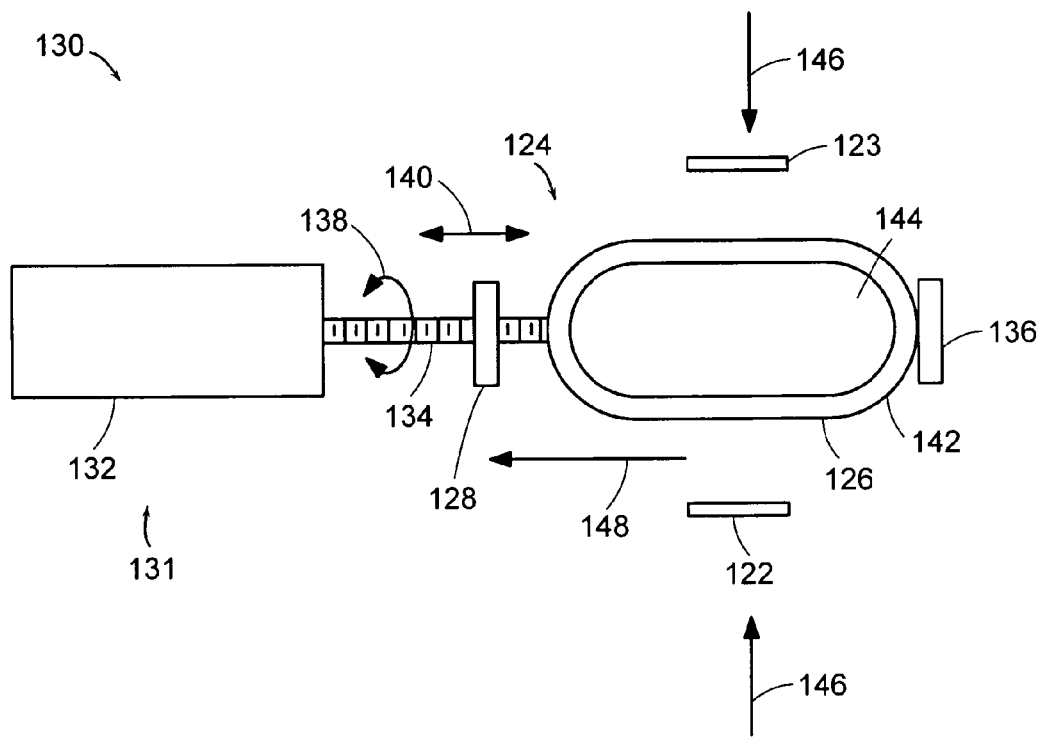
FIG. 2B is an enlarged schematic side view of the intelligent system of FIG. 2A illustrating the operation of the adjustable element.

FIG. 2B depicts a portion of the intelligent system 106, in particular the actuation system 130, in greater detail. The intelligent system 106 is preferably encased in a sealed, waterproof enclosure. The actuation system 130 generally includes a driver 131, which includes a motor 132 and a transmission element 134, and an adjustable element 124, which includes a limiter 128, an expansion element 126, and a stop 136. The embodiment of the particular driver 131 shown is a lead screw drive, made up of a bi-directional electric motor 132 and a threaded rod that forms the transmission element 134. In one embodiment, the motor 132 can be a radio-controlled servomotor of the type used in model airplanes. The threaded rod could be made of steel, stainless steel, or other suitable material.

The motor 132 is mechanically coupled to the transmission element 134 and drives the element 134 in either a clockwise or counter-clockwise direction as indicated by arrow 138. The transmission element 134 threadedly engages the limiter 128 and transversely positions the limiter 128 relative to the expansion element 126, as shown generally by arrow 140. Because the limiter 128 is threadedly engaged with the transmission element 134 and prevented from rotation relative to the motor 132 and the footwear 100, no power is required to maintain the limiter's position. There is sufficient friction in the actuation system 130 and a sufficiently fine thread on the transmission element 134 to prevent inadvertent rotation of the element 134 during a heel strike. In one example, the limiter 128 advances toward the expansion element 126 (forward) when the motor 132 drives the transmission element 134 in the clockwise direction and the limiter 128 moves away from the expansion element 126 (backward) when the motor 132 drives the transmission element 134 in the counter-clockwise direction. Alternatively, other types of drivers are possible. For example, the driver 131 could be essentially any type of rotary or linear actuator, a gear train, a linkage, or combinations thereof.

The expansion element 126 is generally cylindrical, with an elongated circular or elongated generally elliptically-shaped cross-section, or it includes a series of arched walls with different centers, but identical radii, or any combination thereof. The arcuate ends of the expansion elements are not necessarily semi-circular in shape. The radius of the arcuate ends will vary to suit a particular application and can be varied to control the amount of longitudinal expansion of the expansion element 126 when under compressive loading vertically. In general, the larger the radius of the arcuate end, the greater longitudinal expansion is possible under vertical compression loading. The expansion element 126 has a solid outer wall 142 and a optional compressible core 144 of foam or other resilient material. The size, shape, and materials used in the expansion element 126 will be selected to suit a particular application. In the embodiment shown, the transmission element 134 extends through the expansion element 126 and connects to a stop 136. The stop 136 prevents movement of the expansion element 126 in a direction away from the limiter 128. Alternatively, the stop 136 could be a rear wall of the cavity 118.

The general operation of the adjustable element 124 is described with respect to an application where the intelligent system 106 is used to modify cushioning in the article of footwear 100 in response to a measured parameter, for example compression of the midsole 110. The expansion element 126 is allowed to compress when acted on by a vertical force, depicted generally by arrows 146. The expansion element 126 expands in the horizontal direction (arrow 148) when compressed. The limiter 128 is used to control this movement. As the horizontal movement is limited, the vertical movement is limited as well. The expansion element 126 has a bi-modal compression response, which is discussed in greater detail below with respect to FIG. 42.

The intelligent system 106 can control the amount of compression a user creates in the article of footwear 100. As an example, when a user wearing the article of footwear 100 engages a ground surface during a stride, the vertical force 146 is applied to the expansion element 126 via the sole 104. The force 146 causes the expansion element 126 to expand during ground contact until it contacts the limiter 128, thereby controlling the compression of the sole 104.

During compression, the sensing portion of the control system 120 measures field strength of the magnet 123. In the embodiment shown, the sensor 122 is disposed proximate the bottom of the midsole 110 and the magnet 123 is disposed proximate the top of the midsole 110. The magnetic field strength detected by the sensor 122 changes as the magnet 123 moves closer to the sensor 122, as the midsole 110 is compressed. The system can be calibrated, such that this magnetic field strength can be converted to a distance. It is the change in distance that indicates how much the midsole 110 has been compressed. The control system 120 outputs a signal to the actuation system 130 based on the change in distance or compression measurement.

The actuation system 130 then modifies the hardness or compressibility of the midsole 110 based on the signal received from the control system 120. The actuation system 130 utilizes the transmission element 134 as the main moving component. The operation of the intelligent system 106 is described in greater detail below, with respect to the algorithms depicted in FIGS. 22-28.

Figure 3:
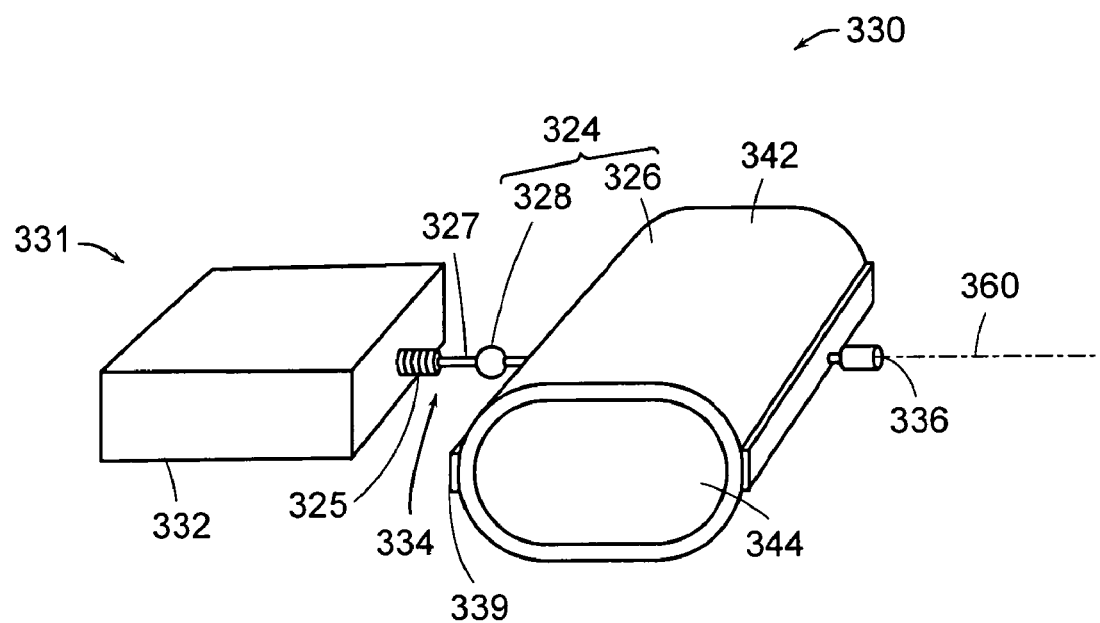
FIG. 3 is a schematic perspective view of an alternative embodiment of an adjustable element in accordance with the invention.

FIG. 3 depicts a portion of an alternative embodiment of an intelligent system 306 in accordance with the invention, in particular the actuation system 330. The actuation system 330 includes a driver 331 and an adjustable element 324. The adjustable element 324 includes an expansion element 326 and limiter 328 similar to that described with respect to FIG. 2B. The driver 331 includes a motor 332 and a transmission element 334, in this embodiment a hollow lead screw 325 through which a cable 327 passes. The cable 327 runs through the expansion element 326 and has a stop 336 crimped to one end. The limiter 328 is a generally cylindrically-shaped element that is slidably disposed about the cable 327 and acts as a bearing surface between the screw 325 and the expansion element 326, in particular a bearing arm 339 coupled to the expansion element 326. A similar bearing arm is disposed proximate the stop 336, to distribute loads along the depth of the expansion element 326. In one embodiment, the motor 332 is a 8-10 mm pager motor with a 50:1 gear reduction. The cable 327, screw 325, limiter 328, and bearing arm 339 may be made of a polymer, steel, stainless steel, or other suitable material. In one embodiment, the cable 327 is made from stainless steel coated with a friction-reducing material, such as that sold by DuPont under the trademark Teflon®.

In operation, the cable 327 is fixedly attached to the driver 331 and has a fixed length. The cable 327 runs through the screw 325, which determines the amount of longitudinal travel of the expansion element 326 that is possible. For example, as a vertical force is applied to the expansion element 326, the element 326 expands longitudinally along the cable 327 until it hits the limiter 328, which is disposed between the expansion element 326 and the end of the screw 325. The motor 332 rotates the screw 325 to vary the length of the cable 327 that the limiter 328 can slide along before contacting the screw 325 and expansion element 326. The screw 325 moves a predetermined distance either towards or away from the element 326 in response to the signal from the control system. In one embodiment, the screw 325 may travel between about 0 mm to about 20 mm, preferably about 0 mm to about 10 mm.

In an alternative embodiment, the adjustable element 324 includes two motors 332 and cables 327 oriented substantially parallel to one another. Two cables 327 aid in holding the expansion element 326 square relative to a longitudinal axis 360 of the adjustable element 324 depicted in FIG. 3. In addition, other types of expansion element/limiter arrangements are possible. For example, a circumferential or belly band type limiter may be used instead of a diametral or longitudinal type limiter. In operation, the driver 331 varies the circumference of the belly band to vary the range of expansion of the element 326, the larger the circumference, the larger the range of expansion. Other possible arrangements include shape memory alloys and magnetorheological fluid.

Figure 4A:
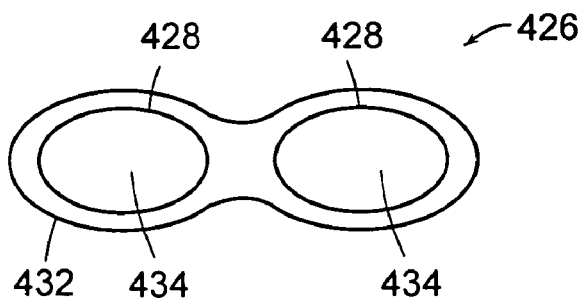
FIGS. 4A-4E are schematic side views of alternative embodiments of an adjustable element in accordance with the invention.
Figure 4B:
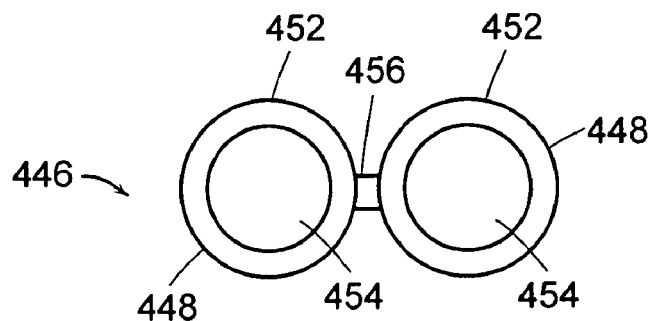
Figure 4C:
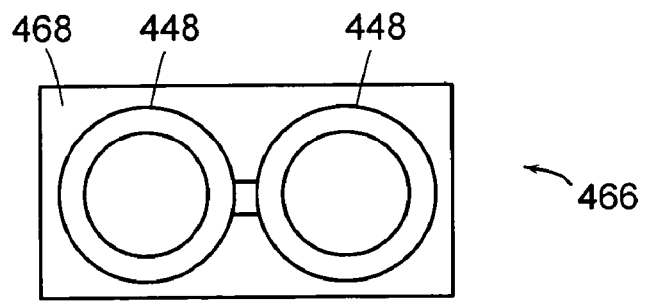
Figure 4D:
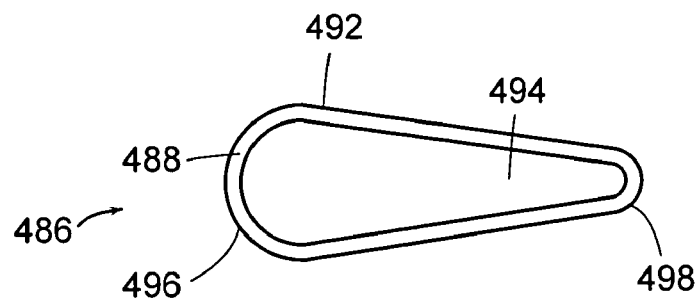

FIGS. 4A-4E depict alternative adjustable elements, with each shown in an unloaded state. In particular, FIGS. 4A-4D depict certain different possible shapes for the expansion element. In FIG. 4A, the expansion element 426 includes two cylinders 428 having generally elliptically-shaped cross-sections and formed as a single element. Alternatively, the cylinder cross-sectional shape could be any combination of linear and arcuate shapes, for example, hexagonal or semi-circular. The cylinders 428 include a wall 432 and a pair of cores 434 that may be hollow or filled with a foam or other material. FIG. 4B depicts an expansion element 446 having two separate cylinders 448 having generally circular cross-sections and coupled together. The cylinders 448 each have a wall 452 and a core 454. FIG. 4C depicts an expansion element 466 including two cylinders 448 as previously described. In FIG. 4C, the expansion element 466 includes a foam block 468 surrounding the cylinders 448. The foam block 468 may replace the core or be additional to the core. FIG. 4D depicts yet another embodiment of an expansion element 486. The expansion element 486 includes a cylinder 488 having an elongate sector cross-sectional shape. The cylinder includes a wall 492 and a core 494. The cylinder 488 includes a first arcuate end 496 and a second arcuate end 498. The first arcuate end 496 has a substantially larger radius than the second arcuate end 498, thereby resulting in greater horizontal displacement at the first arcuate end when under load. Additionally, the wall thickness of any cylinder can be varied and/or the cylinder could be tapered along its length. In embodiments of the expansion element 126 that use a foam core, it is undesirable to bond the foam core to the walls of the expansion element 126. Bonding the foam to the walls may inhibit horizontal expansion.

Figure 4E:
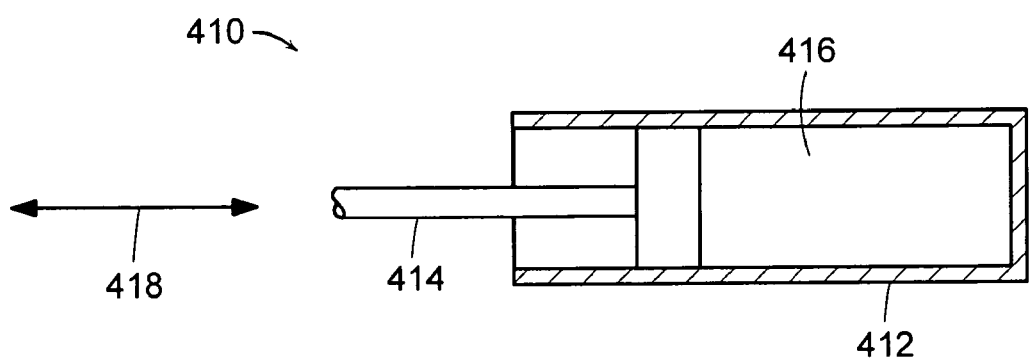

FIG. 4E depicts an alternative type of adjustable element 410. The adjustable element 410 includes a relatively flexible structural cylinder 412 and piston 414 arrangement. The internal volume 416 of the cylinder 412 varies as the piston 414 moves into and out of the cylinder 412, shown generally by arrow 418. The piston 414 is moved linearly by the driver 131 in response to the signal from the control system 120. By varying the volume 416, the compressibility of the cylinder 412 is varied. For example, when the piston 414 is moved into the cylinder 412, the volume is reduced and the pressure within the cylinder is increased; the greater the pressure, the harder the cylinder. While this system may appear similar to that of an inflatable bladder, there are differences. For example, in this system, the amount of fluid, e.g., air, stays constant, while the volume 416 is adjusted. Further, bladders primarily react based on the pressure within the bladder, whereas the element 410 depicted in FIG. 4E uses the structure of the cylinder in combination with the internal pressure. The two are fundamentally different in operation. For example, the inflatable bladder, like a balloon, merely holds the air in and provides no structural support, while the cylinder, like a tire, uses the air to hold up the structure (e.g. the tire sidewalls). In addition, the piston 414 and driver 131 arrangement allows for fine adjustment of the pressure and compressibility of the adjustable element 410.

Figure 5A:
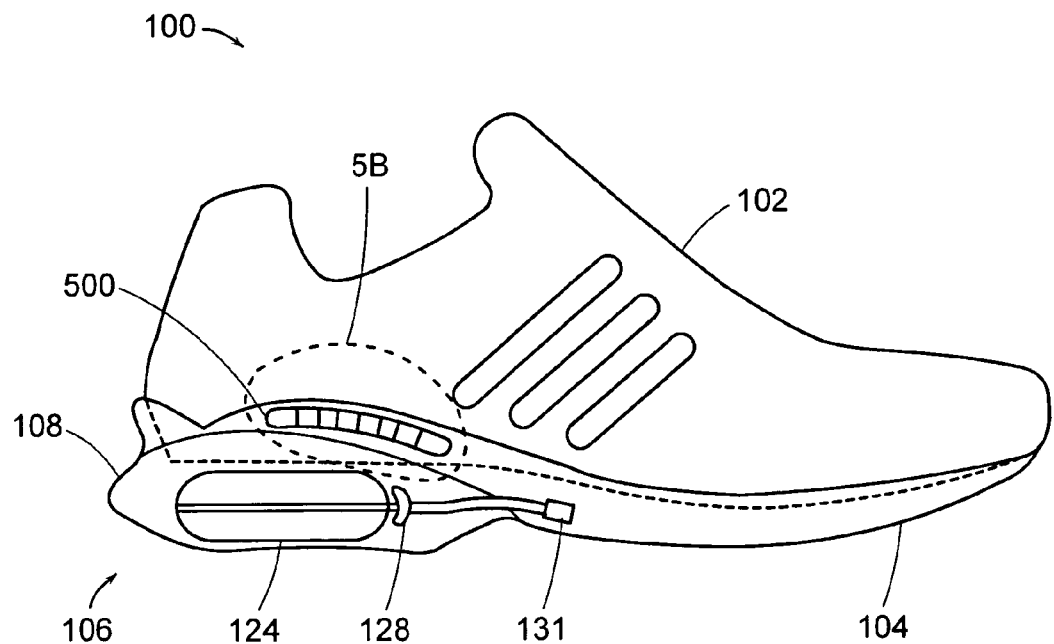
FIG. 5A is a schematic side view of the article of footwear of FIG. 1 showing select internal components.

FIG. 5A depicts a side view of the article of footwear 100 of FIG. 1. The intelligent system 106 is disposed generally in the rearfoot portion 108 of the article of footwear 100. As shown in FIG. 5A, the intelligent system 106 includes the adjustable element 124 with the limiter 128 and the driver 131. Also shown is a user-input module 500 (FIG. 5B) including user-input buttons 502, 504 and an indicator 506. The user can set the compression range or other performance characteristic target value of the article of footwear 100, by pushing input button 502 to increase the target value or pushing input button 504 to decrease the target value or range. In an alternative embodiment, the user-input module 500 can be remotely located from the shoe. For example, a wristwatch, personal digital assistant (PDA), or other external processor could be used alone or in combination with the user-input module 500 disposed on the article of footwear, to allow the user to customize characteristics of the intelligent system 106. For example, the user may press buttons on the wristwatch to adjust different characteristics of the system 106. In addition, the system 106 may include an on and off switch.

Figure 5B:
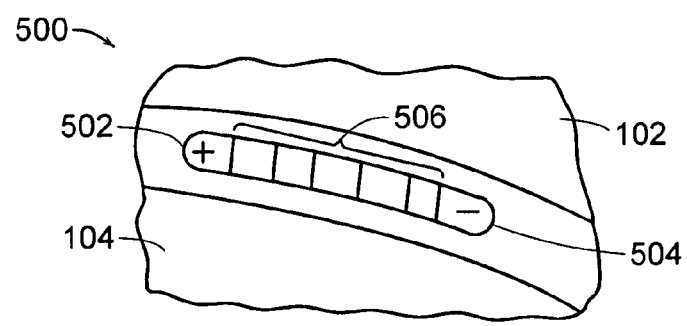
FIG. 5B is an enlarged schematic view of a portion of the article of footwear of FIG. 5A.

The user-input module 506 is shown in greater detail in FIG. 5B. The indicator(s) 506 may be one or more electro-luminescent elements, for example. In the embodiment shown, the indicator 506 is a series of electro-luminescent elements printed on a flex-circuit that glow to indicate the range of compression selected; however, the indicators could also indicate the level of hardness of the midsole or some other information related to a performance characteristic of the footwear 100. Alternatively or additionally, the indicator may be audible.

Figure 6:
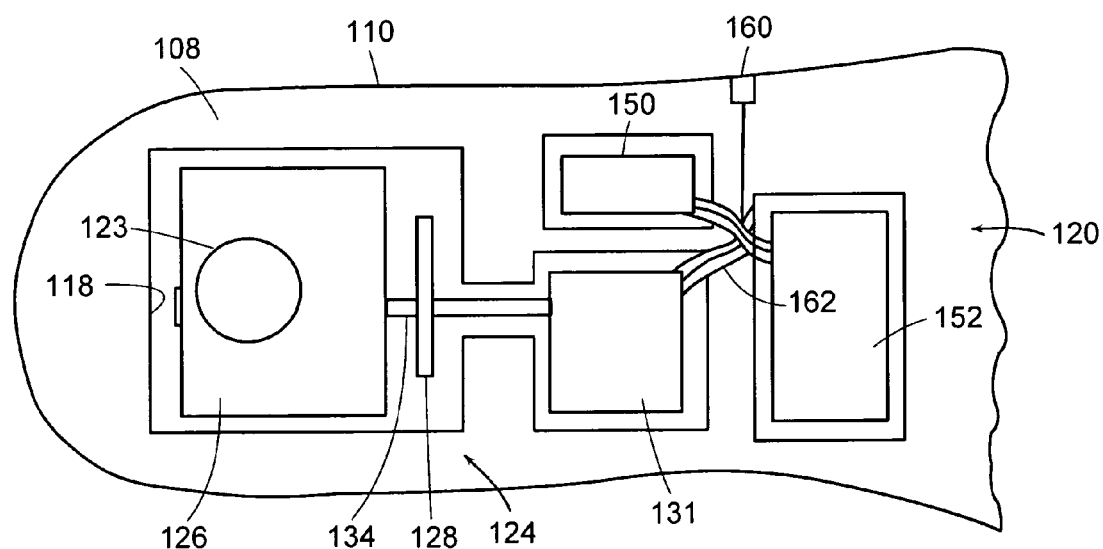
FIG. 6 is a schematic top view of a portion of the sole of FIG. 2A with a portion of the sole removed to illustrate the layout of select internal components of the intelligent system.

FIG. 6 depicts a top view of one possible arrangement of select components of the intelligent system of FIG. 1. The adjustable element 124 is disposed in the rearfoot portion 108 of the midsole 110 with the expansion element 126 laterally disposed within the cavity 118. The driver 131 is disposed adjacent to the expansion element 126. Adjacent to the driver 131 is the control system 120. The control system 120 includes a control board 152 that holds a micro-controller for controlling the driver 131 and for processing the algorithm. Further, the system 106 includes a power source 150, for example a 3.0V ½ AA battery. The power source 150 supplies power to the driver 131 and the control system 120 via wires 162 or other electrical connection, such as a flexcircuit.

The system 106 further includes the magnet 123 and the aligned sensor 122 (not shown), which is located under the expansion element 126 and is electrically coupled to the control system 120. The magnet 123 is located above the expansion element 126, but below an insole and/or sock liner. Further, the entire intelligent system 106 can be built into a plastic casing to make the system 106 waterproof. In addition, the system 106 can be built as a single module to facilitate fabrication of the sole 104 and may be pre-assembled to the lower support plate 114 (not shown in FIG. 6). In one embodiment, the system 106 is removable, thereby making the system 106 replaceable. For example, the outsole 112a, 112b may be configured (e.g., hinged) to allow the system to be removed from the cavity 118 of the midsole 110.

The system 106 may also include an interface port 160 that can be used to download data from the intelligent system 106, for example to a PDA or other external processor. The port 106 can be used to monitor shoe performance. In an alternative embodiment, the data can be transmitted (e.g., via radio waves) to a device with a display panel located with the user. For example, the data can be transmitted to a wristwatch or other device being worn the user. In response to the data, the user may adjust certain characteristics of the shoe by pressing buttons on the wristwatch, as described above. These adjustments are transmitted back to the system 106 where the adjustments are implemented.

Figure 7:
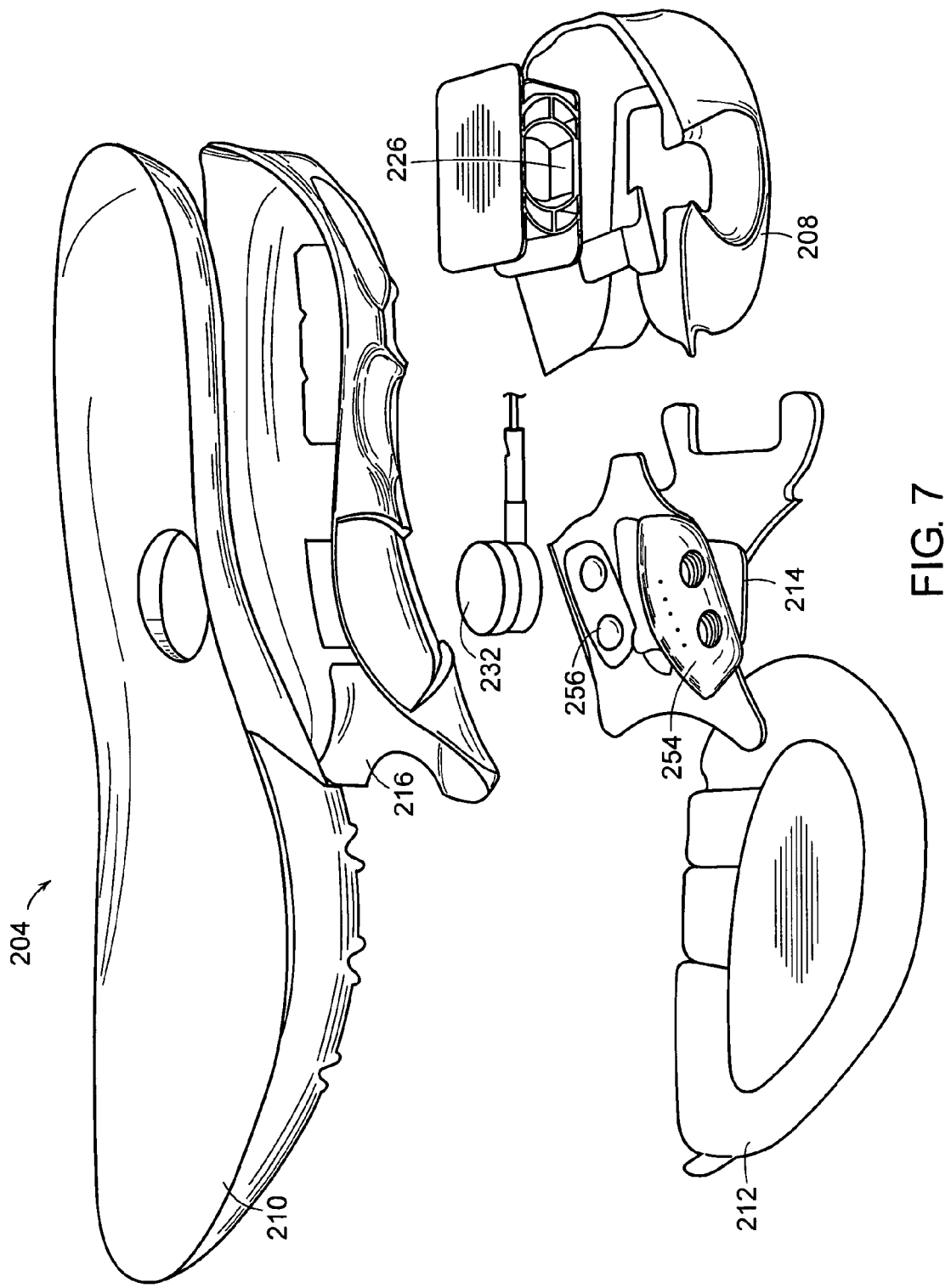
FIG. 7 is an exploded schematic perspective view of a sole of the article of footwear of FIG. 1 in accordance with another embodiment of the invention.

FIG. 7 depicts an exploded perspective view of a sole 204 of the article of footwear 100 of FIG. 1 in accordance with another embodiment of the invention. The sole 204 includes a midsole 210, an outsole 212, an optional lower support plate 214, and an optional upper support plate 216. A rearfoot portion 208 of the sole 204 may be made from, for example, a foam, such as a polyurethane (PU) or ethylene vinyl acetate (EVA) foam, and may be adapted to receive an expansion element 226. In one embodiment, the expansion element 226 is, as shown, shaped like a honeycomb; however, the element 226 may also be generally cylindrical, with an elongated circular or elongated generally elliptically-shaped cross-section, or include a series of arched walls with different centers, but identical radii, or any combination thereof. A motor 232 is also positioned within the sole 204 and may be used to adjust the expansion element 226. A user interface 254, including user input buttons 256, may also be provided for receiving user inputs related to the adjustment of the sole 204.

Figure 8A:
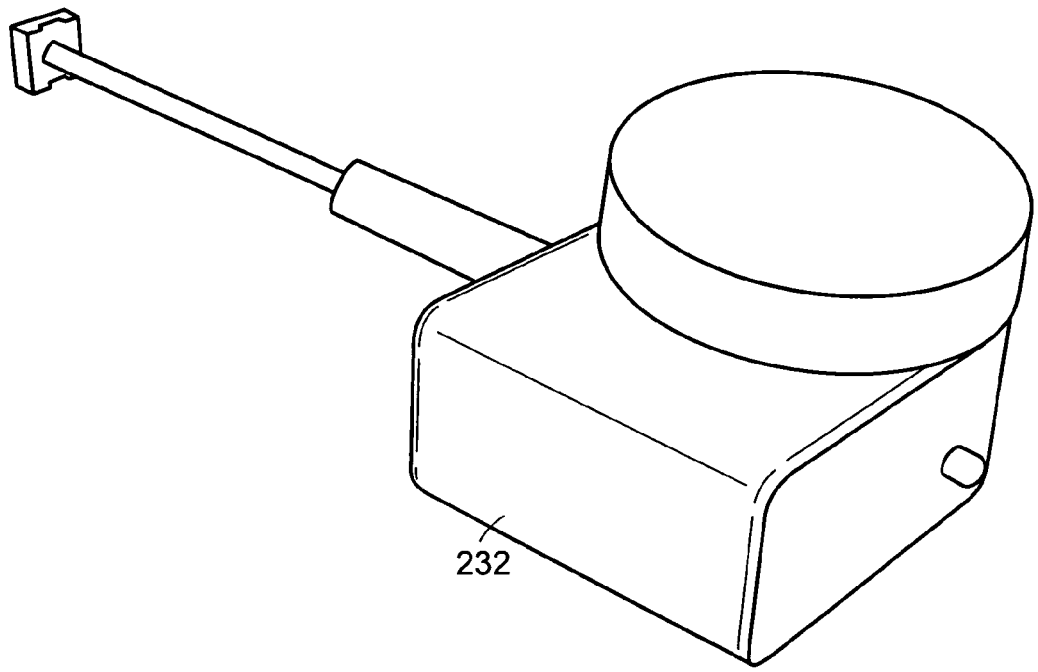
FIGS. 8A-8G are schematic perspective views of various components that may be included in various embodiments of the sole of FIG. 7 in accordance with the invention.
Figure 8B:
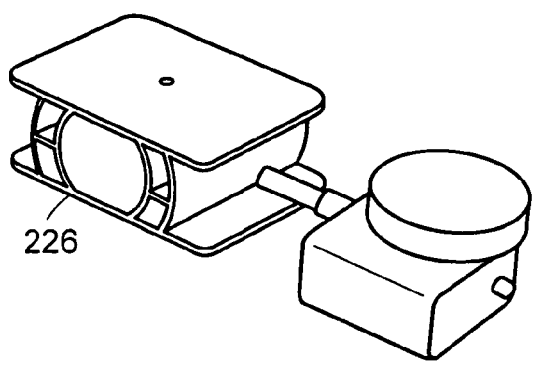
Figure 8C:
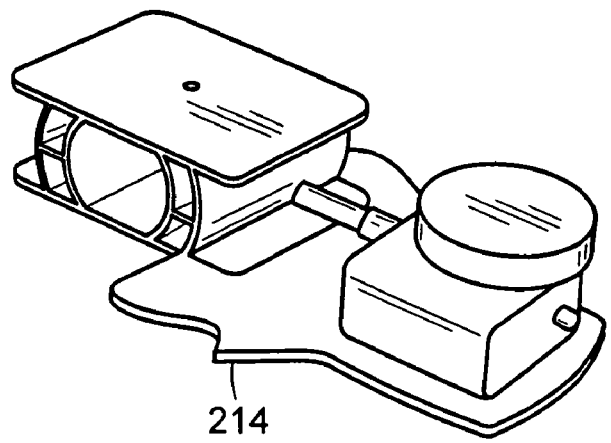
Figure 8D:
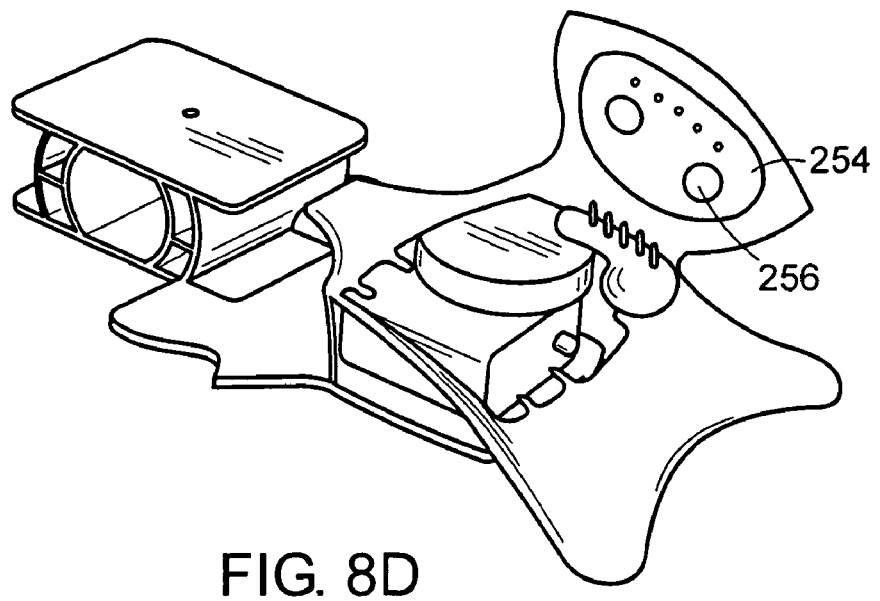
Figure 8E:
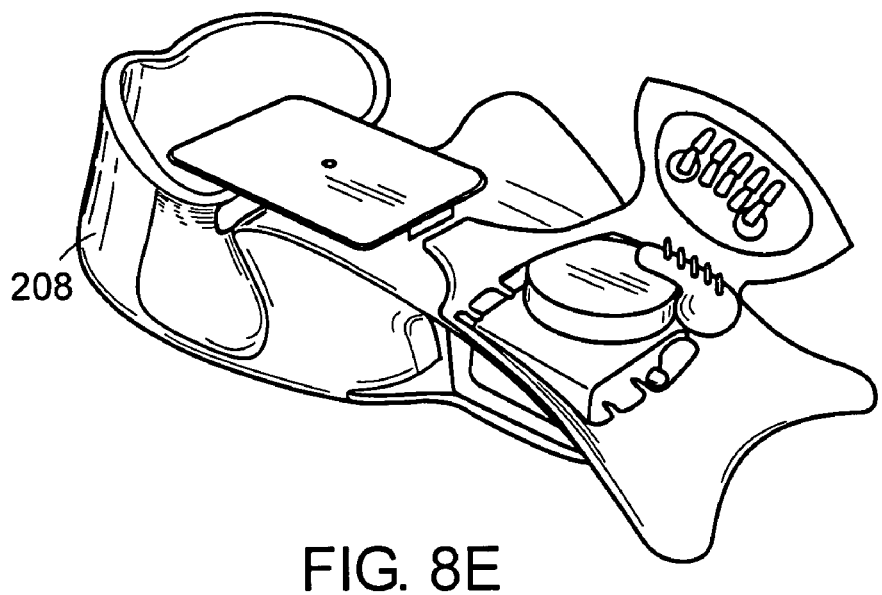
Figure 8F:
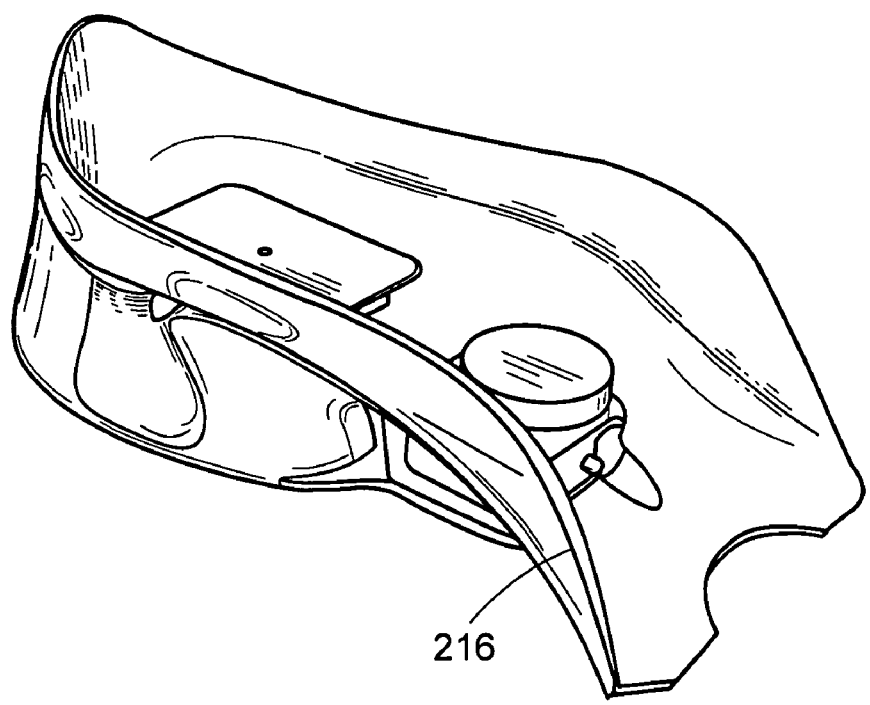
Figure 8G:
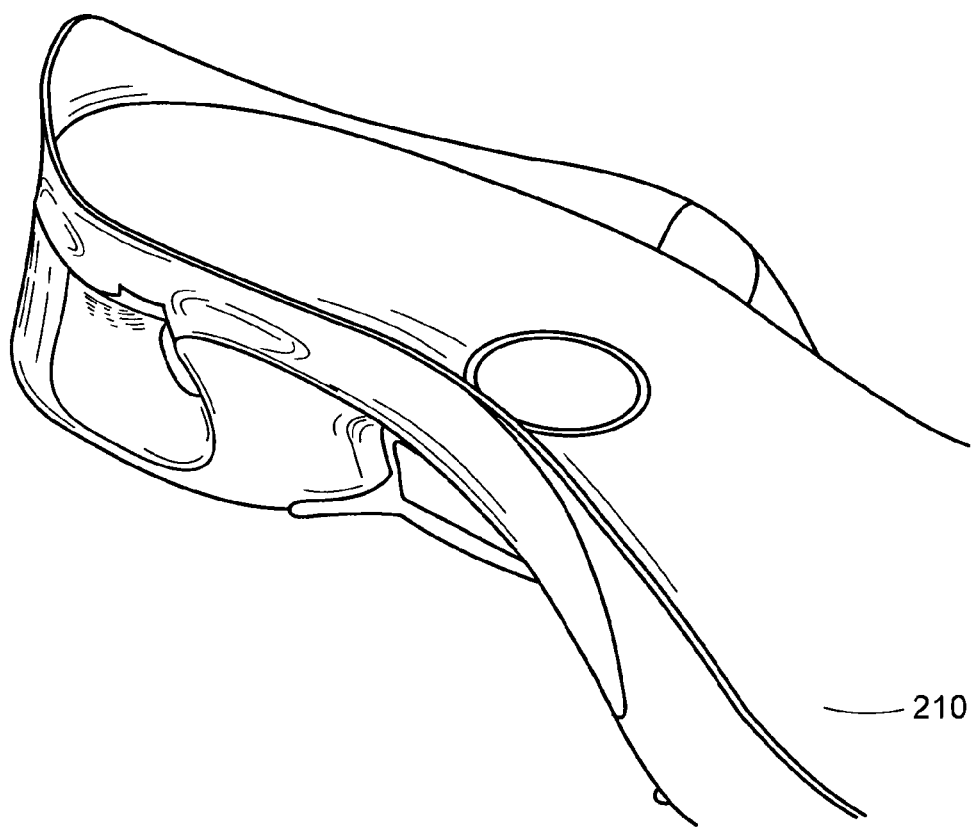

FIGS. 8A-8G depict perspective views of various components that may be included in various embodiments of the sole 204. The components include the motor 232 (FIG. 8A), the expansion element 226 (FIG. 8B), the optional lower support plate 214 (FIG. 8C), the user interface 254 and the user input buttons 256 (FIG. 8D), the rearfoot portion 208 that may be made from, for example, the PU or EVA foam (FIG. 8E), the optional upper support plate 216 (FIG. 8F), and the midsole 210 (FIG. 8G).

Figure 9:
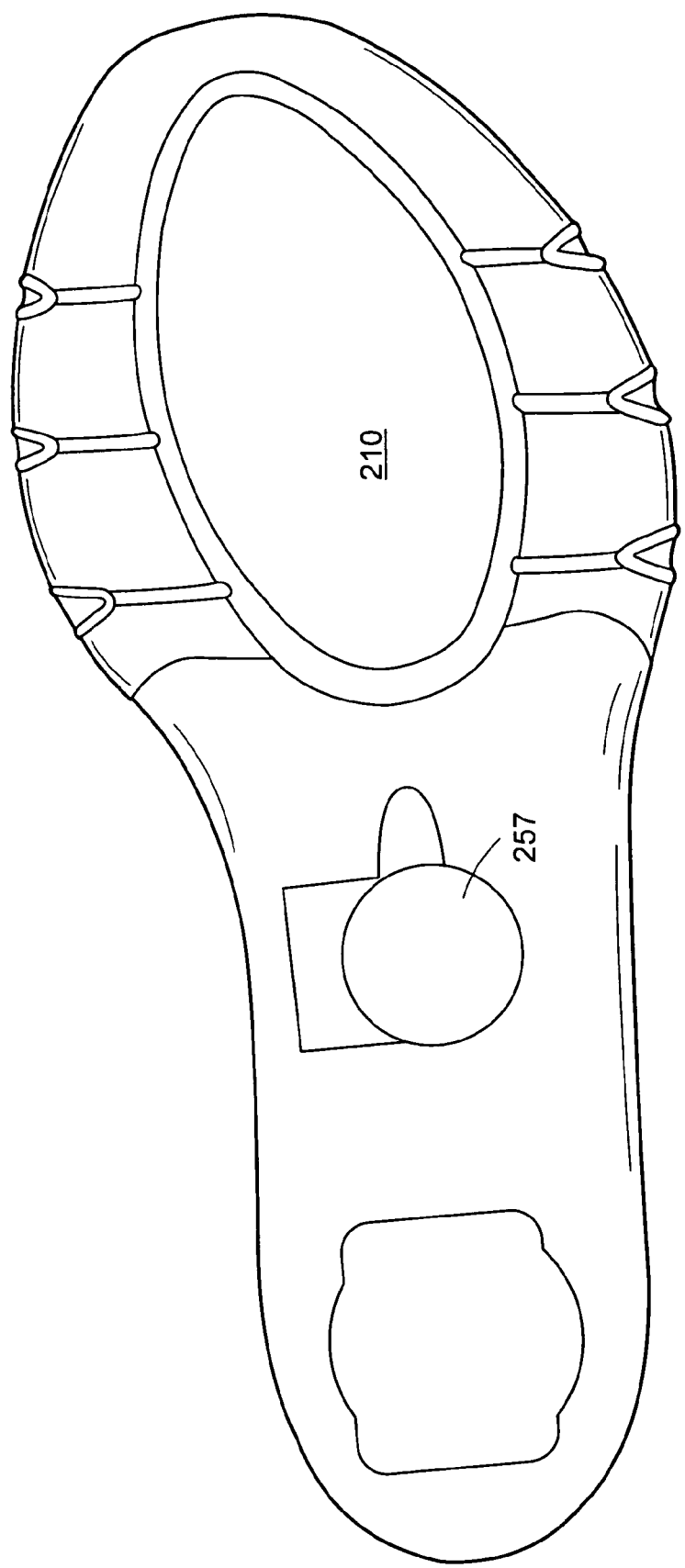
FIG. 9 is a schematic bottom view of the midsole of FIGS. 7 and 8G in accordance with one embodiment of the invention.

FIG. 9 depicts a bottom view of the midsole 210 of FIGS. 7 and 8G. The midsole 210 includes an opening 257 for accessing the power source 150 (see FIG. 6) and related equipment used in the intelligent system 106. The position of the opening 257 in the midsole 210 can vary depending on the location of the power source 150 and related equipment in the sole 204.

Figure 10:
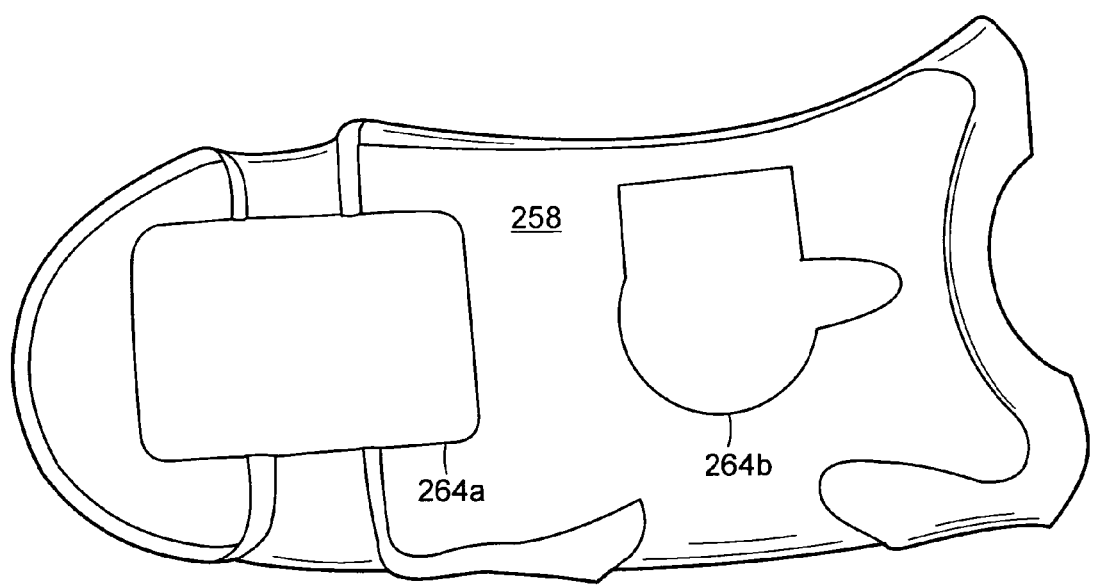
FIG. 10 is a schematic bottom view of an optional torsional bar that may be used with the sole of FIG. 7 in accordance with one embodiment of the invention.

FIG. 10 depicts a bottom view of an optional torsional bar 258 that may be used with the sole 204 of FIG. 7 in accordance with one embodiment of the invention. The torsional bar 258 may include openings 264a, 264b at the heel and at the shank. The openings 264 may provide clearance for, or access to, the various components of the intelligent system 106.

Figure 11:
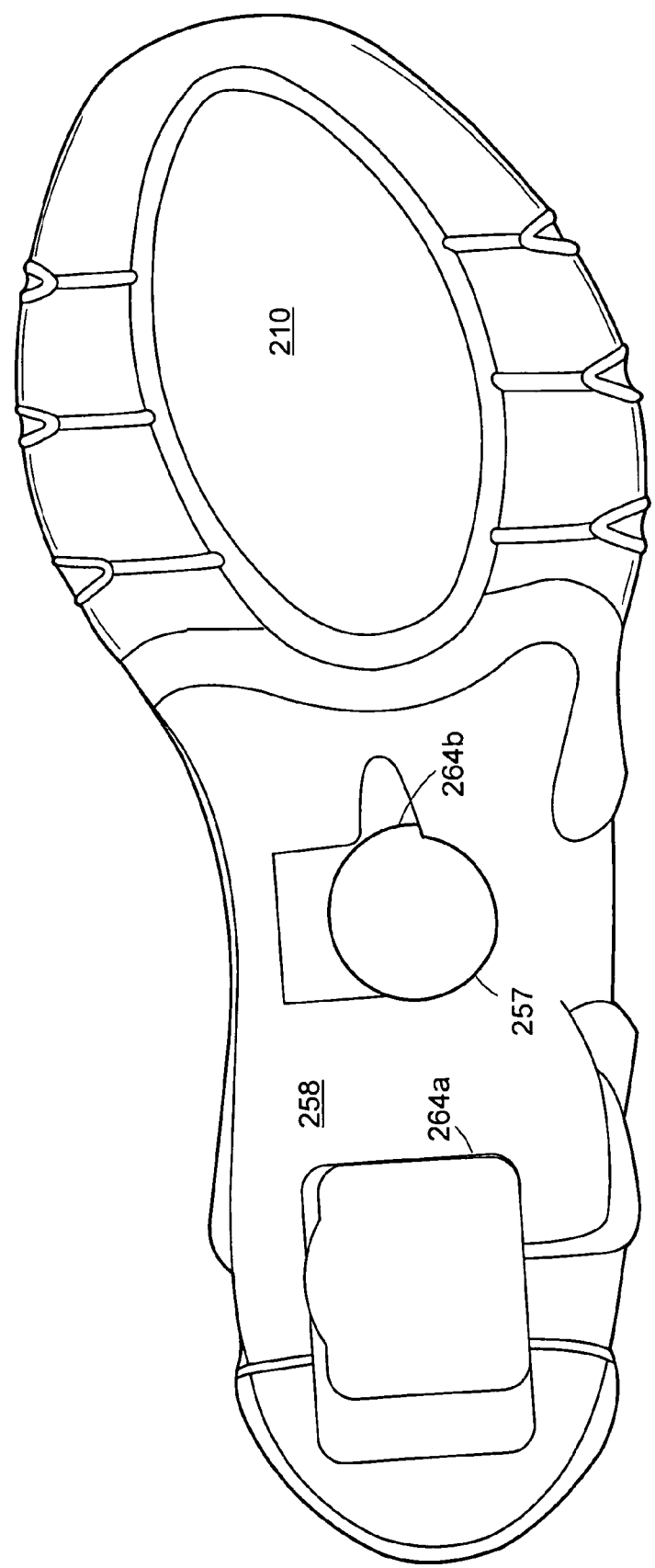
FIG. 11 is a schematic bottom view of the optional torsional bar of FIG. 10 disposed on the midsole of FIG. 9 in accordance with one embodiment of the invention.

FIG. 11 depicts a bottom view of the optional torsional bar 258 of FIG. 10 disposed on the midsole 210 illustrated in FIG. 9 in accordance with one embodiment of the invention. The opening 264b on the torsional bar 258 aligns with the opening 257 in the midsole 210 to enable a user to access the power source 150 and related equipment in the sole 204.

Figure 12:
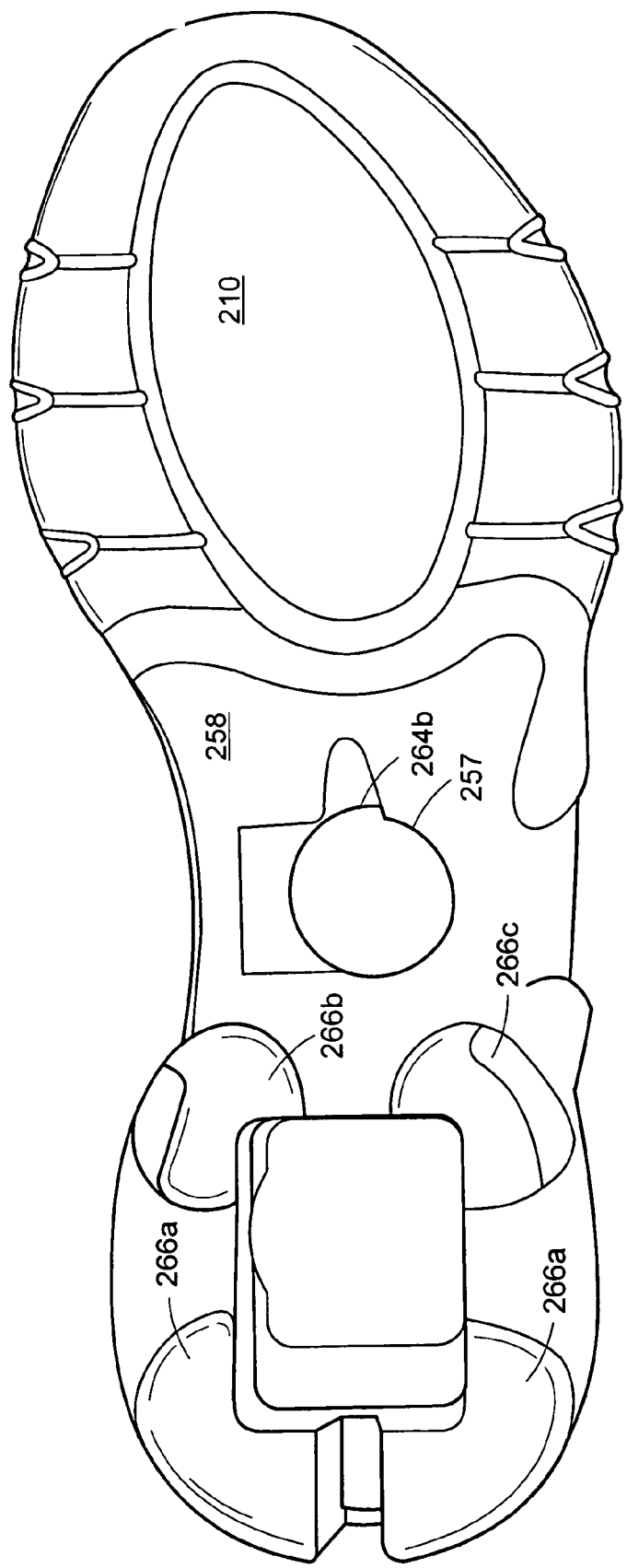
FIG. 12 is a schematic bottom view of the midsole and the optional torsional bar of FIG. 11, further including additional heel foam elements in accordance with one embodiment of the invention.

FIG. 12 depicts a bottom view of the midsole 210 and the optional torsional bar 258 of FIG. 11, further including additional heel foam elements 266a, 266b, 266c in accordance with one embodiment of the invention. The illustrated embodiment includes three heel foam elements: (1) a rear foam element 266a extending from a medial to a lateral side of the midsole 210; (2) a medial front foam 266b element; and (3) a lateral front foam element 266c. The hardness of the foam elements 266 may vary to suit a particular application. For example, the lateral front foam element 266c may be harder than the rear foam element 266a. The material properties may vary between and within the different foam elements 266 to perform different functions, for example, to guide the foot into a neutral position between pronation and supination during a step cycle. The use of foam elements for cushioning and guidance is described in greater detail in U.S. Pat. No. 6,722,058 and U.S. patent application Ser. No. 10/619,652, the disclosures of which are hereby incorporated by reference herein in their entireties. Details of additional structural elements that can be used in an article of footwear with an intelligent system are described in greater detail in U.S. patent application Ser. No. 11/346,998, the disclosure of which is hereby incorporated by reference herein in its entirety.

Figure 13:
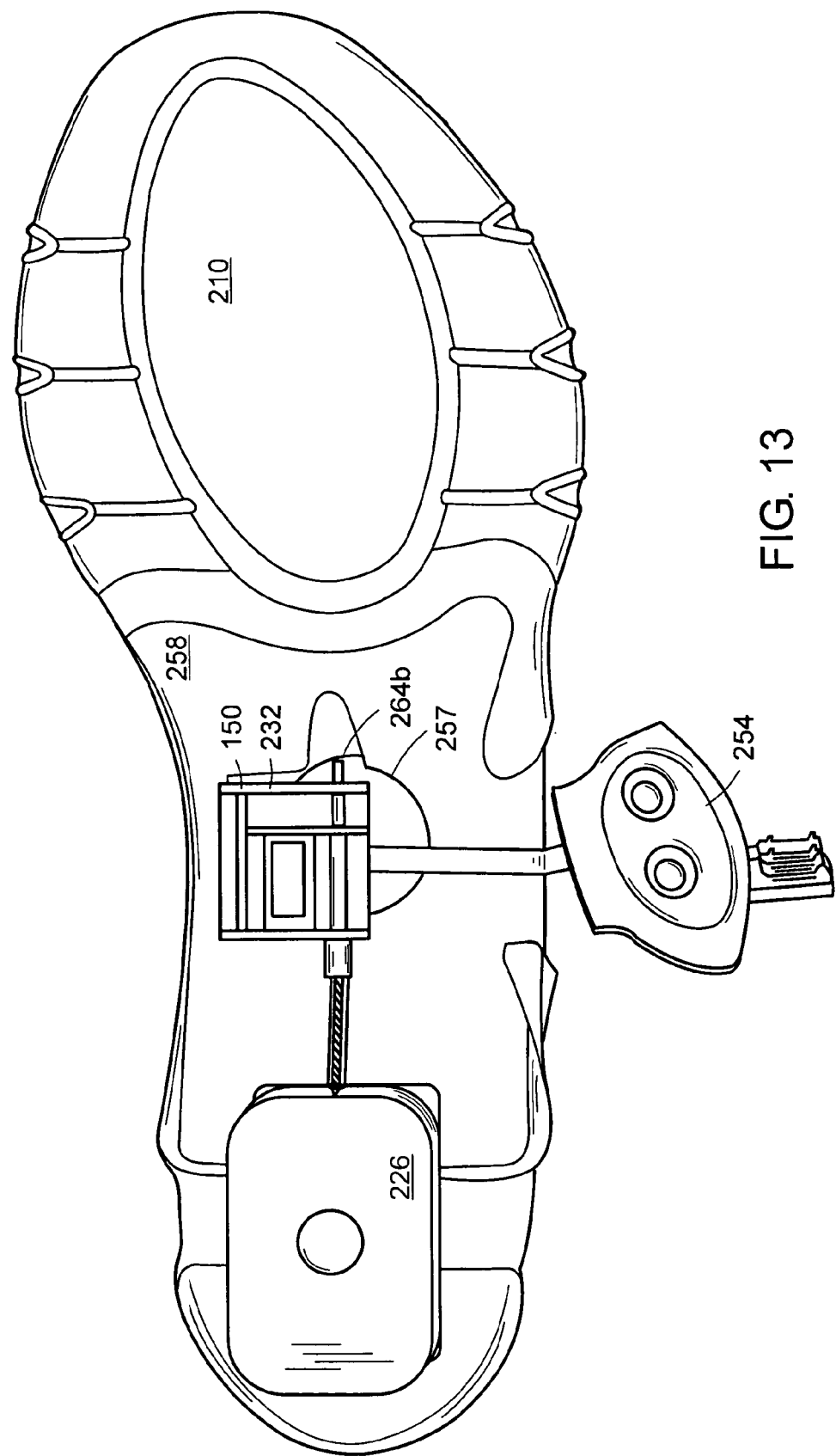
FIG. 13 is a schematic bottom view of the midsole and the optional torsional bar of FIG. 11, further including additional components in accordance with one embodiment of the invention.

FIG. 13 depicts a bottom view of the midsole 210 and the optional torsional bar 258 of FIG. 11, further including the motor 232 and the power source 150 disposed in the openings 257, 264b that extend through the midsole 210 and optional torsional bar 258, the user interface 254, and the expansion element 226 in accordance with one embodiment of the invention. Alternatively or additionally, the expansion element 226 could be located in the forefoot area of the sole 204, or at substantially any position along the sole 204. In addition, the orientation of the expansion element 226 in the sole 204 can be varied to suit a particular application. For example, in one embodiment, the intelligent system could be located on only the medial or lateral side to provide a controlled dual density sole, one part of which would be automatically adjustable.

Figure 14:
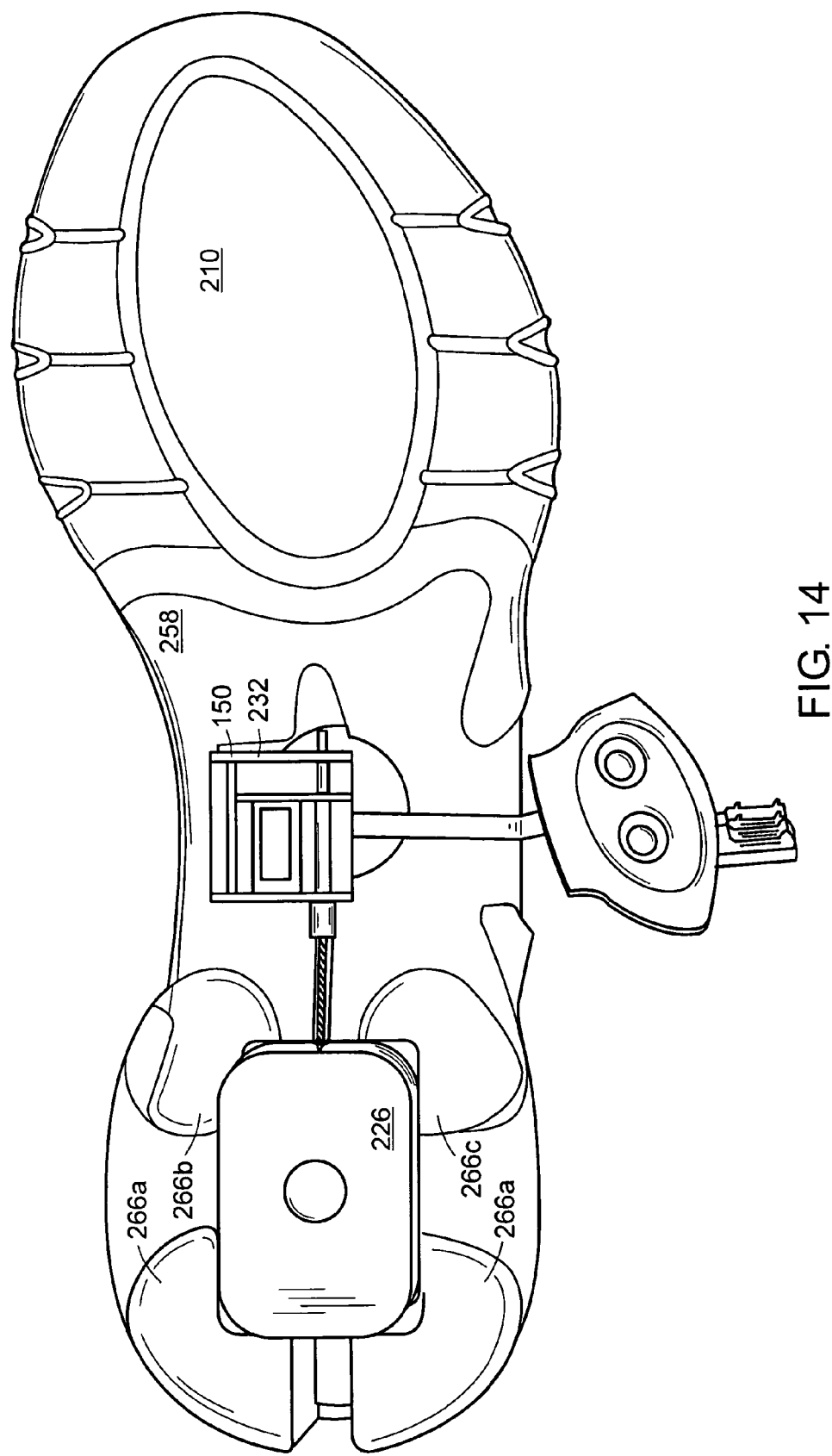
FIG. 14 is a schematic bottom view of the midsole of FIG. 13 further including the additional heel foam elements of FIG. 12 in accordance with one embodiment of the invention.

FIG. 14 depicts a bottom view of the midsole 210 of FIG. 13 further including the additional heel foam elements 266a, 266b, 266c of FIG. 12 in accordance with one embodiment of the invention. In the illustrated embodiment, the expansion element 226 is shown embedded between the three foam elements 266a, 266b, 266c.

Figure 15:
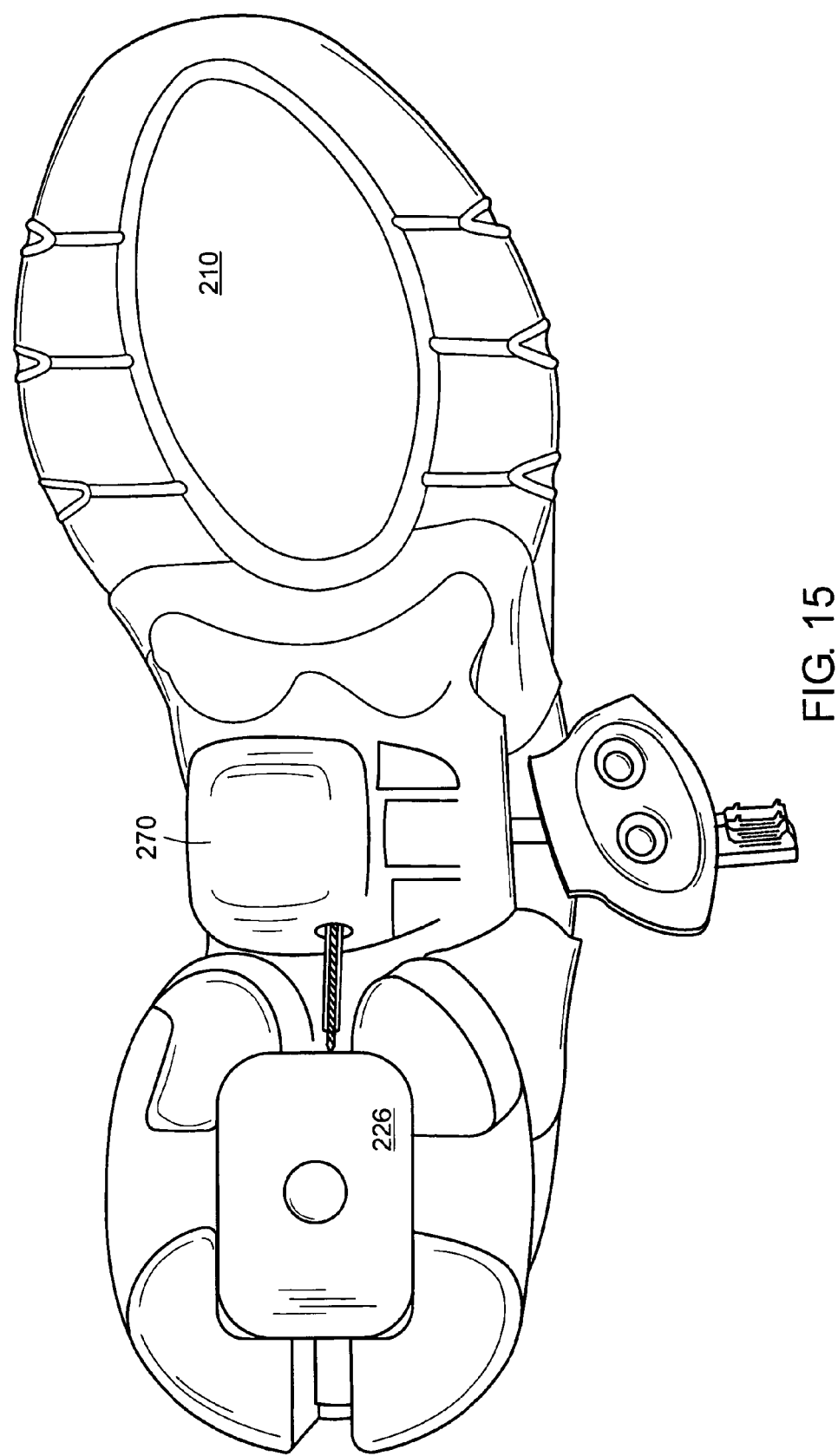
FIG. 15 is a schematic bottom view of the midsole of FIG. 14 further including a casing that covers the various components of the intelligent system in accordance with one embodiment of the invention.

FIG. 15 depicts a bottom view of the midsole 210 of FIG. 14 further including a casing 270 that covers the power source 150 and other electronic components in accordance with one embodiment of the invention. The casing 270 can optionally be removed to enable a user to access the power source 150 and other electronic equipment.

Figure 16:
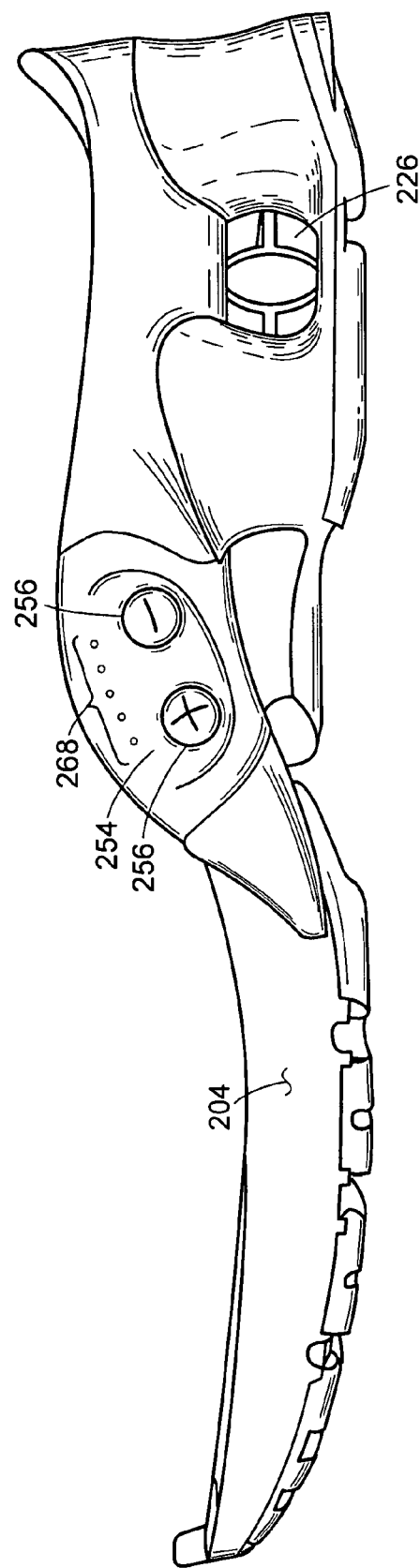
FIG. 16 is a schematic lateral perspective view of a sole including a honeycombed shaped expansion element and a user interface in accordance with one embodiment of the invention.

FIG. 16 is a lateral perspective view of the sole 204 including the honeycombed shaped expansion element 226 and the user interface 254 that may be used to alter the settings of the intelligent system 106 in accordance with one embodiment of the invention. In various embodiments, the sole 204 can include multiple expansion elements 226. A cable element (not shown) may extend between the medial front foam element 266b and the lateral front foam element 266c, and also between the rear foam elements 266a. The expansion elements 226 can be coupled together by the cable passing therethrough. The user interface 254 includes buttons 256 to increase (+) and/or decrease (−) the performance characteristic(s) of the intelligent system 106 and electro-luminescent elements 268 to indicate the system setting.

Figure 17:
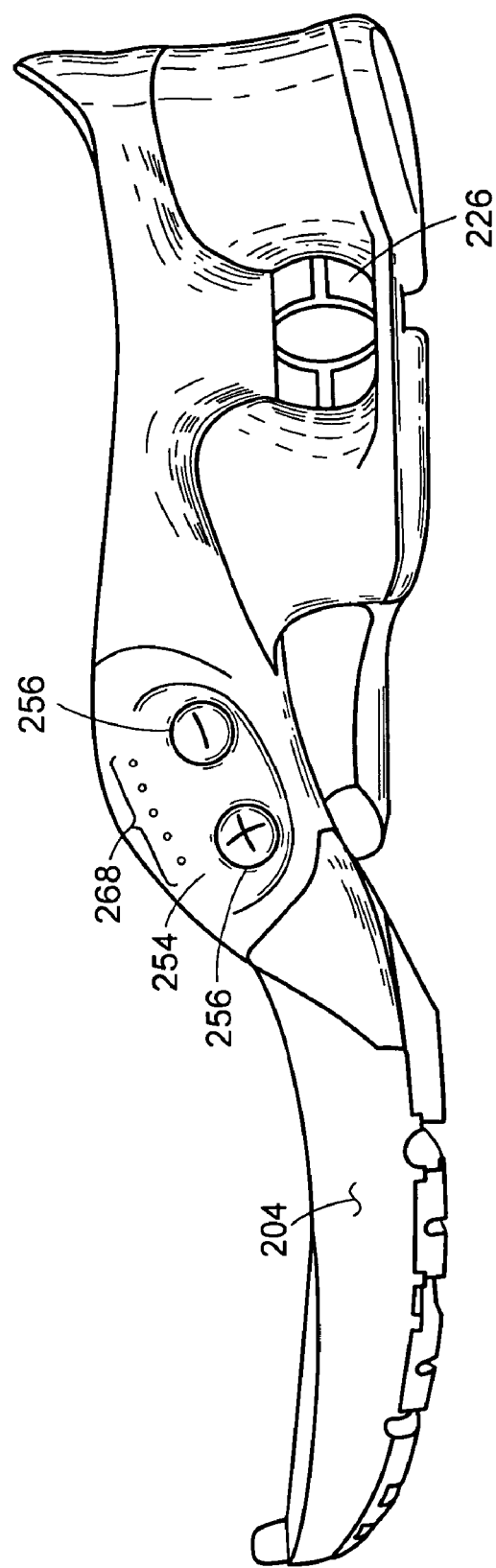
FIG. 17 is a schematic lateral side view of the sole of FIG. 16.

FIG. 17 is a lateral side view of the sole 204 of FIG. 16, where the expansion element 226 is more fully illustrated. The expansion element 226 is, as shown, shaped like a honeycomb; however, the element 226 may also be generally cylindrical, with an elongated circular or elongated generally elliptically-shaped cross-section, or include a series of arched walls with different centers, but identical radii, or any combination thereof.

Figure 18:
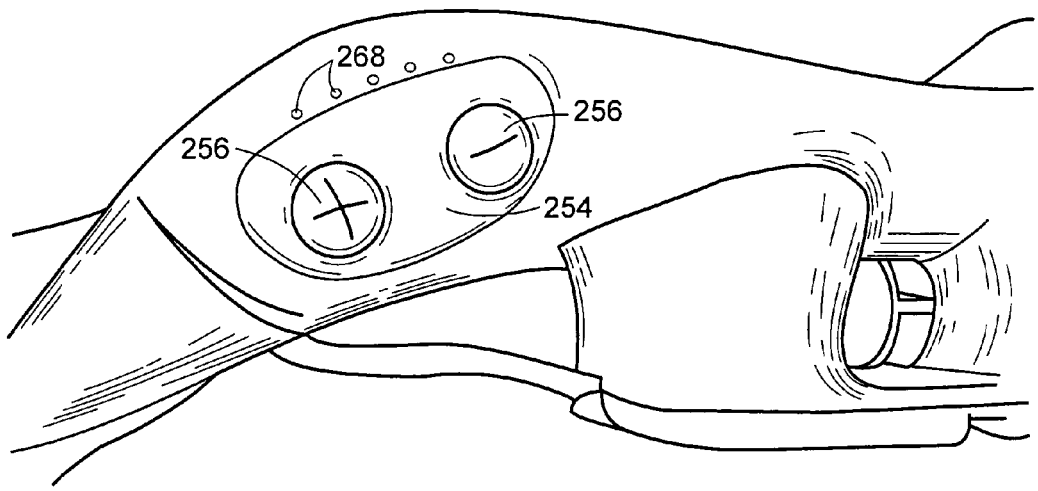
FIG. 18 is an enlarged schematic lateral perspective view of the user interface of FIG. 16 in accordance with one embodiment of the invention.

FIG. 18 is an enlarged lateral view of the user interface 254 of FIG. 16 illustrating the buttons 256 that are used to increase (+) and/or decrease (−) the performance characteristic(s) provided by the intelligent system 106 and the electro-luminescent elements 268 that indicate the system setting in accordance with one embodiment of the invention.

Figure 19:
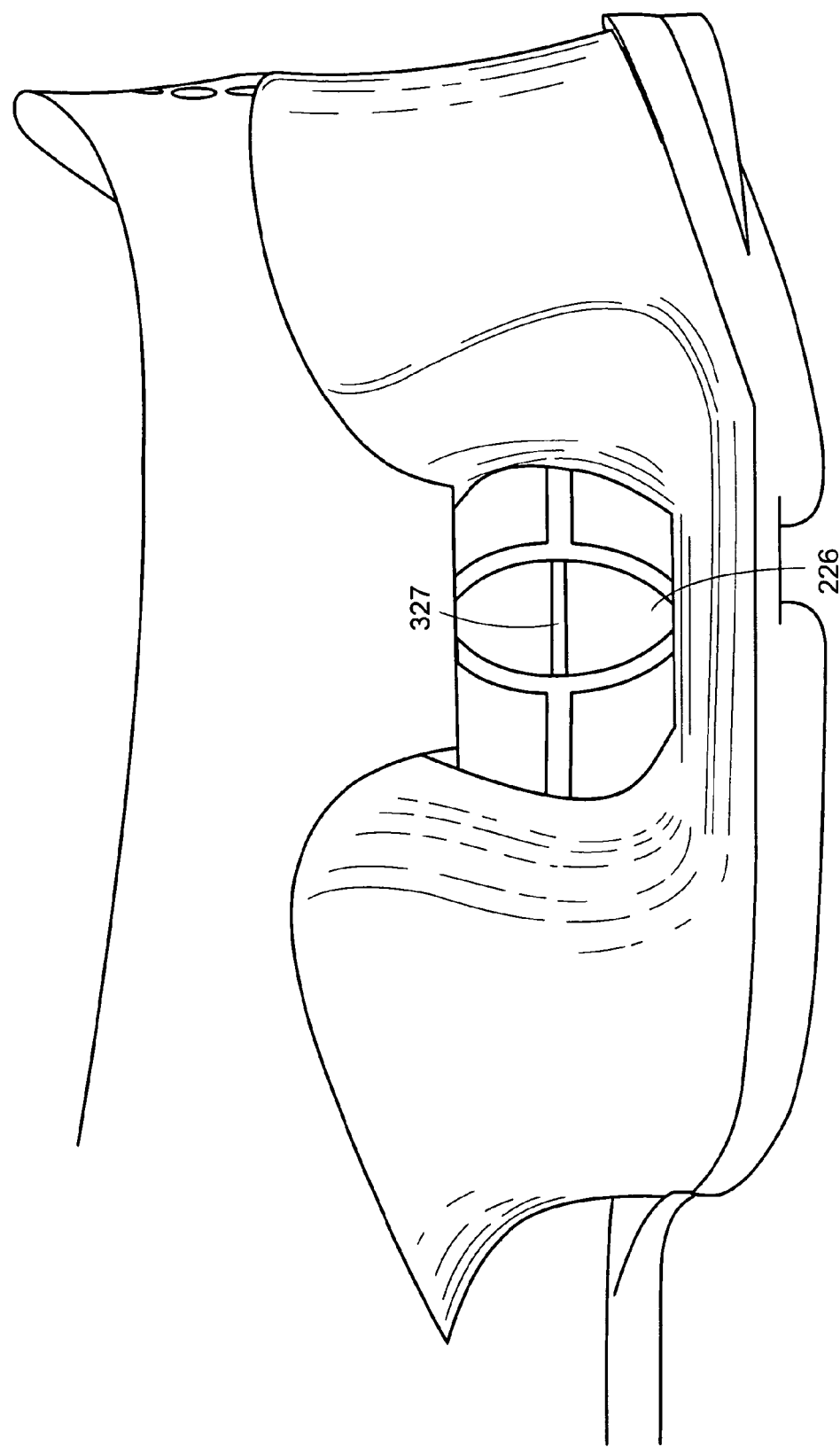
FIG. 19 is an enlarged schematic lateral side view of the expansion element of FIG. 16 in accordance with one embodiment of the invention.

FIG. 19 is an enlarged lateral side view of the expansion element 226 of FIG. 16 illustrating its honeycomb shape in accordance with one embodiment of the invention. In addition, a cable 327 is shown running through the middle of the expansion element 226.

Figure 20:
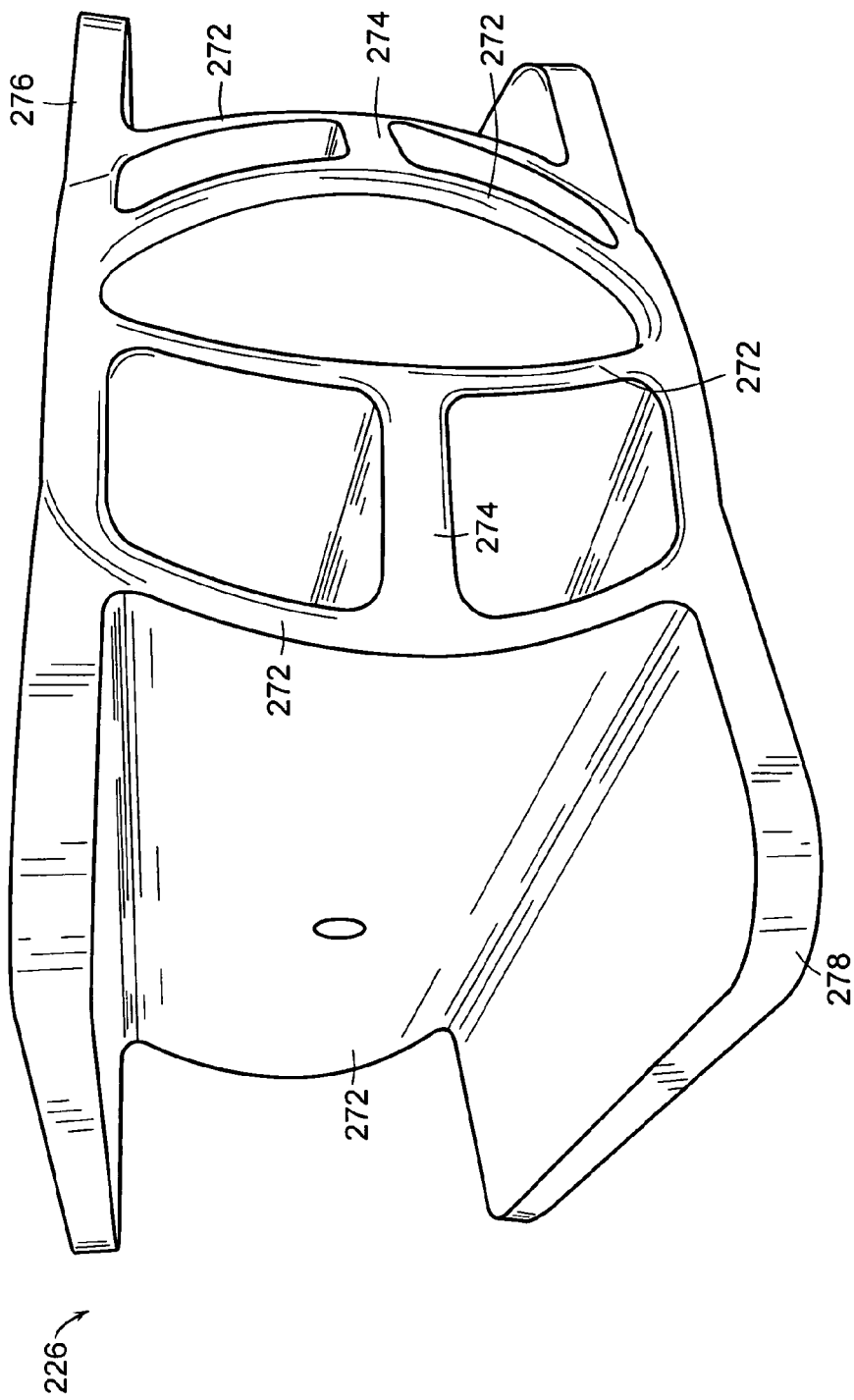
FIG. 20 is a schematic perspective view of the expansion element of FIG. 16 in accordance with one embodiment of the invention.

FIG. 20 depicts a perspective view of the expansion element 226 of FIG. 16 in accordance with one embodiment of the invention. The expansion element 226 has four generally vertical side walls 272 (two on each side), whereby a generally horizontal bar 274 connects the adjacent side walls 272 on each side to each other, thereby forming the generally honeycomb-like structure. The horizontal bar 274 is generally centrally disposed between the side walls 272. The horizontal bars 274 provide stability against shear forces in a longitudinal direction and in some instances may be under tension. In one embodiment, the side walls 272 have a generally arcuate shape; however, the side walls 272 and the horizontal bar 274 can be linear, arcuate, or combinations thereof. The expansion element 226 may also include a top bar 276 and a bottom bar 278.

Figure 21A:
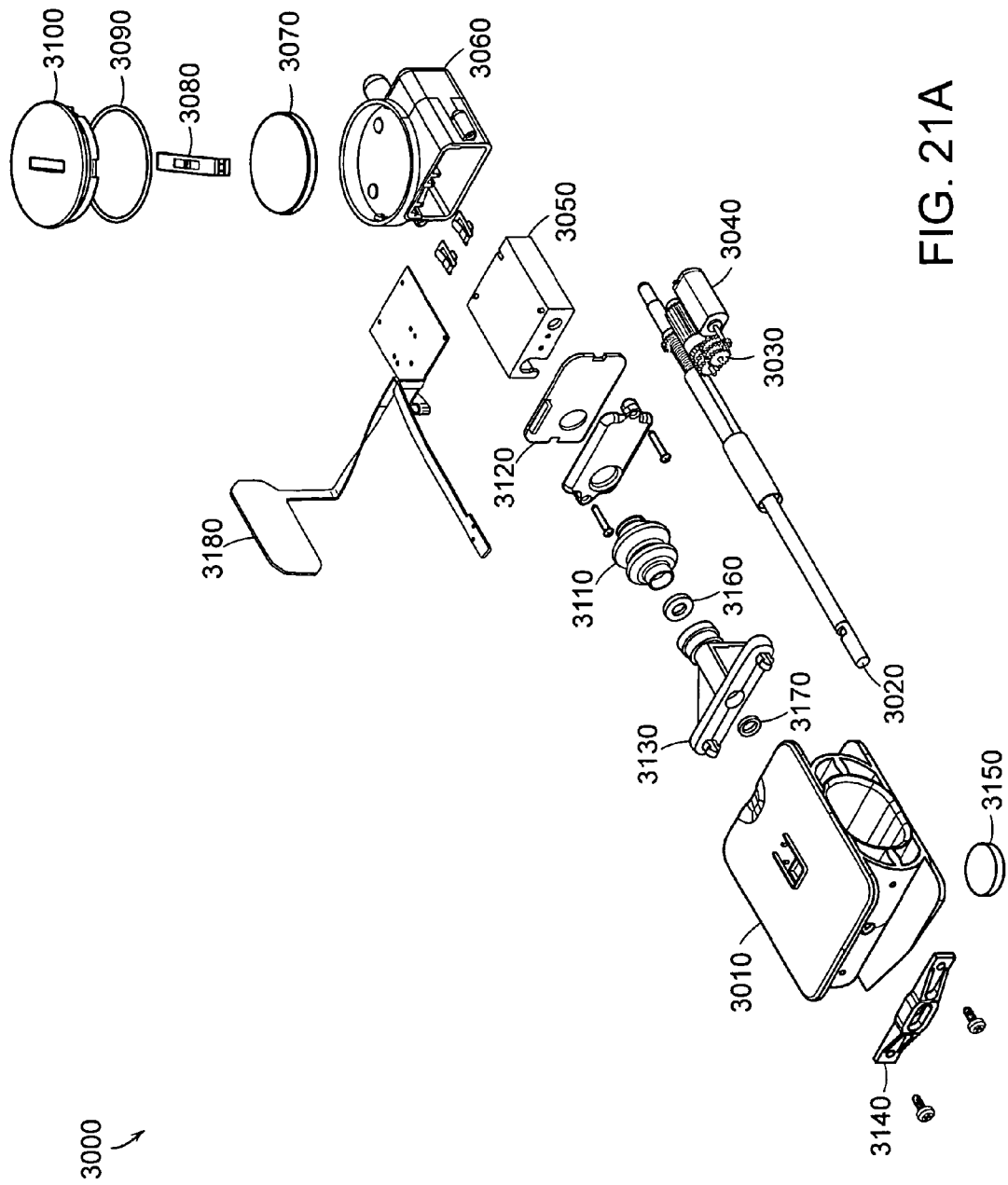
FIG. 21A is an exploded schematic perspective view of a motor and cushioning element for an article of footwear including an intelligent system, in accordance with one embodiment of the invention.

FIG. 21A depicts one example of a motor and cushioning element assembly for an article of footwear including an intelligent system. The arrangement 3000 includes a cushioning element 3010 that is connected by a cable assembly 3020 to a gear arrangement 3030 and a motor 3040. The motor 3040 and gear arrangement 3030 are housed in a gearbox 3050, which is in turn housed within a main housing 3060. The main housing 3060 can hold a battery 3070 in place by, for example, a clip 3080. An O-ring 3090 and battery lid 3100 can then be mounted on the housing 3060 and can provide a waterproof seal over the battery 3070, thus protecting the motor 3040, gearbox 3050, and associated electronics from any damaging moisture or other contaminants, such as, but not limited to, water, mud, dust, and perspiration.

The motor 3040, gearbox 3050, and associated electronics can be further protected from the elements by a gasket 3110 and an end cover 3120. An O-ring 3170 can be placed on a ferrule 3160, covering the cable assembly 3020, to provide a waterproof seal to stop contaminants from entering the gearbox 3050 around the cable assembly 3020. The cable assembly 3020 can then be inserted through the cushioning element 3010 and held in place by crossbars 3130 and 3140. Upon assembling the arrangement 3000, the cushioning element 3010 can be adjusted through signals from a control system connected to the motor 3040 by electrical circuitry 3180. A magnet 3150 can be used, in an example embodiment, to provide a means of obtaining a signal relating to the compression of the cushioning element 3010, as described previously.

Providing O-rings, a gasket, and, end covers for the gearbox 3050, cable assembly 3020, and battery compartment allows the motor and gear assembly to be maintained waterproof. This can be advantageous in protecting the gearbox arrangement from the elements, including water, mud, dust, sand, or other contaminants that an athletic shoe may be exposed to. The waterproof arrangement can also protect the gearbox from moisture generated through perspiration by the shoe's wearer. This protection will result in an extension of the working life of the assembly and a possible increase in the efficiency of the assembly.

Figure 21B:
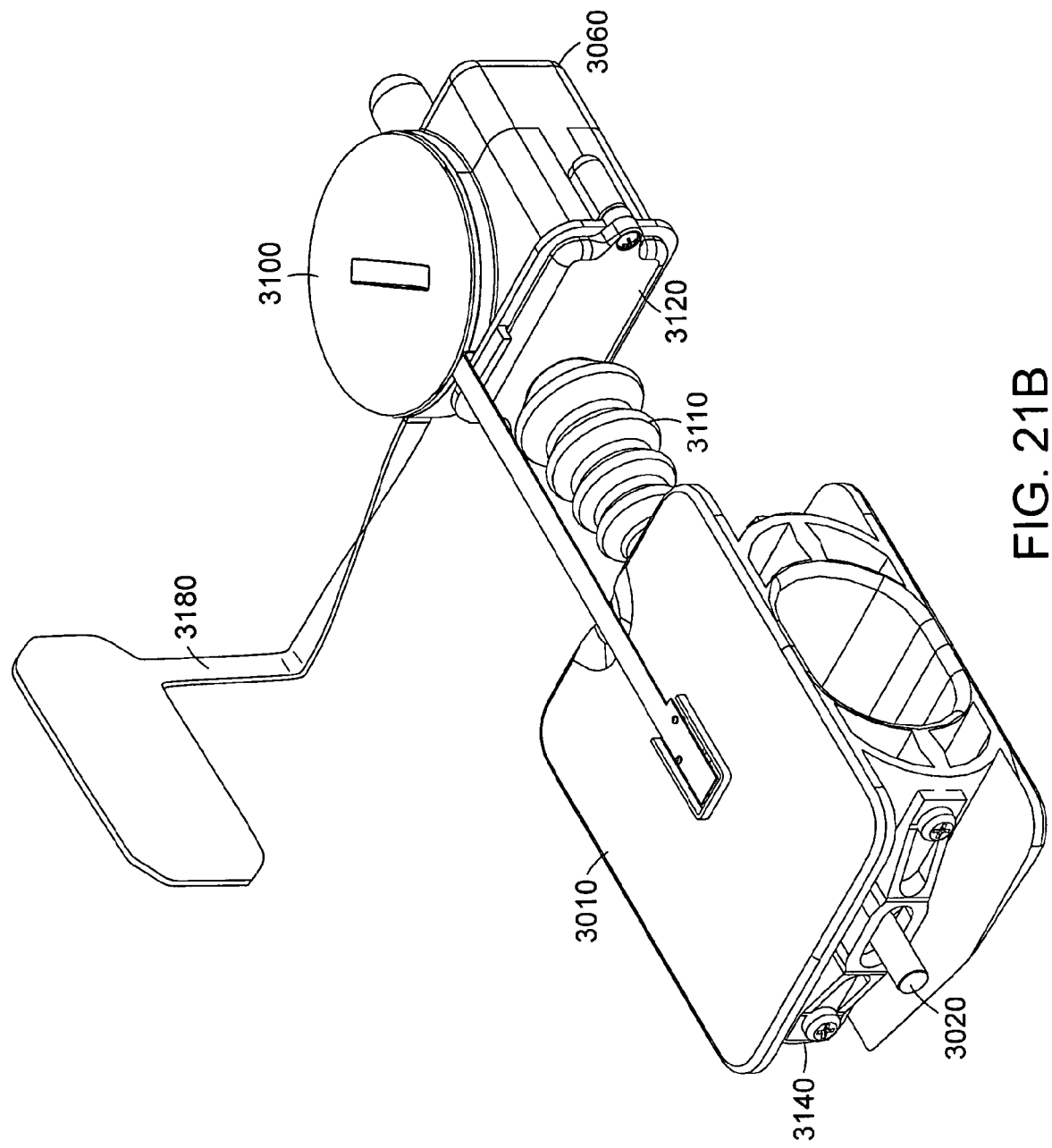
FIG. 21B is a schematic perspective view of the assembled motor and cushioning element of FIG. 21A.

The assembled motor and cushioning element arrangement 3000 can be seen in FIG. 21B. As can be seen, the cable assembly 3020 connects the cushioning element 3010 to the gearbox 3050 housed in the main housing 3060. The gasket 3110 and end covering 3120 provide protection for the gearbox 3050 and the motor 3040. The electrical circuitry 3180 connects to the battery 3070, the motor 3040, and associated electronics within the main housing 3060, and to a sensor embedded within the cushioning element 3010.

Figure 22:
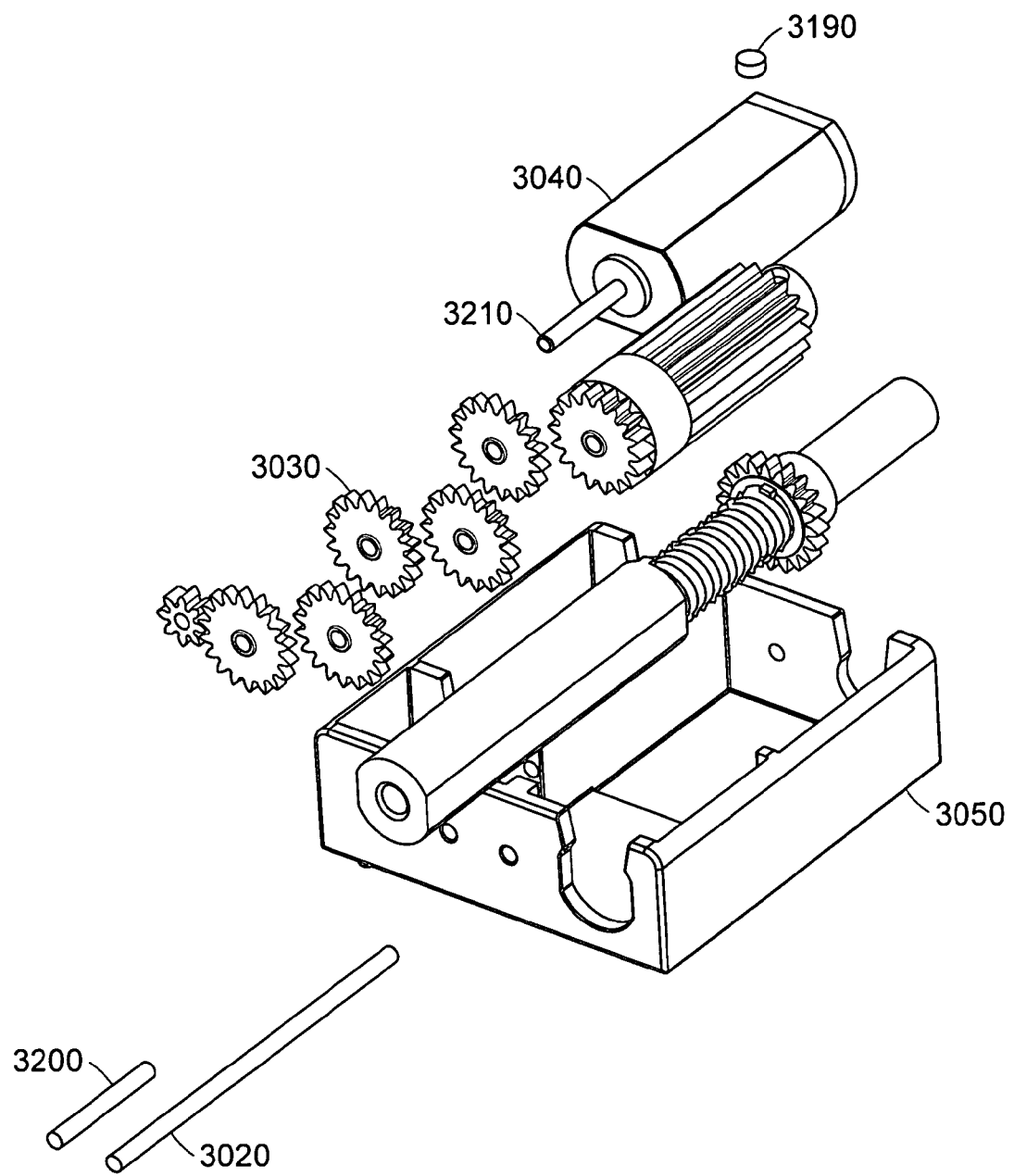
FIG. 22 is an exploded schematic perspective view of a motor and gearbox, in accordance with one embodiment of the invention.

An exploded view of the gearbox 3050, motor 3040, and gear arrangement 3030 can be seen in FIG. 22. Also shown are the main axle 3020, and a secondary axle 3200 for elements of the gear arrangement 3030. A sensing means 3190 can be placed on the motor assembly to provide a means of accurately determining the rotation of the shaft 3210 of the motor 3040, or the rotation of a gear or other rotating component. In one embodiment, the sensing means 3190 can be a magnetic sensor or a magnet attached to a separate sensor located on the electrical circuitry 3180, with the location of the sensing means 3190 corresponding to the location of a magnet positioned on the shaft 3210. This arrangement allows the sensing means 3190 to accurately determine the number of revolutions and/or angular position of the shaft 3210, with the sensing means 3190 recognizing a full rotation of the shaft 3210 every time the magnet placed upon the shaft 3210 passes next to the sensing means 3190. The sensing means 3190 can also be used to determine the rotation of a gear, or other rotating component. In alternative embodiments, different means of determining the rotation of the shaft 3210 can be used, such as, but not limited to, employing a mechanical, electrical, or optical sensor to measure a full or partial rotation of the shaft 3210.

One embodiment of a sole and user input for an article of footwear including an intelligent system is shown in FIG. 23A. In this embodiment, a user input housing 3320 is mounted to a sole unit 3310. The user input housing 3320 provides a means for a wearer to adjust the settings for the cushioning element embedded within the sole 3310. In one embodiment, the user input can include two buttons embedded within the user input housing 3320. These buttons can allow the wearer to input a positive input 3340 and/or a negative input 3330 into the controller of the cushioning element. For example, a positive input 3340 may be used to increase the user preferred stiffness of a cushioning element, while a negative input 330 may be used to decrease the user preferred stiffness of the cushioning element. In one alternative embodiment, the positive input 3340 and negative input 3330 can be used to increase or decrease a threshold compression that determines when the motor and controller automatically adjust the resistance of the cushioning element. In further embodiments, pushing one or more of these buttons may be used to turn the motor and controller on and/or off, set the controller to run a different control algorithm, or adjust another element of the controller and/or motor function.

In a further alternative embodiment, the positive input 3340 and negative input 3330 can be replaced by a single capacitive user interface running between a positive end and negative end of the user input housing 3320. This interface may be, for example, resistance based or capacitance based. In this embodiment, adjustment of the cushioning, or any other user defined input described above, can be enabled by sliding a digit along the user input in either a positive or negative direction, in a manner similar to that used to control touch sensitive computer mousepads or by simply touching the user interface in a certain location such as on the "+" or "−". Further alternative user inputs may include a dial, slider, or other appropriate input mechanism.

FIG. 23B shows an alternative sole and user input for an article of footwear including an intelligent system. In this embodiment, an alternative user input housing 3350 is attached to the sole 3310. In this embodiment, the user input includes a substantially circular or oval capacitive user interface that provides a signal to the control system through movement of a user's digit over the surface of the interface. Here, a positive adjustment of the stiffness can be provided by a clockwise rotation 3370 of the digit over the surface of the interface, while a negative adjustment of the stiffness can be provided by a counter-clockwise rotation 3380 of a user's digit over the interface surface. As described above, the interface can be set to adjust a variety of parameters of the control system and motor, depending upon the requirements of the user or the particular shoe.

Multiple input mechanisms are also contemplated. For example, the circular or oval capacitive user interface can be combined with a further, separate input 3380 to provide the user with greater control of the system and motor. The input 3380 can include any of the user interface mechanisms described above.

Figure 24:
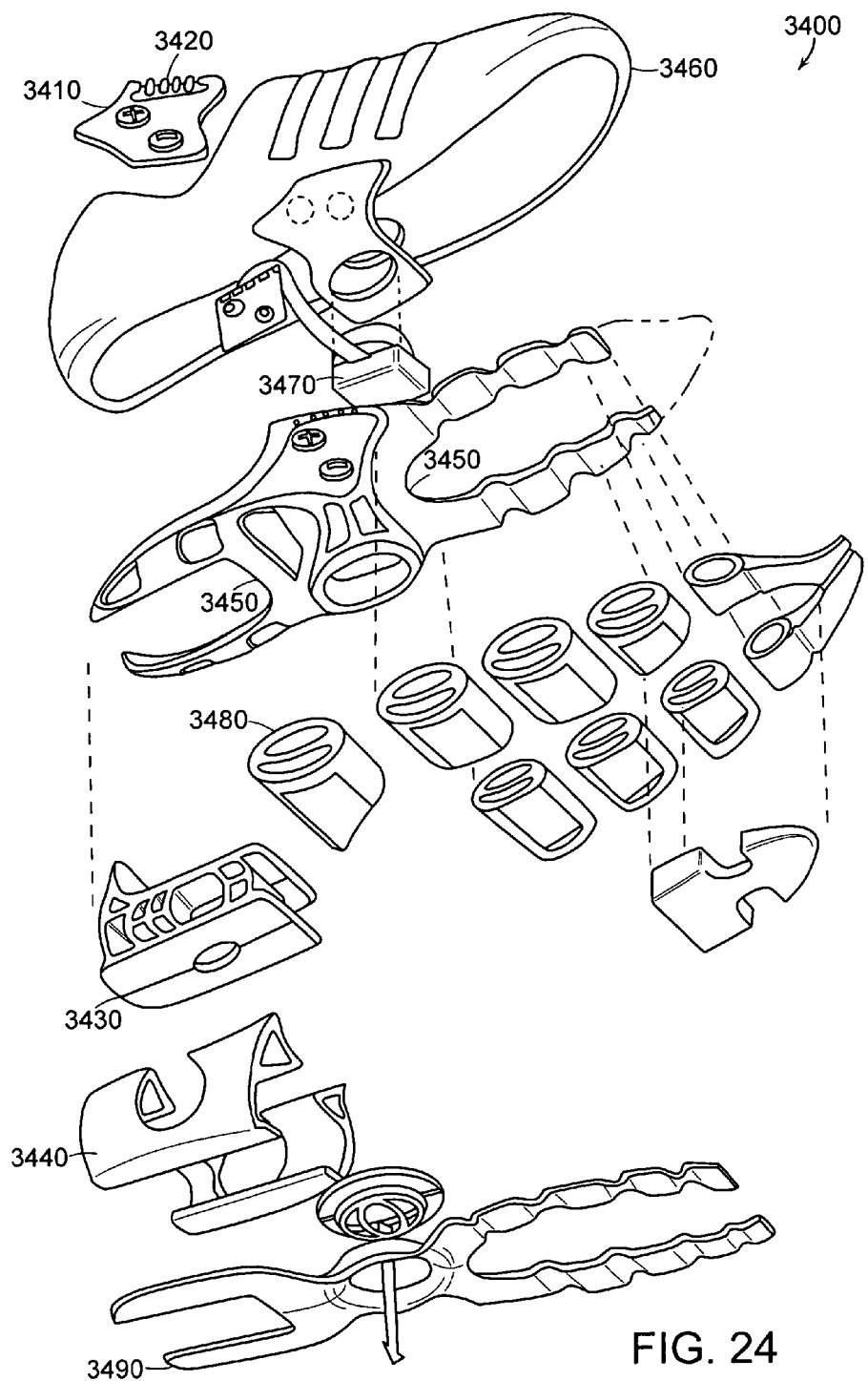
FIG. 24 is an exploded schematic perspective view of an article of footwear including an intelligent system and further including a crash transition element, in accordance with one embodiment of the invention.

An exploded view of an article of footwear 3400 including an intelligent system can be seen in FIG. 24. This embodiment includes a top plate 3450 that is attached to the upper 3460 of the article of footwear 3400 and houses a motor 3470 and other elements of the intelligent system. A number of elliptical structures 3480 are over molded onto the top plate 3450 to provide cushioning to the forefoot area of the sole of the article of footwear 3400. A bottom plate 3490 can then be molded, or otherwise fitted, to the elliptical structures 3480 and/or other sole elements to complete the sole of the article of footwear 3340.

This example embodiment also includes a crash transition element 3430 that is surrounded by two independently tuned guidance structures 3440. The crash transition element 3430 and guidance structures 3440 are located in the heel region of the article of footwear. In one embodiment, the crash transition element 3430 is a structural cushioning element, the compressibility of which can be adjusted by the intelligent system 106. Alternatively, the crash transition element 3430 can be a structural element that can be adjusted to affect other performance characteristics of the shoe. Further, the crash transition element 3430 can be configured to respond rapidly to a signal from the intelligent system 106.

This embodiment includes a further alternative user input interface 3410, including two buttons providing a positive and negative user input. The user input interface 3410 can also include a series of LEDs 3420, what can provide the user with a visual indication of the setting of the cushioning control system. This user input interface can be replaced, in alternative embodiments, by any of the user inputs described previously.

Figure 25A:
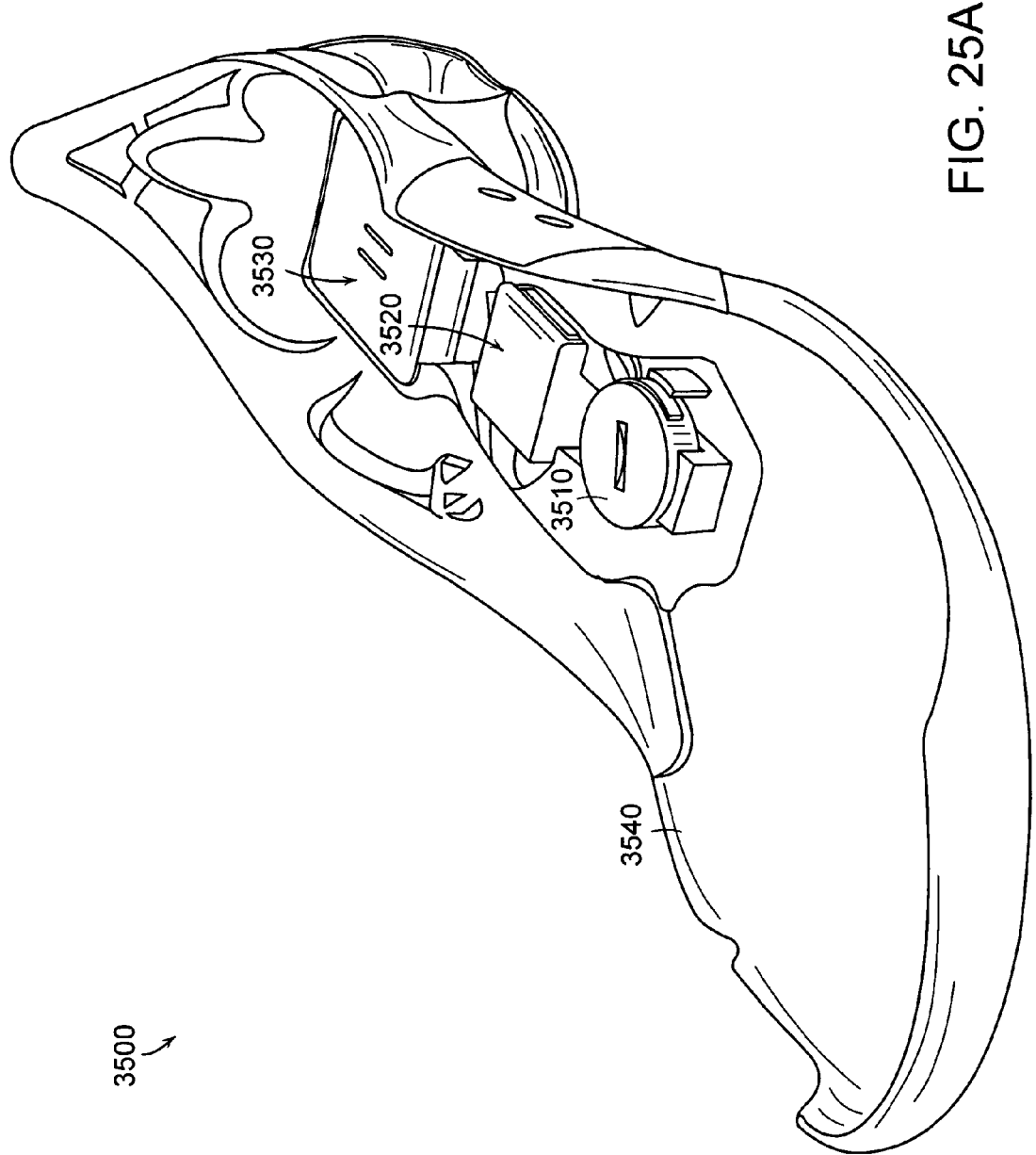
FIG. 25A is a schematic perspective view of a sole for an article of footwear including an intelligent system, in accordance with one embodiment of the invention.

FIG. 25A shows a partially exploded schematic perspective view of the sole of an article of footwear including an intelligent system, for use with a basketball shoe. In this embodiment, the sole 3500 includes a battery 3510, a motor and gear assembly 3520, and a cushioning element 3530, all embedded within a molded sole 3540. In this configuration, the battery 3510 is placed in front of the motor and gear assembly 3520, rather than on top of the motor assembly. This placement of the battery 3510 can decrease the overall height of the system, allowing the control system to be embedded in thinner soles. This can be advantageous in shoes such as those required for basketball, indoor soccer, squash, or other aerobic activities, where it is preferable to have a thinner sole in order to place the wearer's foot closer to the ground to facilitate turning, jumping, landing, cutting, starting and stopping rapidly, and other movements with such activities.

In this configuration, the battery 3510 is placed in front of the motor and gear assembly 3520 in the midsole region of the molded sole 3540. It may be advantageous to place the battery in this region as in many activities it is subject to lower compressive loads than the heel and forefoot regions of the sole. The battery compartment can be accessed through the upper side of the molded sole 3540 in order to insert and replace a battery 3510 when required. In alternative embodiments, the battery compartment can be accessed through the bottom or a side of the molded sole 3540.

In alternative embodiments of the invention, the battery 3510 can be placed at a number of different locations within the sole or upper of an article of footwear including an intelligent system, depending upon the specific shoe design and user requirements. For example, compartments for the battery, or batteries, can be placed at locations including, but not limited to, the forefoot or heel portions of the sole, on the side of the sole, on the rear of the shoe at the heel, or at a location on the upper of the shoe.

FIG. 25B is an exploded view of the sole of FIG. 25A. The sole 3500 includes an outsole 3550, a support element 3560, a lower support plate 3570, a rearfoot portion 3580, an upper support plate 3590, and a midsole 3600. An adjustable expansion element 3610, a motor 3620, and a power source 3630 are embedded within the sole 3500 between the lower support plate 3570 and the midsole 3600. The power source 3630 can be a battery, or any other appropriate means for providing power to the motor 3620. A user interface 3640 can be attached to a side of the assembled sole 3500 to provide a user with means of adjusting the functions of the expansion element 3610 and motor 3620 assembly. A sensor 3650 and sensor cover 3660 can be located below the expansion element 3610.

Upon construction, the motor 3620 and the power source 3630 are inserted into a cavity 3670 in the midsole 3600. In certain embodiments, access to the power source 3630 can be gained through an opening in the upper surface of the midsole 3600, while in other embodiments the power source 3630 can be accessed through on opening on the bottom or side of the sole 3500. In further embodiments, one or more elements of the sole 3500, such as the support element 3560, the lower support plate 3570, or the upper support plate 3590, may not be required, depending upon the specific style of shoe being constructed.

Figure 26:
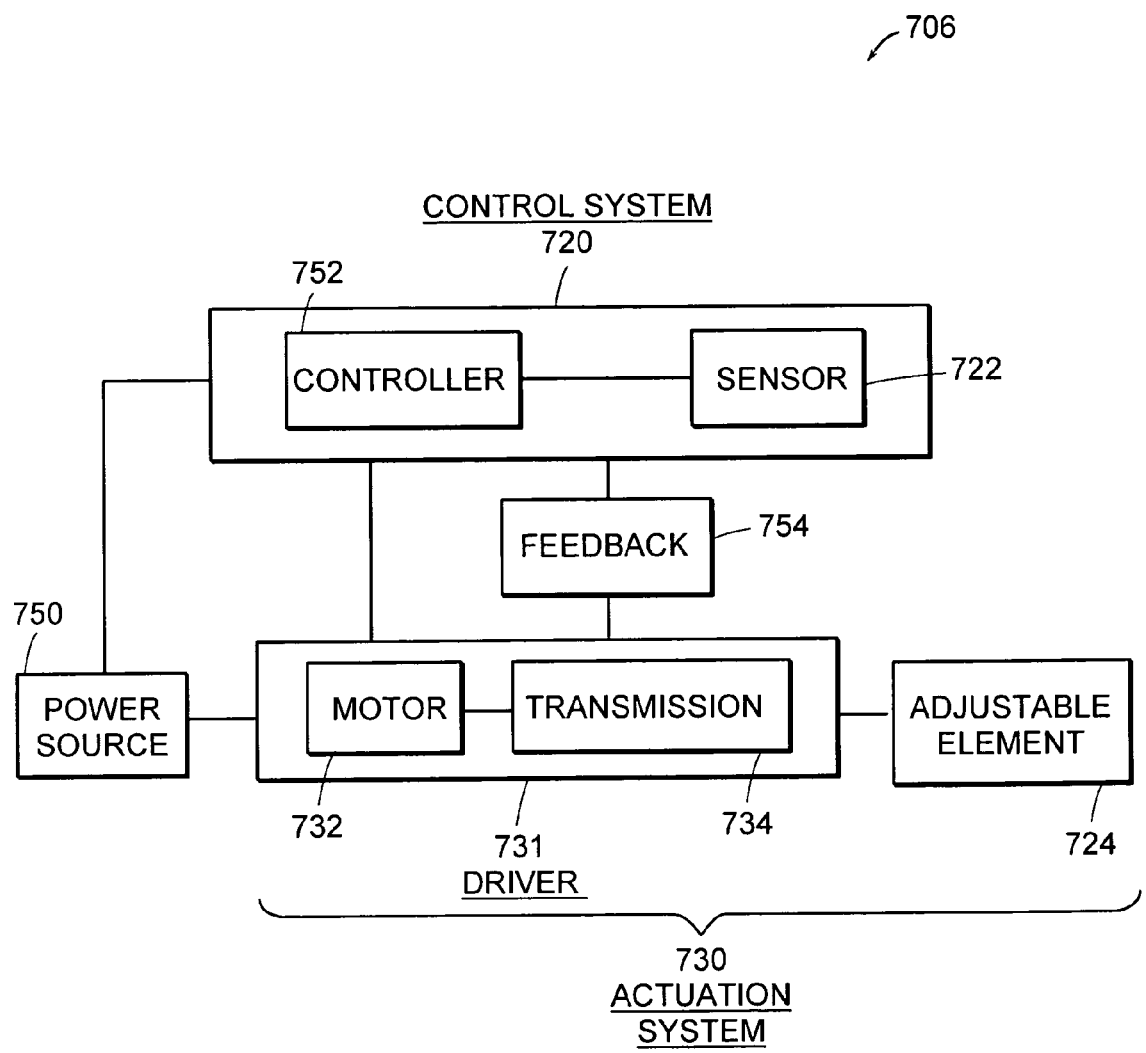
FIG. 26 is a block diagram of an intelligent system in accordance with the invention.

A block diagram of one embodiment of an intelligent system 706 is shown in FIG. 26. The intelligent system 706 includes a power source 750 electrically coupled to a control system 720 and an actuation system 730. The control system 720 includes a controller 752, for example one or more microprocessors, and a sensor 722. The sensor may be a proximity-type sensor and magnet arrangement. In one embodiment, the controller 152 is a microcontroller such as the PICMicro® microcontroller manufactured by Microchip Technology Incorporated of Chandler, Ariz. In another embodiment, the controller 752 is a microcontroller manufactured by Cypress Semiconductor Corporation. The actuation system 730 includes a driver 731, including a motor 732 and a transmission element 734, and an adjustable element 724. The driver 731 and control system 720 are in electrical communication. The adjustable element 724 is coupled to the driver 731.

Optionally, the actuation system 730 could include a feedback system 754 coupled to or as part of the control system 720. The feedback system 754 may indicate the position of the adjustable element 724. For example, the feedback system 754 can count the number of turns of the motor 732 or the position of the limiter 728 (not shown). The feedback system 754 could be, for example, a linear potentiometer, an inductor, a linear transducer, or an infrared diode pair.

Figure 27:
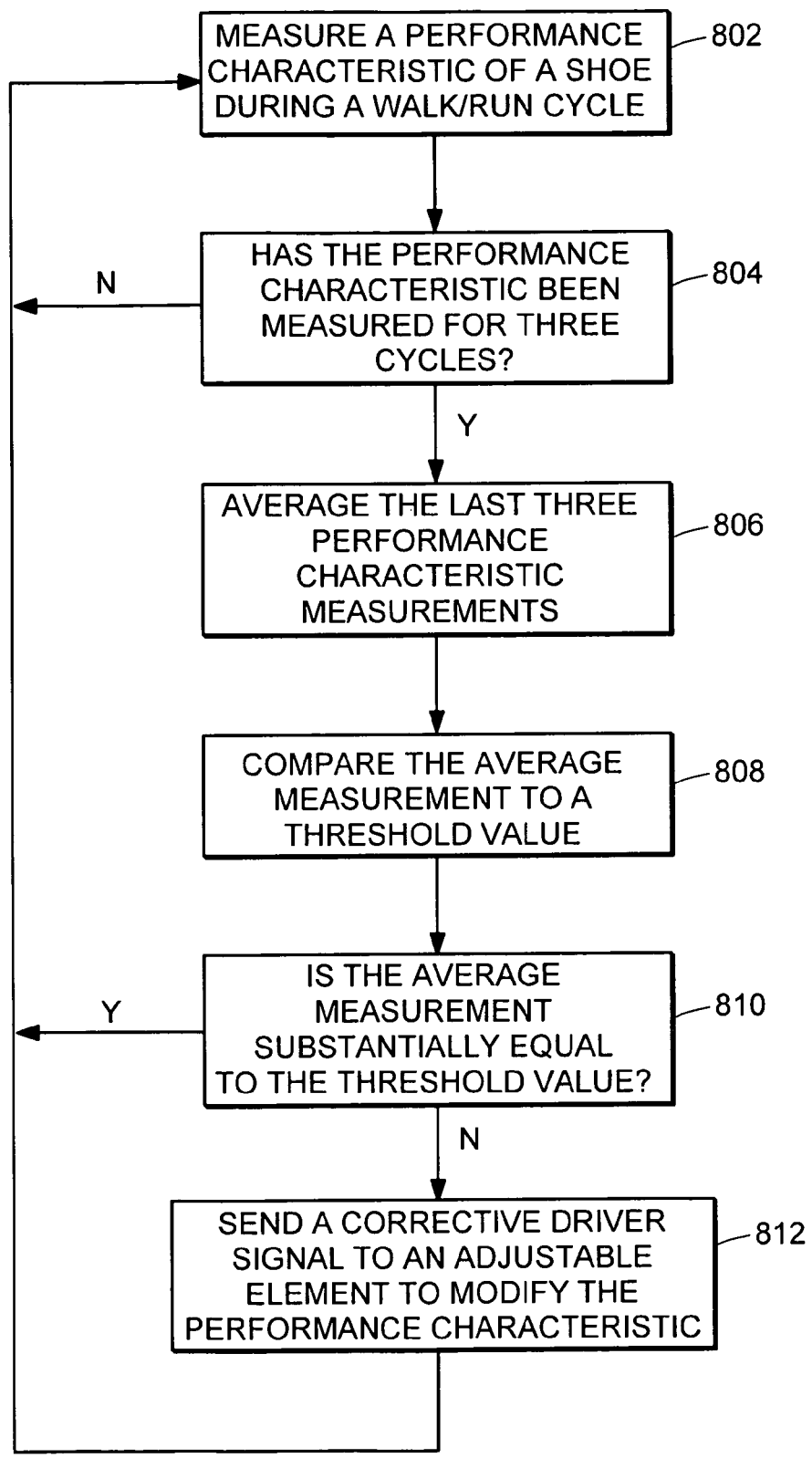
FIG. 27 is a flow chart depicting one mode of operation of the intelligent system of FIG. 1.

FIG. 27 depicts one possible algorithm for use with the intelligent system 106. The intelligent system 106 measures a performance characteristic of a shoe during a walk/run cycle. Before the system 106 begins to operate, the system 106 may run a calibration procedure after first being energized or after first contacting the ground surface. For example, the system 106 may actuate the adjustable element 124 to determine the position of the limiter 128 and/or to verify the range of the limiter 128, i.e., fully open or fully closed. During operation, the system 106 measures a performance characteristic of the shoe (step 802). In one embodiment, the measurement rate is about 300 Hz to about 60 KHz. The control system 120 determines if the performance characteristic has been measured at least three times (step 804) or some other predetermined number. If not, the system 106 repeats step 802 by taking additional measurements of the performance characteristic until step 804 is satisfied. After three measurements have been taken, the system 106 averages the last three performance characteristic measurements (step 806). The system 106 then compares the average performance characteristic measurement to a threshold value (step 808). At step 810, the system 106 determines if the average performance characteristic measurement is substantially equal to the threshold value. If the average performance characteristic measurement is substantially equal to the threshold value, the system 106 returns to step 802 to take another performance characteristic measurement. If the average performance characteristic measurement is not substantially equal to the threshold value, the system 106 sends a corrective driver signal to the adjustable element 124 to modify the performance characteristic of the shoe. The intelligent system 106 then repeats the entire operation until the threshold value is reached and for as long as the wearer continues to use the shoes. In one embodiment, the system 106 only makes incremental changes to the performance characteristic so that the wearer does not sense the gradual adjustment of the shoe and does not have to adapt to the changing performance characteristic. In other words, the system 106 adapts the shoe to the wearer, and does not require the wearer to adapt to the shoe.

Generally, in a particular application, the system 106 utilizes an optimal midsole compression threshold (target zone) that has been defined through testing for a preferred cushioning level. The system 106 measures the compression of the midsole 110 on every step, averaging the most recent three steps. If the average is larger than the threshold then the midsole 110 has over-compressed. In this situation, the system 106 signals the driver 131 to adjust the adjustable element 124 in a hardness direction. If the average is smaller than the threshold, then the midsole 110 has under-compressed. In this situation, the system 106 signals the driver 131 to adjust the adjustable element in a softness direction. This process continues until the measurements are within the target threshold of the system. This target threshold can be modified by the user to be harder or softer. This change in threshold is an offset from the preset settings. All of the above algorithm is computed by the control system 120.

In this particular application, the overall height of the midsole 110 and adjustable element 124 is about 20 mm. During testing, it has been determined that an optimal range of compression of the midsole 110 is about 9 mm to about 12 mm, regardless of the hardness of the midsole 110. In one embodiment, the limiter 128 has an adjustment range that corresponds to about 10 mm of vertical compression. The limiter 128, in one embodiment, has a resolution of less than or equal to about 0.5 mm. In an embodiment of the system 106 with user inputs, the wearer may vary the compression range to be, for example, about 8 mm to about 11 mm or about 10 mm to about 13 mm. Naturally, ranges of greater than 3 mm and lower or higher range limits are contemplated and within the scope of the invention.

During running, the wearer's foot goes through a stride cycle that includes a flight phase (foot in the air) and a stance phase (foot in contact with the ground). In a typical stride cycle, the flight phase accounts for about ⅔ of the stride cycle. During the stance phase, the wearer's body is normally adapting to the ground contact. In a particular embodiment of the invention, all measurements are taken during the stance phase and all adjustments are made during the flight phase. Adjustments are made during the flight phase, because the shoe and, therefore, the adjustable element are in an unloaded state, thereby requiring significantly less power to adjust than when in a loaded state. In most embodiments, the shoe is configured such that the motor does not move the adjustable element; therefore lower motor loads are required to set the range of the adjustable element. In the embodiments depicted in FIGS. 39, 40, and 41, however, the adjustable element does move, as described in greater detail hereinbelow.

During operation, the system 106 senses that the shoe has made contact with the ground. As the shoe engages the ground, the sole 104 compresses and the sensor 122 senses a change in the magnetic field of the magnet 123. The system 106 determines that the shoe is in contact with the ground when the system 106 senses a change in the magnetic field equal to about 2 mm in compression. It is also at this time that the system 106 turns off the power to the actuation system 130 to conserve power. During the stance phase, the system 106 senses a maximum change in the magnetic field and converts that measurement into a maximum amount of compression. In alternative embodiments, the system 106 may also measure the length of the stance phase to determine other performance characteristics of the shoe, for example velocity, acceleration, and jerk.

If the maximum amount of compression is greater than 12 mm, then the sole 104 has over-compressed, and if the maximum amount of compression is less than 9 mm, then the sole 104 has under-compressed. For example, if the maximum compression is 16 mm, then the sole 104 has over-compressed and the control system 120 sends a signal to the actuation system 130 to make the adjustable element 124 firmer. The actuation system 130 operates when the shoe is in the flight phase, i.e., less than 2 mm of compression. Once the system 106 senses that the compression is within the threshold range, the system 106 continues to monitor the performance characteristic of the shoe, but does not further operate the actuation system 130 and the adjustable element 124. In this way, power is conserved.

In alternative embodiments, the intelligent system 106 can use additional performance characteristics alone or in combination with the optimal midsole compression characteristic described above. For example, the system 106 can measure, in addition to compression, time to peak compression, time to recovery, and the time of the flight phase. These variables can be used to determine an optimum setting for the user, while accounting for external elements such as ground hardness, incline, and speed. Time to peak compression is described as the amount of time that it takes from heel strike to the maximum compression of the sole while accounting for surface changes. It may be advantageous to use the area under a time versus compression curve to determine the optimum compression setting. This is in effect a measure of the energy absorbed by the shoe. In addition, the time of the flight phase (described above) can contribute to the determination of the optimum setting. The stride frequency of the user can be calculated from this variable. In turn, stride frequency can be used to determine changes in speed and to differentiate between uphill and downhill motion.

Figure 28:
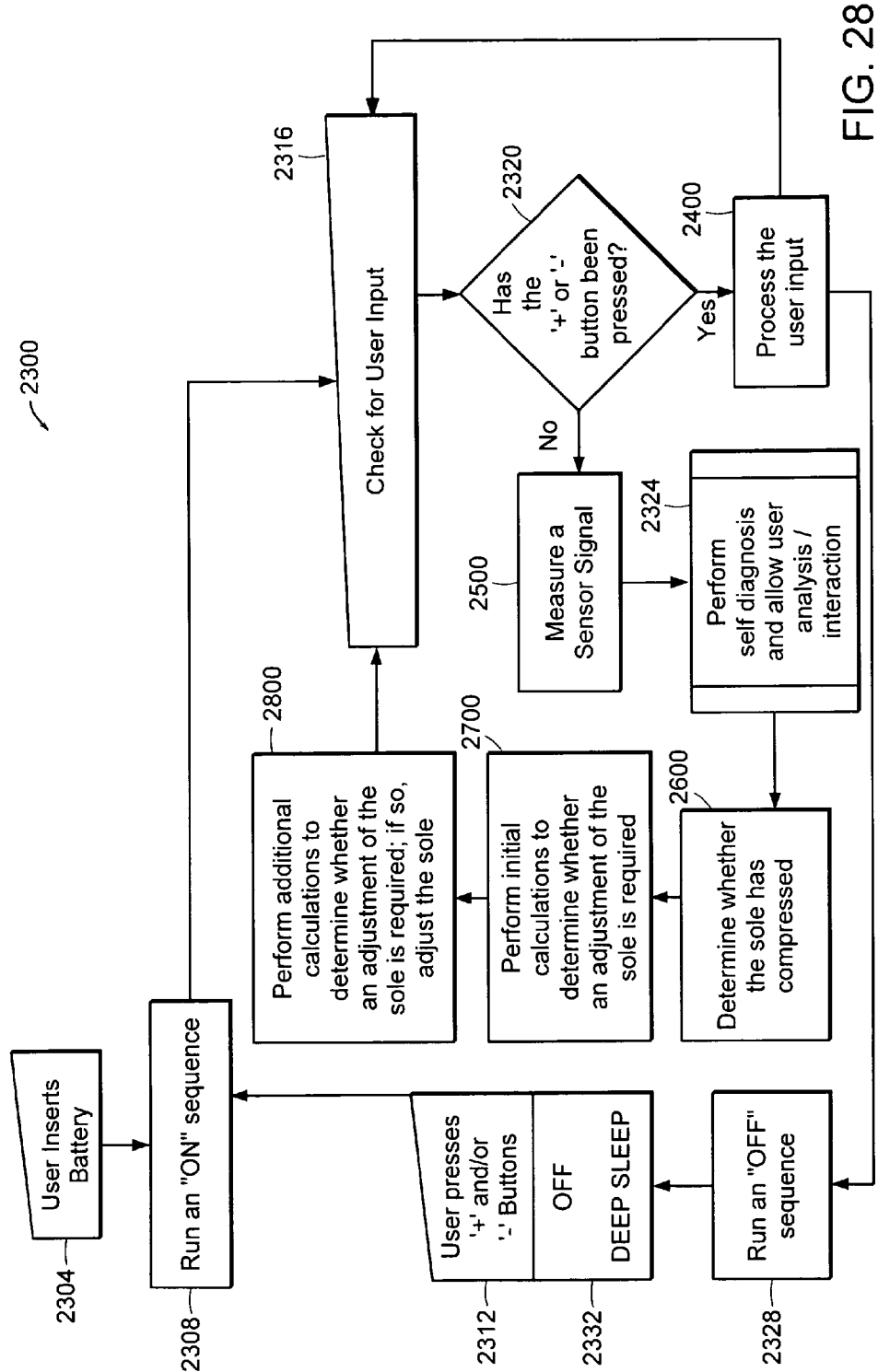
FIG. 28 is a flow chart depicting an alternative mode of operation of the intelligent system of FIG. 1.

FIG. 28 depicts another possible algorithm that may be performed by the intelligent system 106. In particular, FIG. 28 illustrates one embodiment of a method 2300 for modifying a performance characteristic of the article of footwear 100 during use. At step 2500 of the method 2300, the intelligent system 106 measures a sensor signal from the sensor 122. The intelligent system 106 then determines, at step 2600, whether the sole 104 has compressed. Alternatively or additionally, the system 106 can determine if the user has engaged in any of various activities, for example running, cutting, jumping, or landing, to which the system 106 can adjust a performance characteristic in response thereto. Upon determining that the sole 104 has compressed, the intelligent system 106 performs initial calculations, at step 2700, to determine whether an adjustment of the sole 104 is required. At step 2800, the intelligent system 106 performs additional calculations to determine further or alternatively whether an adjustment of the sole 104 is required. If an adjustment of the sole 104 is required, the intelligent system 106 also adjusts the sole 104 at step 2800. FIGS. 25, 26, 27, and 28, which follow, describe methods for implementing the steps 2500, 2600, 2700, and 2800, respectively, of the method 2300.

The method 2300 begins by providing power to the intelligent system 106. For example, a battery may act as the power source 150 and may be installed in the intelligent system 106 at step 2304. Once the battery is installed in the intelligent system 106, the intelligent system 106 may run an "ON" sequence at step 2308. For example, the intelligent system 106 may light the electro-luminescent elements of the indicator 506 in a manner that signals to a user of the article of footwear 100 that the intelligent system 106 is active. Where the battery is already installed in the intelligent system 106, but a user of the article of footwear 100 has previously turned the intelligent system 106 off (as described below), the user may turn the intelligent system 106 on and activate the "ON" sequence by pressing, for example, one or more of the user-input buttons 502, 504 at step 2312.

Figure 29:
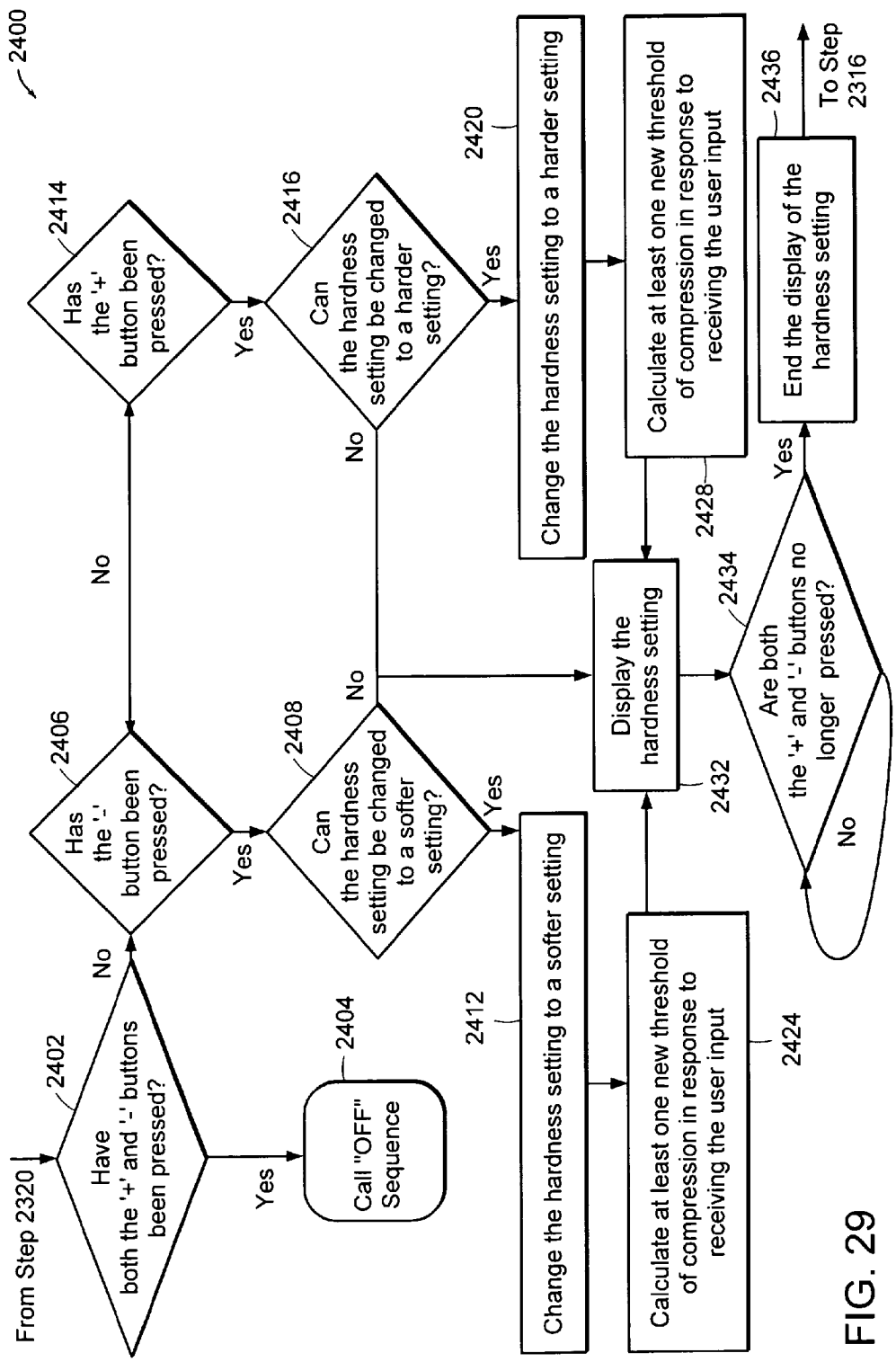
FIG. 29 is a flow chart of a method for processing user inputs using the intelligent system of FIG. 1 in accordance with one embodiment of the invention.

Once the intelligent system 106 is on, the intelligent system 106 may check for user input at step 2316. In the embodiments depicted in FIGS. 28-33, the user indicates a desire to increase hardness of the sole 104 by pressing the "+" button 502, and a desire to decrease the hardness of the sole 104 (i.e., increase the softness of the sole 104) by pressing the "−" button 504. If user input is received from a user of the article of footwear 100, as determined at step 2320, the intelligent system 106 processes the user input at step 2400. FIG. 29, which follows, describes a method implementing the step 2400 of the method 2300. If user input is not received, the intelligent system 106 measures the sensor signal from the sensor 122 at step 2500.

Optionally, the method 2300 may include a self diagnostic and user analysis/interaction step 2324. More specifically, at step 2324, the intelligent system 106 may diagnose itself by checking several parameters of the intelligent system 106 described herein, including, but not limited to, the sensor condition and/or output, the battery strength, the motor direction, the condition of the voltage reference that may be used in step 2500, and the presence or absence of user-input from buttons 502, 504. Moreover, at step 2324, a user of the article of footwear 100 may read data from the intelligent system 106 or perform other functions. In one embodiment, a special key is used to access the intelligent system 106. For example, armed with their own special keys, retailers could read certain data, manufacturers could read other data useful in, for example, preparing a failure report, and customers could be allowed to manually adjust the intelligent system 106 by, for example, moving the motor 132. Additionally or alternatively, the intelligent system 106 may be able to track or monitor the athletic performance of a wearer of the article of footwear 100, such as, for example, the distance traveled by the wearer, the wearer's pace, and/or the wearer's location. In such an embodiment, this information may be accessed at step 2324.

In one embodiment, the intelligent system 106 cycles through the steps of the method 2300 by following the directions of the arrows indicated in FIG. 28, with each particular step along the way being performed or not depending on the value of certain parameters. In addition, in one particular embodiment, the intelligent system 106 cycles through steps 2316, 2320, 2500, 2324, 2600, 2700, and 2800 at a rate between about 300 Hz and about 400 Hz.

In some embodiments, a microcontroller of the intelligent system 106 performs many of the steps described with respect to FIGS. 28-33. The microcontroller may include, for example, a receiver that is configured to receive a first signal representing an output from the sensor 122, a determination module that is configured to determine whether the sole 104 has compressed and to determine whether adjustment of the sole 104 is required, and a transmitter that is configured to transmit a second signal for adjusting the sole 104.

In greater detail, if the intelligent system 106 determines, at step 2320, that a user has entered input, the intelligent system 106 processes such user input at step 2400. Referring to FIG. 29, which depicts one embodiment of a method 2400 for processing the user input, if the user has pressed both the "+" button 502 and the "−" button 504 at the same time, as determined at step 2402, the intelligent system 106 calls the "OFF" sequence at step 2404. Referring back to FIG. 28, the intelligent system 106 then runs the "OFF" sequence at step 2328. In one embodiment, in running the "OFF" sequence, the intelligent system 106 lights the electro-luminescent elements of the indicator 506 in a manner that signals to a user of the article of footwear 100 that the intelligent system 106 is being turned off. The intelligent system 106 may then enter an "OFF" or "DEEP SLEEP" mode at step 2332 until it is again activated by the user at step 2312.

Returning to FIG. 29, the sole 104 of the article of footwear 100 may include a number of hardness settings, and the intelligent system 106 may be configured to change the hardness setting for the sole 104 in response to receiving the user input. It should be noted, however, that while the hardness setting for the sole 104 is a user adjustable parameter, changing the hardness setting for the sole 104 does not necessarily lead to an adjustment of the sole 104 itself (e.g., a softening or hardening of the sole 104). Whether or not the sole 104 is itself adjusted depends in part on the hardness setting, but also on many other variables, and is not determined until steps 2700 and 2800 described below. It should also be noted that the values of the constants, settings, and other parameters can be varied as necessary to suit a particular application of the shoe, for example for running or basketball.

In one embodiment, the number of hardness settings for the sole 104 is between five and 20. If the user has pressed only the "−" button 504 (decided at step 2406), the intelligent system 106 determines, at step 2408, whether the current hardness setting for the sole 104 can be changed to a softer setting. If so (i.e., if the hardness setting for the sole 104 is not currently set to its softest setting), the intelligent system 106 changes the hardness setting for the sole 104 to a softer setting at step 2412. Similarly, if the user has pressed only the "+" button 502 (decided at step 2414), the intelligent system 106 determines, at step 2416, whether the current hardness setting for the sole 104 can be changed to a harder setting. If so (i.e., if the hardness setting for the sole 104 is not currently set to its hardest setting), the intelligent system 106 changes the hardness setting for the sole 104 to a harder setting at step 2420.

Following the adjustment of the hardness setting for the sole 104 at either step 2412 or step 2420, the intelligent system 106 calculates, either at step 2424 or at step 2428, at least one new threshold of compression in response to receiving the user input. In one embodiment, the intelligent system 106 calculates both a new lower threshold of compression and a new upper threshold of compression. Each new threshold of compression may be calculated by taking into account, for example, a previous value for that threshold of compression, the new hardness setting for the sole 104 (determined either at step 2412 or at step 2420), and one or more constants. In one embodiment, each threshold of compression is used in determining, at step 2800, whether the adjustment of the sole 104 is required.

Once step 2424 or step 2428 is complete, or if it was determined either at step 2408 or at step 2416 that the hardness setting for the sole 104 could not be changed, the intelligent system 106 displays the new (current) hardness setting for the sole 104 at step 2432. In one embodiment, the intelligent system 106 displays the new (current) hardness setting for the sole 104 by activating at least one electro-luminescent element of the indicator 506. Once the intelligent system 106 is sure that both the "+" and "−" buttons 502, 504 are no longer pressed (determined at step 2434), the intelligent system 106 ends, at step 2436, the display of the new (current) hardness setting by, for example, deactivating (e.g., fading) the one or more activated electro-luminescent elements of the indicator 506. The intelligent system 106 then returns to step 2316 of FIG. 28.

Figure 30:
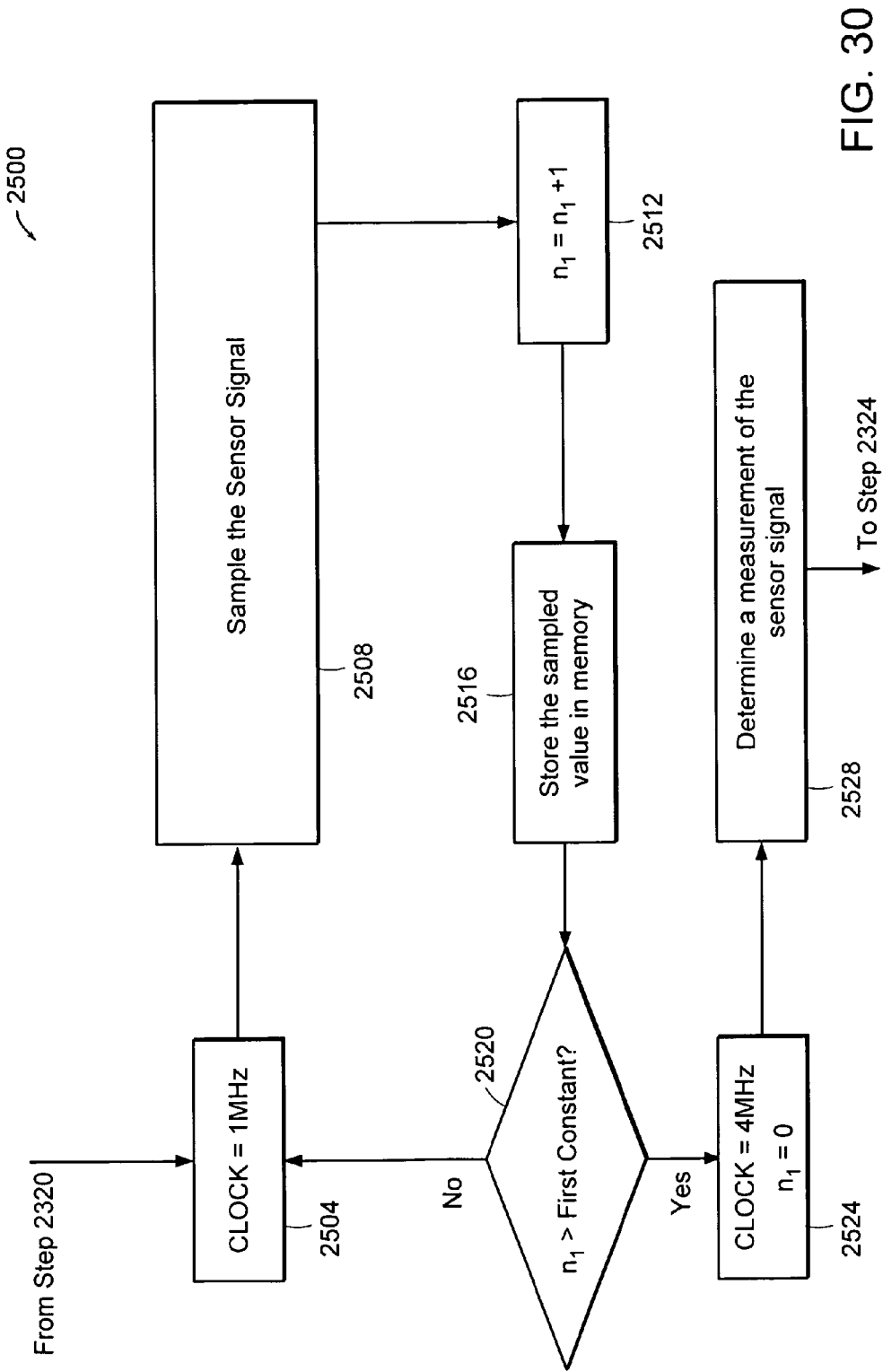
FIG. 30 is a flow chart of a method for measuring a sensor signal using the intelligent system of FIG. 1 in accordance with one embodiment of the invention.

Returning to FIG. 28, if the intelligent system 106 determines, at step 2320, that a user has not entered an input, the intelligent system 106 measures the sensor signal from the sensor 122 at step 2500. Referring to FIG. 30, which depicts one embodiment of a method 2500 for measuring the sensor signal, the intelligent system 106 may first set, at step 2504, the instruction clock (e.g., slow down the instruction clock) of the microcontroller that implements many of the steps in the methods of FIGS. 28-33 to, for example, 1 MHz. The microcontroller's instruction clock is set to 1 MHz to conserve battery power and does not relate to the rate at which the signal from the sensor 122 is sampled. Alternatively, the microcontroller's instruction clock may be set to a different frequency to conserve battery power.

Once the microcontroller's instruction clock is set, the signal from the sensor 122 is sampled at step 2508. In one embodiment, the sensor 122 is a hall effect sensor that measures a magnetic field and that outputs an analog voltage representative of the strength of the magnetic field. Accordingly, in one embodiment of step 2508, the analog voltage is sampled, compared to a voltage reference, and converted to a digital value using an A/D converter. In the embodiments described herein, a smaller digital value represents a stronger magnetic field and, therefore, a greater amount of compression in the sole 104.

An external RC timer, regulated voltage with or without a divider, or other external devices can be used in the intelligent system 106 to supply the voltage reference. Alternatively, the voltage reference may be provided by configuration of the microcontroller. Taking an A/D reading off the supply voltage to the sensor enables the microcontroller to account for any slight deviations from the desired voltage since the output from the sensor is often ratiometric. In one embodiment, the voltage reference can run from 1 V to 3 V and can help to increase the resolution of the signal. In alternative embodiments, the minimum and maximum voltages can be anywhere from 0.1 V to 10 V.

In a particular implementation of step 2508, the sensor 122, which in one embodiment has the greatest settling time, is turned on first. The A/D converter, which in one embodiment has the second greatest settling time, is then turned on. Following that, the electrical devices implementing the voltage reference are turned on. The analog voltage output by the sensor 122 is then sampled, compared to the voltage reference, and converted to a digital value using an A/D converter. The sensor 122 is then turned off to conserve energy. Following that, the electrical devices implementing the voltage reference are turned off to also conserve energy and, lastly, the A/D converter is turned off to conserve energy. In other embodiments, the sensor 122, the A/D converter, and the electrical devices implementing the voltage reference may be turned on and/or off in other orders, and may even be turned on and/or off substantially simultaneously.

Once the signal from the sensor 122 has been sampled at step 2508, a counter "$n_1$", which is initially set to zero and represents the number of samples taken, is incremented at step 2512. The digital value representative of the strength of the magnetic field sampled at step 2508 is then stored in the microcontroller's memory at step 2516.

At step 2520, the counter "$n_1$" is compared to a first constant to determine whether the number of samples taken is greater than the first constant. If so, the microcontroller's instruction clock is reset to, for example, 4 MHz and the counter "$n_1$" is reset to zero at step 2524. Otherwise, steps 2504, 2508, 2512, 2516, and 2520 are repeated. By setting the first constant to a value greater than zero, the intelligent system 106 is sure to sample the sensor signal a plurality of times. Typically, the value of the first constant is between two and ten.

At step 2528, a measurement of the sensor signal is determined. In one embodiment, the measurement of the sensor signal is determined by calculating the average of the plurality of samples of the sensor signal taken in repeating step 2508. In another embodiment, the measurement of the sensor signal is determined by, for example, averaging a subset of the plurality of samples of the sensor signal taken in repeating step 2508. In one particular embodiment, the lowest and highest sampled values of the sensor signal are discarded, and the remaining sampled values of the sensor signal are averaged to determine the measurement of the sensor signal. Once the measurement of the sensor signal is determined at step 2528, the self diagnostic and user analysis/interaction step 2324 may be performed, as necessary. As illustrated in FIG. 28, the intelligent system 106 then moves on to step 2600.

Figure 31:
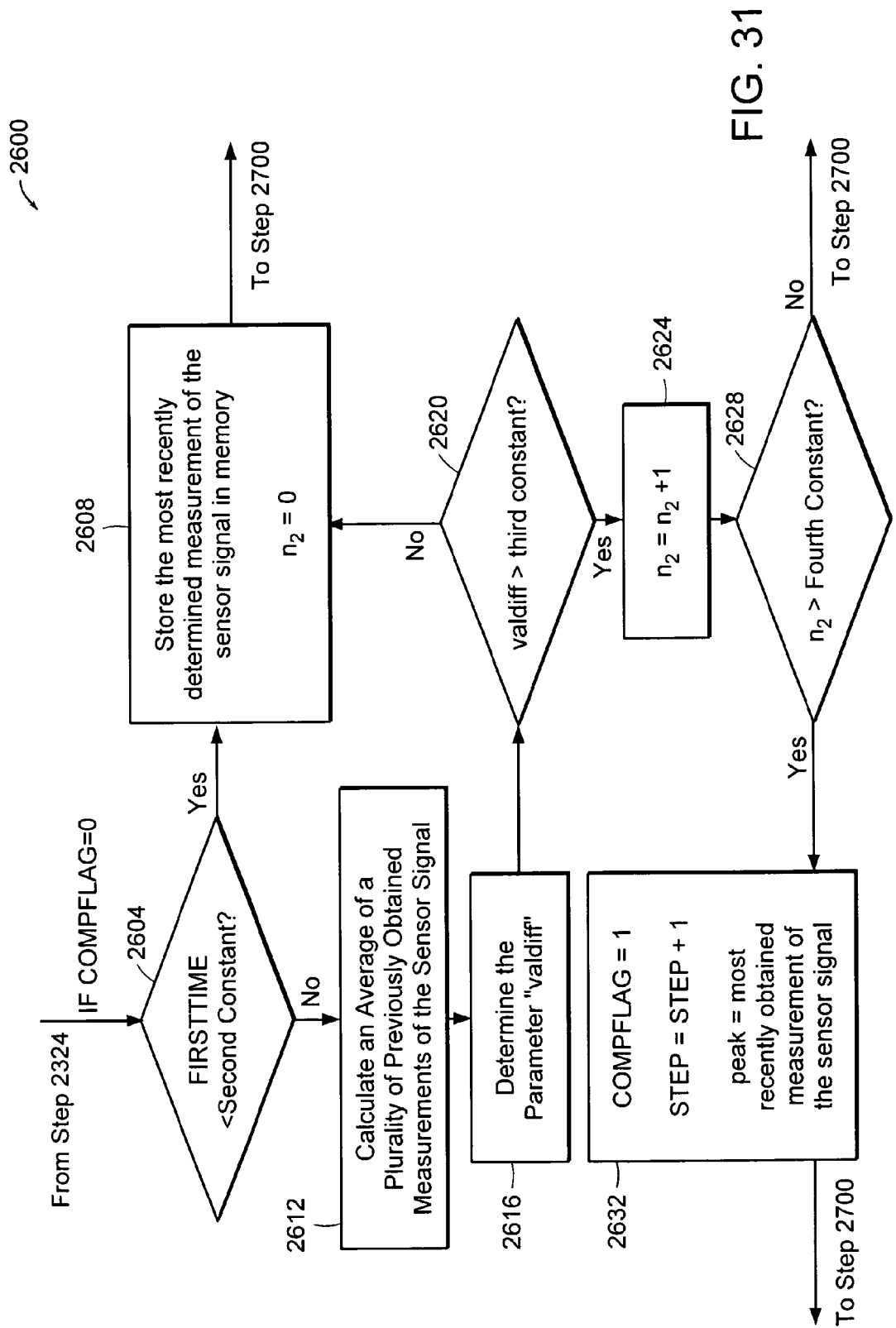
FIG. 31 is a flow chart of a method for determining whether a sole of an article of footwear has compressed using the intelligent system of FIG. 1 in accordance with one embodiment of the invention.

FIG. 31 depicts one embodiment of a method 2600 for determining whether the sole 104 of the article of footwear 100 has compressed. In the illustrated embodiment, the method 2600 is only performed if the parameter compression flag ("COMPFLAG") is set to 0, indicating that the intelligent system 106 has not yet detected compression in the sole 104. By default, the parameter "COMPFLAG" is initially set to 0. At step 2604, a counter "FIRSTTIME" is compared to a second constant. The counter "FIRSTTIME" is incremented each time step 2500 (see FIGS. 23 and 25) is completed (i.e., each time a measurement of the sensor signal is determined). If the counter "FIRSTTIME" is less than the second constant, the most recently determined measurement of the sensor signal (determined at step 2528 of FIG. 30) is stored in the microcontroller's memory at step 2608 and no other steps of the method 2600 are completed. In one embodiment, the microcontroller employs a first-in-first-out (FIFO) buffer that is capable of storing a pre-determined number of measurements of the sensor signal, for example between ten and 30. In such an embodiment, once the FIFO buffer is full, each time a newly determined measurement of the sensor signal is to be stored in the FIFO buffer, the oldest determined measurement of the sensor signal stored in the FIFO buffer is discarded.

If the counter "FIRSTTIME" is greater than the second constant, the intelligent system 106 proceeds to perform step 2612. In one embodiment, the value for the second constant is between 15 and 30. In such an embodiment, step 2500 (i.e., the step of measuring the sensor signal) is guaranteed to be repeated a plurality of times to obtain a plurality of measurements of the sensor signal before the intelligent system 106 proceeds to step 2612.

In one embodiment, an average of a plurality of previously obtained measurements of the sensor signal (each measurement of the sensor signal being previously determined at step 2528 of FIG. 30 and stored in the microcontroller's memory at step 2608) is calculated at step 2612. The measurement of the sensor signal most recently determined at step 2528 is not, however, included in the calculation of this average. A parameter "valdiff", which represents the difference between the average calculated at step 2612 and the measurement of the sensor signal most recently determined at step 2528, is then determined at step 2616. The parameter "valdiff" is then compared to a third constant at step 2620. If the parameter "valdiff" is greater than the third constant, the most recently obtained measurement of the sensor signal is smaller than the average of the plurality of previously obtained measurements of the sensor signal by at least the amount of the third constant and the sole 104 has started to compress. In such a case, the intelligent system 106 increments a counter "$n_2$" at step 2624, which is initially set to zero. Otherwise, if the parameter "valdiff" is less than the third constant, the intelligent system 106 returns to step 2608 to store the most recently obtained measurement of the sensor signal in the microcontroller's memory and to reset the counter "$n_2$" to zero. The value for the third constant may vary depending on, for example, the thickness of the midsole, the noise of the sensor signal, and/or the sampling rate (8 bit or 16 bit). For example, the value for the third constant may be between 2 and 16 for an 8 bit system and between 2 and 64 for a 16 bit system.

At step 2628, the counter "$n_2$" is compared to a fourth constant. If the counter "$n_2$" is greater than the fourth constant, the intelligent system 106 determines that the sole 104 has compressed and sets the parameter "COMPFLAG" equal to 1 at step 2632. The intelligent system 106 also sets, at step 2632, the parameter "peak" equal to the most recently determined measurement of the sensor signal, and increments the counter "STEP", which is described below.

In one embodiment, the fourth constant of step 2628 is chosen so that the comparison of step 2620 must be true a number of consecutive times before the intelligent system 106 will determine the sole 104 to have compressed and, consequently, proceed to step 2632. In one embodiment, the fourth constant is between two and five. With the fourth constant set equal to five, for example, step 2620 would need to be true six consecutive times for the intelligent system 106 to determine that the sole 104 of the article of footwear 100 has compressed and, consequently, proceed to step 2632.

Upon completion of step 2608 or 2632, or where the counter "$n_2$" is not greater than the fourth constant, the intelligent system 106 moves on to step 2700.

Figure 32:
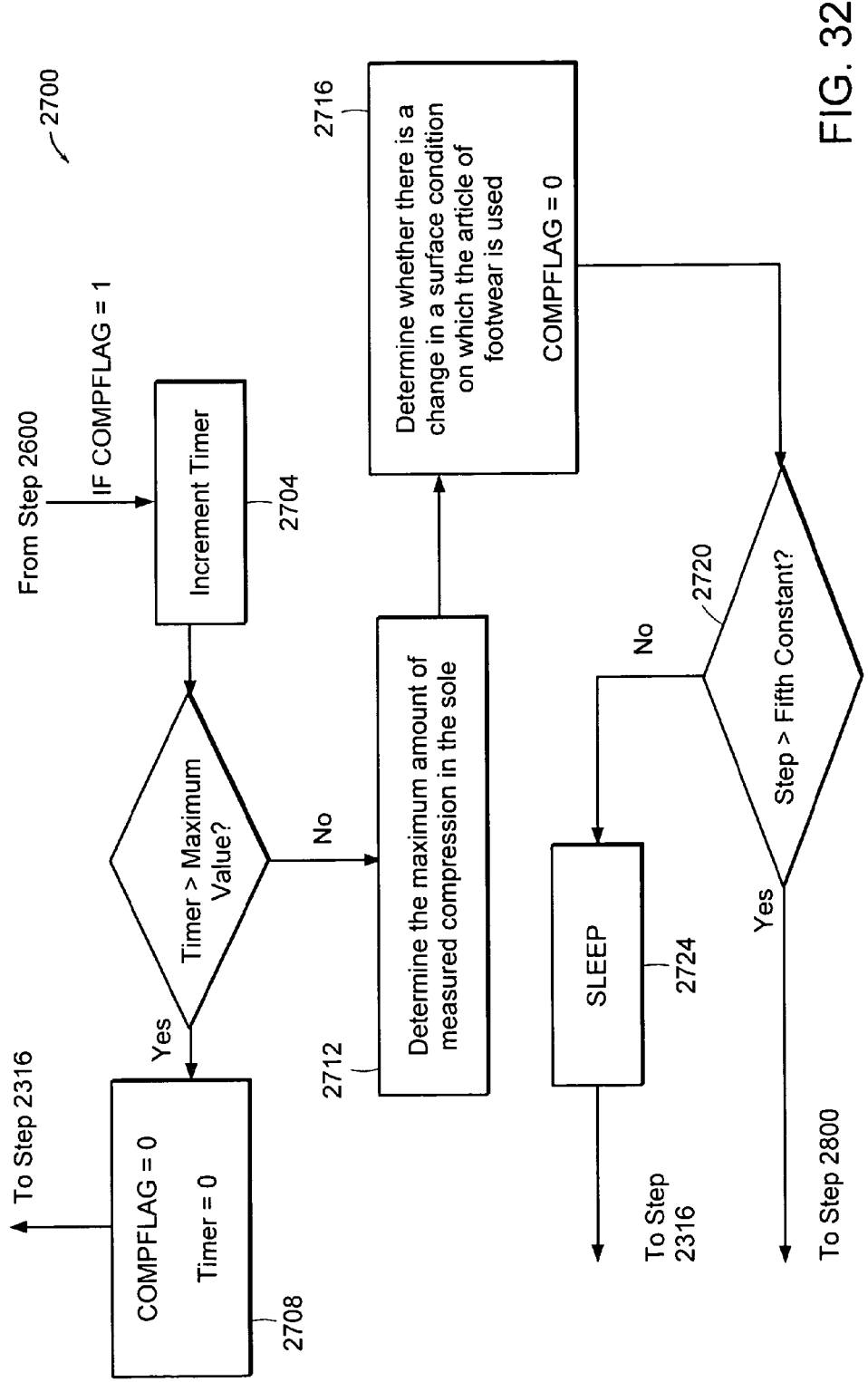
FIG. 32 is a flow chart of a method for monitoring the sensor signal to detect a compression in a sole of an article of footwear using the intelligent system of FIG. 1 in accordance with one embodiment of the invention.

FIG. 32 depicts one embodiment of a method 2700 for performing initial calculations to determine whether an adjustment of the sole 104 of the article of footwear 100 is required. In the illustrated embodiment, the method 2700 is only performed if the parameter "COMPFLAG" is set to 1, meaning that the intelligent system 106 has detected compression in the sole 104. In other words, the method 2700 is only performed if step 2632 of method 2600 has been performed. In one embodiment, following the completion of step 2632, another measurement of the sensor signal is obtained (i.e., the method 2500 of FIG. 30 is again performed) before the method 2700 is performed.

In the embodiment illustrated in FIG. 32, the intelligent system 106 first increments, on each iteration through the steps of the method 2700, a timer at step 2704. If the timer is greater than a chosen maximum value, indicating that step 2712 of the method 2700 is continually being repeated, the intelligent system 106 proceeds to re-set both the parameter "COMPFLAG" and the timer to zero at step 2708. Otherwise, if the timer is less than the chosen maximum value, the intelligent system proceeds to step 2712.

At step 2712, the intelligent system 106, which knows that the sole 104 has recently compressed and may still be compressing, determines the maximum amount of measured compression in the sole 104. Specifically, the intelligent system 106 determines, at step 2712, the real peak value for the amount of compression in the sole 104. In one embodiment, the intelligent system 106 does so by determining if the sole 104 is still compressing. More specifically, the intelligent system 106 compares the most recently obtained measurement of the sensor signal to the value of the parameter "peak" determined at step 2632 of FIG. 31 (this is why in one embodiment, as stated above, following the completion of the step 2632, another measurement of the sensor signal is obtained before the method 2700 is performed). If the most recently obtained measurement of the sensor signal is lower than the value of the parameter "peak" (indicating greater and, therefore, continued compression in the sole 104), the value of the parameter "peak" is reset to that most recently obtained measurement of the sensor signal and a new measurement of the sensor signal is obtained for comparison to the newly reset value of the parameter "peak". In one embodiment, this comparison and the described subsequent steps continue until the most recently obtained measurement of the sensor signal is greater than the value of the parameter "peak" (indicating less compression in the sole 104). If the most recently obtained measurements of the sensor signal are greater than the value of the parameter "peak" a certain number of consecutive times (indicating expansion or decompression of the sole 104), the value of the parameter "peak" truly represents the maximum amount (or real peak) of measured compression in the sole 104. Otherwise, if the most recently obtained measurements of the sensor signal are not greater than the value of the parameter "peak" a certain number of consecutive times (i.e., if a recently obtained measurement of the sensor signal is lower than the value of the parameter "peak"), the intelligent system 106 sets the value of the parameter "peak" equal to the recently obtained measurement of the sensor signal that is lower than the value of the parameter "peak" and a new measurement of the sensor signal is obtained for comparison to the newly reset value of the parameter "peak". The intelligent system 106 then continues to proceed as described above.

Once the maximum amount of measured compression in the sole 104 has been determined, the intelligent system 106 determines, at step 2716, whether there is a change in a surface condition on which the article of footwear 100 is used. In one such embodiment, the intelligent system 106 calculates the absolute compression in the sole 104 over time and the deviation of the compression in the sole 104 over time or an approximation therefor.

It should be understood that over time, the intelligent system 106 will calculate, at step 2712, a plurality of "peak" values that each represent the maximum amount of measured compression in the sole 104 (e.g., the intelligent system 106 will calculate one such "peak" value on each step of a wearer of the article of footwear 100). These "peak" values may be stored in the microcontroller's memory, for example in a FIFO buffer of an appropriate size. Accordingly, a short-term peak average may be calculated at step 2716 by averaging a certain number of those most recently calculated peak values. The average calculated at step 2612 on the most recent iteration through the steps of the method 2600 (see FIG. 31) may then be subtracted from that short-term peak average. In one embodiment, this difference represents the absolute compression in the sole 104 over time.

The deviation (for example, a standard deviation or an approximation therefor) of the peak values most recently calculated at step 2712 may also be calculated at step 2716 to represent the deviation of the compression in the sole 104 over time. In one embodiment, this involves calculating a long-term peak average by averaging, for example, a greater number of the most recently calculated "peak" values than as described above for the short-term peak average. The long-term peak average may then be used for comparison to the instantaneous "peak" values determined at step 2712 in calculating the deviation of the peak values or an approximation therefor. Additionally or alternatively, a plurality of further values may be calculated at step 2716 for use in refining or determining the state of the sole 104.

Having calculated both the absolute compression in the sole 104 over time and the deviation of the compression in the sole 104 over time, the intelligent system 106 can compare the two to determine whether there is a change in the surface condition on which the article of footwear is being used. Generally, the intelligent system 106 can determine a change in the surface condition on which the article is being used by comparing two parameters; one parameter remaining at least substantially constant, while the other parameter changes when there is a change in the surface condition. In addition to the absolute compression and the deviation described above, the parameters can include, for example, an acceleration profile, a compression profile, a strike pattern, and compression force.

Typically, a decrease in the absolute compression in the sole 104 over time together with substantially no change in the deviation of the compression in the sole 104 over time, or an increase in the deviation of the compression in the sole 104 over time together with substantially no change in the absolute compression in the sole 104 over time, indicates that a wearer of the article of footwear 100 has moved from a hard ground surface (e.g., pavement or an asphalt road) to a soft ground surface (e.g., a soft forest ground). Conversely, an increase in the absolute compression in the sole 104 over time together with substantially no change in the deviation of the compression in the sole 104 over time, or a decrease in the deviation of the compression in the sole 104 over time together with substantially no change in the absolute compression in the sole 104 over time, indicates that a wearer of the article of footwear 100 has moved from a soft ground surface to a hard ground surface. Where there is little or no change in both the absolute compression in the sole 104 over time and the deviation of the compression in the sole 104 over time, there is likely no change in the surface condition on which the article of footwear 100 is used. Accordingly, by comparing the absolute compression in the sole 104 over time to the deviation of the compression in the sole 104 over time, the intelligent system 106 may determine whether there has been a change in the surface condition on which the article of footwear 100 is being used and, if so, may determine what that change is. In one embodiment, to compare the absolute compression in the sole 104 over time to the deviation of the compression in the sole 104 over time, the intelligent system 106 computes a ratio of the two measurements.

In one particular embodiment, the intelligent system 106 only determines whether there has been a change in the surface condition on which the article of footwear 100 is being used and, if so, what that change is after a wearer of the article of footwear 100 has taken a plurality of steps, either initially or after the intelligent system 106 last made such determinations. For example, in one embodiment, the intelligent system 106 does not make such determinations until the wearer of the article of footwear has taken between 15 and 30 steps, either initially or after the intelligent system 106 last made such determinations.

At step 2716, the intelligent system 106 also resets the parameter "COMPFLAG" to 0. After determining whether there has been a change in the surface condition on which the article of footwear 100 is used and resetting the parameter "COMPFLAG" to 0, the intelligent system 106 determines whether a wearer of the article of footwear 100 has taken a certain number of steps by comparing, at step 2720, the counter "STEP" to a fifth constant. If the counter "STEP" is greater than the fifth constant, meaning that the wearer of the article of footwear 100 has taken a certain number of steps, the intelligent system 106 proceeds to step 2800. If not, no adjustment to the sole 104 is made. Instead, the intelligent system 106 enters a sleep mode at step 2724 for a period of time (e.g., between 200 and 400 milliseconds) to conserve energy before returning to step 2316 in FIG. 28. Typically, the value of the fifth constant is between two and six. Moreover, the counter "STEP" may be incremented every time the parameter "COMPFLAG" is set to 1 (see step 2632 in FIG. 31).

Figure 33B:
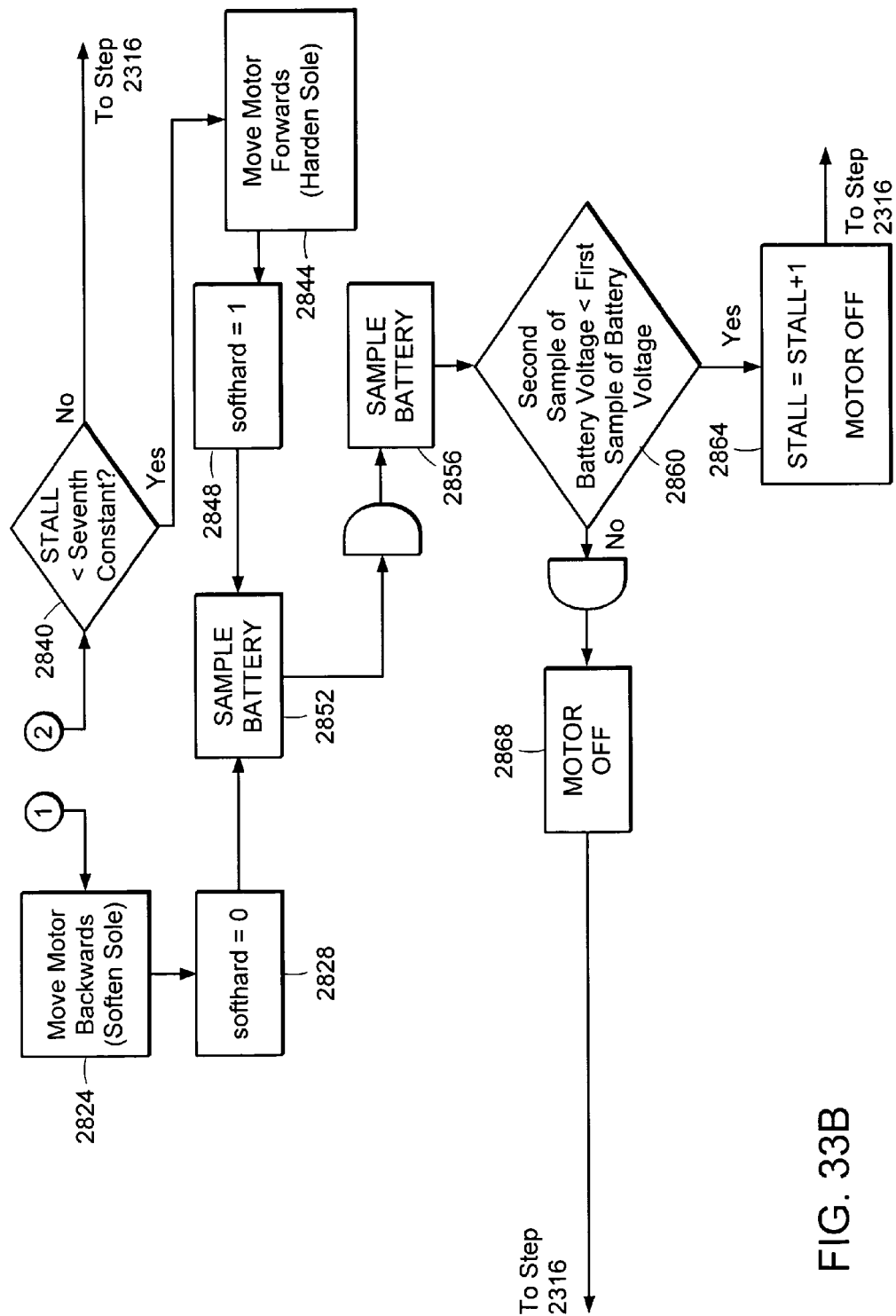
FIG. 33 is a flow chart of a method for determining whether an adjustment of a sole of an article of footwear is required using the intelligent system of FIG. 1 in accordance with one embodiment of the invention.

FIG. 33 depicts one embodiment of a method 2800 for performing additional calculations to determine whether an adjustment of the sole 104 of the article of footwear 100 is required and, if so, for adjusting the sole 104. At step 2804, the same comparison as at step 2720 of FIG. 32 is made. If the counter "STEP" is less than the fifth constant, the intelligent system 106 returns to step 2316 of FIG. 28. If, on the other hand, the counter "STEP" is greater than the fifth constant, the short-term peak average (determined at step 2716 of FIG. 32)

may be adjusted, at step 2808, for comparison to the one or more thresholds of compression determined either at step 2424 or at step 2428 of FIG. 29. In a particular embodiment, if the surface condition on which the article of footwear 100 is used last changed to a hard ground surface, no adjustment to the short-term peak average is made. On the other hand, if the surface condition on which the article of footwear 100 is used last changed to a soft ground surface, the short-term peak average is decreased by a certain amount, thereby causing the intelligent system 106 to think that there was more compression than there actually was and encouraging the intelligent system 106 to harden the sole 104 of the article of footwear 100. This latter adjustment is equivalent to changing the thresholds of compression employed at steps 2812 and 2832.

At step 2812, it is determined, by comparing the (un)adjusted value for the short-term peak average determined at step 2808 to the lower threshold of compression determined either at step 2424 or at step 2428 of FIG. 29, whether the compression in the sole 104 is less than that lower threshold of compression. If so, it is determined, at step 2816, whether the parameter "softhard" equals 1, meaning that the sole 104 of the article of footwear was most recently hardened. If so, the counter "STALL" is set to 0 at step 2818 and compared to a sixth constant at step 2820. If not, the counter "STALL" is not reset to 0, but is simply compared to the sixth constant at step 2820. If the counter "STALL" is less than the sixth constant, meaning that motor 132 has not been blocked a pre-determined number of consecutive times when the intelligent system 106 has attempted to move the motor 132 backward to soften the sole 104, the motor 132 is moved backward, at step 2824, to soften the sole 104. The parameter "softhard" is then set to 0 at step 2828, indicating that the sole 104 of the article of footwear 100 was most recently softened by moving the motor 132 backward. If, on the other hand, the counter "STALL" is determined at step 2820 to be greater than the sixth constant, meaning that the motor 132 has been blocked a pre-determined number of consecutive times when the intelligent system 106 has attempted to move the motor 132 backward to soften the sole 104, the motor 132 is not moved backward. Instead, the intelligent system 106 returns to perform step 2316 of FIG. 28. In one embodiment, the sixth constant is between three and ten.

If it is determined, at step 2812, that the compression in the sole 104 is greater than the lower threshold of compression determined either at step 2424 or at step 2428 of FIG. 29, the intelligent system 106 moves to step 2832. At step 2832, it is determined, by comparing the (un)adjusted value for the short-term peak average determined at step 2808 to the upper threshold of compression determined either at step 2424 or at step 2428 of FIG. 29, whether the compression in the sole 104 is greater than that upper threshold of compression. If so, it is determined, at step 2836, whether the parameter "softhard" equals 0, meaning that the sole 104 of the article of footwear was most recently softened. If so, the counter "STALL" is set to 0 at step 2838 and compared to a seventh constant at step 2840. If not, the counter "STALL" is not reset to 0, but is simply compared to the seventh constant at step 2840. If the counter "STALL" is less than the seventh constant, meaning that the motor 132 has not been blocked a pre-determined number of consecutive times when the intelligent system 106 has attempted to move the motor 132 forward to harden the sole 104, the motor 132 is moved forward, at step 2844, to harden the sole 104. The parameter "softhard" is then set to 1 at step 2848, meaning that the sole 104 of the article of footwear 100 was most recently hardened by moving the motor 132 forward. If, on the other hand, the counter "STALL" is determined at step 2840 to be greater than the seventh constant, meaning that the motor 132 has been blocked a pre-determined number of consecutive times when the intelligent system 106 has attempted to move the motor 132 forward to harden the sole 104, the motor 132 is not moved forward. Instead, the intelligent system 106 returns to perform step 2316 of FIG. 28. In one embodiment, the seventh constant is between three and ten.

If it is determined, at step 2832, that the compression in the sole 104 is lower than the upper threshold of compression determined either at step 2424 or at step 2428 of FIG. 29 (meaning that the compression in the sole 104 lies between the lower and upper thresholds of compression), the intelligent system 106 does not move the motor 132 to adjust the sole 104, but instead returns to perform step 2316 of FIG. 28.

With reference to FIG. 2B, it should be understood that, in one embodiment, moving the motor 132 backward or forward as described above actually means running the motor 132 in one direction or another to drive the transmission element 134 in one direction or another (e.g., clockwise or counter-clockwise). Consequently, the limiter 128, which is threadedly engaged by the transmission element 134, is moved backward or forward relative to the expansion element 126, as shown generally by arrow 140 in FIG. 2B. As such, the sole 104 may be softened or hardened.

After having begun to move the motor 132 either at step 2824 or at step 2844, the voltage of the battery powering the intelligent system 106 is sampled a first time at step 2852. The voltage of the battery will have dropped as a result of starting the motor 132 movement. After a brief passage of time, for example about 5 to about 40 milliseconds, the voltage of the battery is sampled a second time at step 2856. If the motor 132 is moving freely, the voltage of the battery will have increased and thus the second sample of the battery voltage will be greater than the first sample of the battery voltage. If, on the other hand, the motor 132 is blocked, the voltage of the battery will have dropped even further than it did when the motor 132 first started to move and, thus, the second sample of the battery voltage will be less than the first sample of the battery voltage. At step 2860, the second sample of the battery voltage is compared to the first sample of the battery voltage. If the second sample of the battery voltage is less than the first sample of the battery voltage, the counter "STALL" is incremented and the motor 132 turned off at step 2864, as the motor 132 is blocked. If, on the other hand, the second sample of the battery voltage is greater than the first sample of the battery voltage, the motor 132 is allowed to move for a period of time (for example, less than 300 milliseconds), as it is moving freely, before being turned off at step 2868.

Following step 2864 or step 2868, the intelligent system 106 returns to step 2316 of FIG. 28 for the next iteration through the steps of the method 2300.

Figure 34:
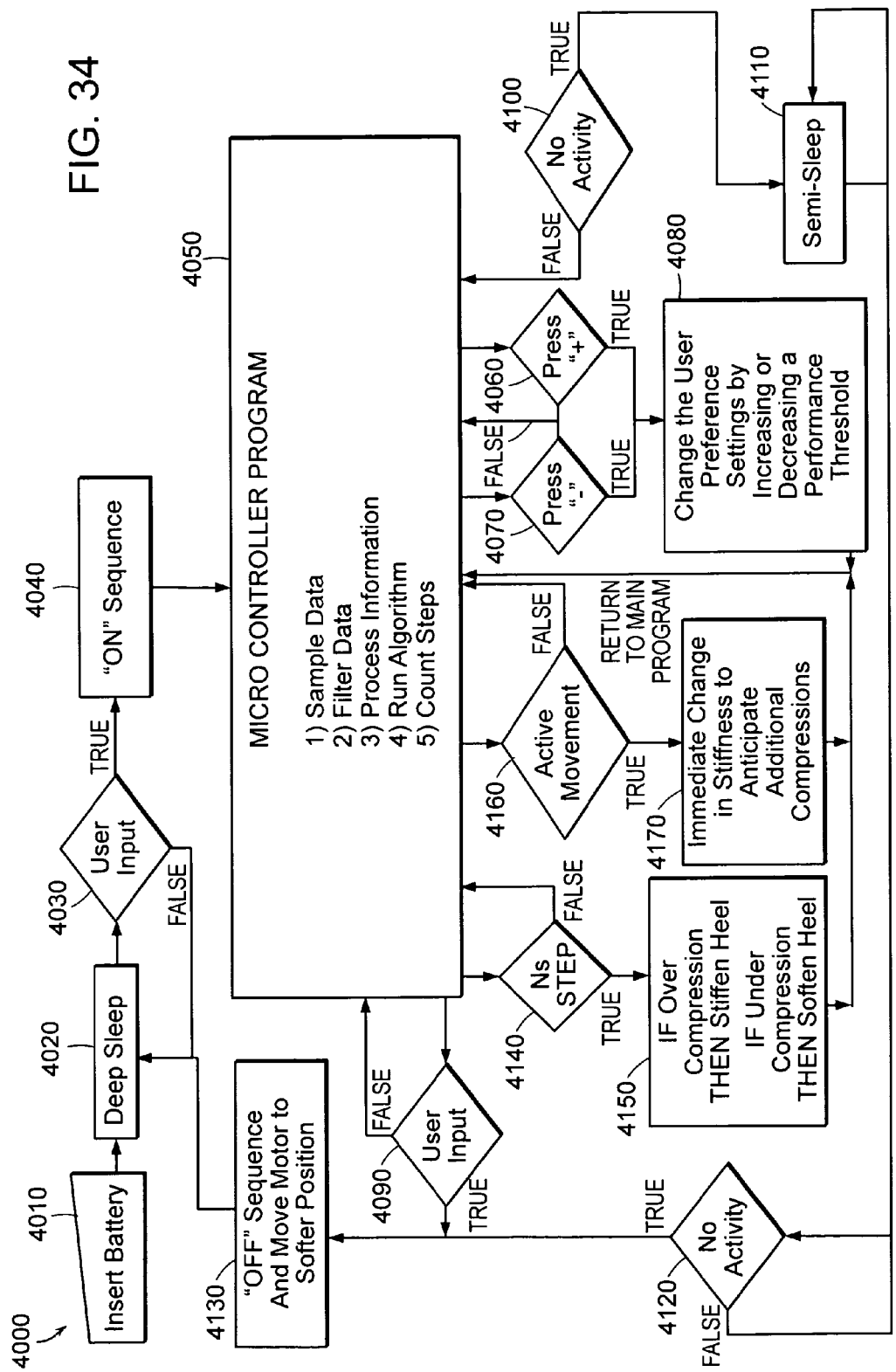
FIG. 34 is a flow chart depicting an alternative mode of operation for an intelligent system in accordance with one embodiment of the invention.

FIG. 34 depicts another possible algorithm that may be performed by the intelligent system 106. In particular, FIG. 34 illustrates one embodiment of a method 4000 for modifying a performance characteristic of an article of footwear designed for use in basketball or other sporting activity requiring similar physical movements and including an intelligent system. The method 4000 can include any of the other aspects of the previously described algorithms.

The control algorithm is adapted to provide appropriate control of the stiffness of the article of footwear dependant upon the specific requirements of the footwear. In the example embodiment of FIG. 34, the control algorithm is adapted to provide stiffness control for a basketball shoe. This algorithm is designed to adjust the stiffness for motions including running, jumping, landing, cutting, turning, and other physical motions associated with basketball. Further, this algorithm is intended to provide immediate responsiveness of the intelligent system 106 to adjust the appropriate performance characteristic of the shoe.

The method 4000 begins by providing power to the intelligent system. For example, a battery may act as the power source and may be installed in the intelligent system at step 4010. Once the battery is installed in the intelligent system, the intelligent system may enter a "Deep Sleep" mode at step 4020. The "Deep Sleep" mode can minimize the activity and power requirements of the intelligent system when not in use to conserve battery power. For example, in a "Deep Sleep" mode, any LED or other indicators may be turned off, the motor can be moved to place the adjustable element in a "soft" configuration, and the motor can then be turned off, power to all other extraneous systems and elements can be turned off, and power to the control unit can be minimized. In one embodiment, only power to a single input mechanism need be maintained, so that the system can be turned on upon activation of that input mechanism.

The input mechanism used to turn the intelligent system on may be a user input interface such as a button or capacitive user interface, a vibration sensor that activates the intelligent system upon sensing a vibration (which will happen whenever the shoe is in use), a pressure sensor within the shoe that can activate the intelligent system upon sensing a force (indicating that the shoe is being put on), a sensor calibrated to activate the intelligent system upon sensing a change in capacitance inside the upper (such as the change in capacitance resulting from a foot being inserted), a heat sensor calibrated to activate the intelligent system upon sensing a certain temperature (such as the rise in temperature within a shoe after a foot is inserted), or other appropriate mechanism. In an alternative embodiment, more than one of the input mechanisms can be used. For example, the footwear could employ both a user interface and a vibration sensor to turn the intelligent system on from a "Deep Sleep" mode 4020.

According to the method 4000, the intelligent system 106 can be turned on by a user input 4030 from a "Deep Sleep" mode 4020 by simultaneously pressing the "+" and "−" buttons on a user interface. Alternatively, only one of the "+" and "−" buttons need be pressed or the user input could be triggered through the capacitive user interface. Upon an initial signal from the user interface, an "ON" sequence 4040 is initiated. This sequence includes powering up any systems and sensors required for the operation of the intelligent system 106, and powering up any indicators, such as, but not limited to, LED indicators that provide information to a wearer. The "ON" sequence 4040 can also include driving the motor, for example for about 200 milliseconds, to "stiffen" the adjustable element to an initial operating stiffness. In an alternative embodiment, the "ON" sequence can drive the motor for a greater or lesser time, or at a higher or lower speed, to vary the initial operating stiffness based on the specific requirements of the shoe and the wearer. In a further alternative embodiment, the adjustable element need not be adjusted upon execution of an "ON" sequence.

Once the intelligent system 106 is on, it initiates a micro-controller program 4050 to operate the intelligent system 106. This program 4050 may include a number of functions. The micro-controller program 4050 obtains data from any of one or more sensors adapted to provide relevant information to the intelligent system 106. This data can then be sampled, for example at 1500 Hz, and filtered before being processed by the micro-controller program 4050. In an alternative embodiment, data may be sampled at any rate necessary to provide the appropriate information to the micro-controller program 4050. This sample rate may range from about 1 Hz to about 100 kHz, or more preferably from about 100 Hz to about 5000 Hz. If multiple sensors are utilized, each sensor may be sampled at a different frequency, based on the function of the sensor and the requirements of the micro-controller program 4050. Alternatively, the sensors may all be sampled at the same sample rate. In one embodiment of the invention, the power to a sensor can be turned on and off between readings, in order to save energy.

A number of different forms of filtering may be applied to the sampled data to improve the quality of the data processed by the control algorithm of the micro-controller program 4050. These forms of filtering may include, but are not limited to, high-pass, low-pass, and/or band-pass filtering. Alternatively, no filtering of the sampled data need be carried out prior to processing by the control algorithm. In one embodiment, a floating memory can be employed to store data received from the sensor or sensors. One example of floating memory can store sixteen values, thereafter, upon the seventeenth value being calculated, the first one is deleted from the memory and the new one is added. In alternative embodiments, the memory may be able to store a greater or smaller number of data readings.

While in the "ON" mode, a user can change the preference settings of the footwear by pressing one of the "+" or "−" buttons on the user interface or operating the capacitive user interface, as described hereinabove. In one example embodiment, upon pressing the "+" button 4060, the intelligent system 106 will increase the threshold for the compression, while pressing the "−" button 4070 will result in the intelligent system 106 decreasing the threshold for the compression. As a result, the required compression that must be sensed by the intelligent system 106 before a change in the stiffness of the footwear is implemented can be changed by a user, depending upon a given user's personal preferences, weight, or running style, or upon the sport being performed. See, for example, FIG. 29.

In one embodiment, the intelligent system 106 comprises multiple performance characteristic settings, for example, nine different "hardness" threshold settings, or states, from a maximum hardness threshold to a minimum hardness threshold. In this embodiment, by pressing the "+" button 4060 (or otherwise actuating a user interface), the micro-controller program 4050 will check to see if the hardness threshold setting is at its maximum value. That means it checks to see if the intelligent system 106 can further increase the hardness threshold of the sole of the footwear. If further increasing of the hardness threshold of the sole of the footwear is possible, the micro-controller program 4050 will instruct the intelligent system 106 to change the threshold 4080 of the sole of the footwear based on the input from the user. In one embodiment, a single press of the "+" button, or otherwise actuating a user interface, can increase the hardness threshold setting by a single degree, while in alternative embodiments a single press of the button by a user can increase the hardness threshold by a greater degree. In alternative embodiments, the intelligent system 106 can include a greater or smaller number of threshold settings (e.g., hardness) from, for example, two to twenty settings.

In the same manner, by pressing the "−" button 4070 (or otherwise actuating a user interface), the micro-controller program 4050 will check to see if the hardness threshold setting is at its minimum value. If a further decreasing of the hardness threshold of the sole of the footwear is possible, the micro-controller program 4050 will instruct the intelligent system 106 to change the hardness threshold 4080 of the sole of the footwear based on the input from the user. As in the case for increasing the hardness threshold, the value by which the hardness threshold is decreased can be set to any number of values based on the requirements of the user. This value by which the hardness threshold is increased or decreased by a single press of the "+" button 4060 or the "−" button 4070 may be constant or vary depending upon the setting when the button is depressed.

Once a maximum or minimum threshold is reached, pressing the "+" button 4060 or the "−" button 4070 to further increase or decrease the setting will have no further effect. In one embodiment, a LED, or a series of LEDS, can be used to display the current hardness, and/or hardness threshold setting on the article of footwear, or can be used to indicate when a change is being made to the hardness threshold setting. This value may be constantly displayed on the LEDs, or turn off after a set time to conserve power.

In an alternative embodiment, the "+" button 4060 or "−" button 4070 can be used to directly change the stiffness of the sole of the footwear, or change another parameter associated with the intelligent system 106. In a further alternative embodiment, these functions may be performed when the intelligent system 106 is in any operational mode, including for example an "OFF", "DEEP SLEEP", or "Semi-Sleep" mode.

In one aspect of the micro-controller program 4050, the intelligent system 106 can count the number of steps $n_s$ taken by a wearer. This can be achieved, for example, by any of the methods described previously. An adjustment of the compression of the intelligent system 106 can then be carried out after a set number of steps $n_s$, for example every eight steps. In alternative embodiments, an adjustment can be carried out after fewer or greater steps, depending upon the requirements of the user and the specific task being performed. In this embodiment, the micro-controller records the sensor readings for eight consecutive steps 4140. Upon the eighth step, the sensor readings can be processed to calculate whether an adjustment 4150 to the compression of the intelligent system 106 is required. This can be achieved, for example, by averaging the value for the eight steps and calculating whether this value is greater than the compression threshold required to initiate a change in the compression of the intelligent system 106. In an alternative embodiment, a number of different algorithms can be employed to calculate whether the compression of the intelligent system 106 should be adjusted. These algorithms can include calculations of the range of compressions throughout the previous eight steps, calculations of higher order responses of the system, filtering of the results to compensate for any spurious results, or other appropriate algorithms.

Once the micro-controller program 4050 has determined whether an adjustment of the compression 4150 is required, the sequence is repeated and compression measurements are taken for another $n_s$ steps. In alternative embodiments of the invention, readings can be taken for a set number of samples, rather than for a set number of user steps before the micro-controller program 4050 determines if an adjustment of the compression is required. The adjustment is made to either stiffen or soften the sole of the shoe, typically while the wearer's foot is in the air.

An adjustment to a performance characteristic of shoe including the intelligent system 106 can also be made immediately upon the sensing of an extreme condition, for example over-compression, 4160, such as may be produced by a jump, a landing, a cut, or other movement associated with basketball, or other sports for which the footwear is configured. An over compression 4160, produced by one of the above-mentioned activities, can result in an irregular profile being observed by a sensor. Excessive over-compression can be defined internally by a series of calculations involving the percentage over-compression in relation to the current threshold setting. If there is a compression which "bottoms out" the shoe or is out of the acceptable functional range, then an immediate motor movement adjusting (e.g., stiffening) the shoe 4170 can be initiated. In addition, the threshold setting can be temporarily changed to accommodate the new motor setting. This adjustment 4170 can be initiated, for example, after a single sensor reading exceeds the set over-compression, after the average of a number of samples exceeds the limit for acceptable overcompression, or after a set number of samples all exceed the required amount. In order for the intelligent system 106 to respond quickly enough to effectively support the movement of the user, the number of samples over which an over-compression should be measured must be small enough, and the sample rate of the sensor and micro-controller program 4050 must be high enough, to sense an active movement of the user before the movement has been completed.

In one embodiment, upon a compression being sensed, a floating memory buffer can store a number of measurements and compare these measurements to determine whether a peak condition has been reached. For example, if the values continue to increase over the buffered measurements, a peak condition has yet to be reached, while if the values begin to decrease over the buffered measurements then a peak condition may have already occurred. This buffer may continuously update to provide continuous information on whether a peak condition is about to occur, is occurring, or has passed; the intelligent system responding accordingly. The number of values stored in this floating memory can be preprogrammed into the intelligent system or be adjustably set by a user. In a further embodiment, information associated with previously sensed peak conditions, such as the magnitude of the over-compression and the time between over-compressions, can be stored within the intelligent system 106. This information can be used as a predictive tool to predict the likelihood of an over-compression occurring at a future time based on a repeated pattern of over-compressions being sensed. Prior information related to sensed peak conditions can also be used to determine whether a specific athletic activity is being performed, or a specific wearer is wearing the footwear, and then adjust a performance characteristic of the footwear accordingly.

As previously shown in FIG. 6, the system 106 can include an interface port 160 to allow information to be downloaded from the system 106 to an external processor. In one embodiment, peak condition information can be downloaded to an external processor for analysis; allowing an athletes' performance to be analyzed in order to aid training. In a further embodiment, different algorithms can be uploaded from an external source into the intelligent system 106, for example to provide specific performance algorithms for different users of an article of footwear or different athletic activities being carried out by a wearer.

Once an immediate adjustment 4170 has been carried out, the algorithm returns to the main micro-controller program 4050 and continues to sample data as before. In one embodiment, once the active movement producing the over-compression has been completed, the stiffness of the intelligent system 106 is returned to its value before the over-compression was measured. In an alternative embodiment, the change to the stiffness can remain until the next set number of steps have been measured and processed, after which an adjustment to the stiffness can be made, if so required. Due to the nature of basketball, where a wide variety of movements may be performed by a user over a short period of time, the system can be configured to ignore slight compressions related to bobbing or standing by setting the compression threshold high enough that only the running, cutting, jumping, landing, and other extreme movements result in the stiffness being adjusted immediately. As described above, the actual threshold value can be adjusted by a user through the user interface to fit a specific user and/or performance requirements.

In the event that no activity is sensed by one or more of the sensors for a certain period of time, the intelligent system 106 may enter a "Semi-Sleep" mode 4110. For example, if no activity is sensed 4100, for example for 5 minutes, the "Semi-Sleep" mode 4110 may be initiated. In alternative embodiments, a greater or lesser time period can be required before the "Semi-Sleep" mode 4110 is initiated. The required time period may be imbedded in the micro-controller program 4050 or set by a user. The "Semi-Sleep" mode 4110 can be indicated by a flash from a LED on regular intervals, such as, for example, every five seconds. In alternative embodiments, the LED can flash at a shorter or longer interval, flash in a different pattern, or remain on in order to indicate that the system 106 is in the "Semi-Sleep" mode 4110. It should be noted that in an article of footwear including a LED, or a series of LEDs, any variety of flashes and or sequences of flashes can be used to indicate any of one or more functions of the intelligent system 106.

In the "Semi-Sleep" mode 4110, the intelligent system 106 can be configured to power up for a brief period at regular intervals to check for activity from one or more sensors. This interval can, in one embodiment, be every fifteen seconds, although shorter or longer intervals between checks may be employed in alternative embodiments. If activity is sensed, the intelligent system 106 can return to the micro-controller program 4050. If no activity is sensed for an extended time period 4120, for example two hours, the intelligent system 106 can be returned the "DEEP SLEEP" mode 4020 or an "OFF" mode 4130. In alternative embodiments, the extended period of no activity 4120 required for the footwear to be idle before the "DEEP SLEEP" 4020 or the "OFF" mode 4130 is enabled may be greater than or less than two hours and can range from, for example, ten minutes to 10 hours.

The intelligent system 106 can be manually put into the OFF mode 4130 or "Deep Sleep" mode 4020 by pressing both the "+" and "−" buttons on the user interface simultaneously 4090. Alternatively, the capacitive user interface could be used to send the necessary signal to the intelligent system 106. To avoid inadvertently turning off the intelligent system 106, the micro-controller program 4050 can, in one embodiment, require that the "+" and the "−" buttons 4090 be held down for a certain period of time before an instruction to initiate the OFF mode 4130 or the "Deep Sleep" mode 4020 is performed. In one embodiment, both the "+" and "−" buttons 4090 may need to be pressed for at least one second before the OFF mode 4130 or the "Deep Sleep" mode 4020 is initiated. In alternative embodiments, a greater or lesser time period may be required for both the "+" and "−" buttons 4090 to be pressed in order to initiate the OFF mode 4130 or the "Deep Sleep" mode 4020. In another embodiment, no extended time period may be required at all, but instead the OFF mode 4130 or the "Deep Sleep" mode 4020 may be initiated immediately upon both the "+" and "−" buttons 4090 being pressed simultaneously. In this embodiment, initiating the OFF mode 4130 or the "Deep Sleep" mode 4020 includes a light "OFF" sequence accompanied by a movement of the motor to the soft configuration.

Figure 35A:
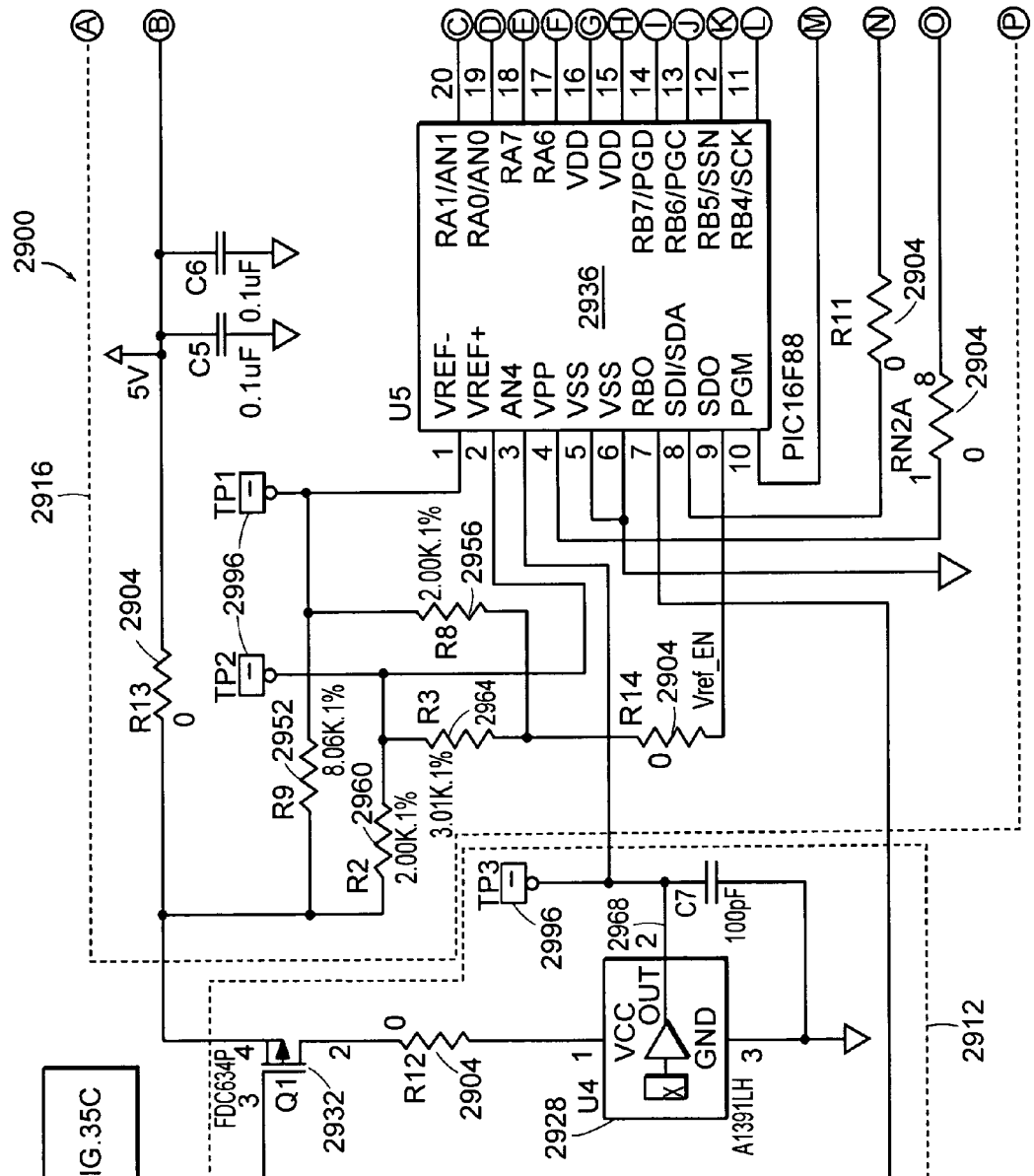
FIG. 35 is a circuit diagram of one embodiment of the intelligent system of FIG. 1 for a left shoe.
Figure 35B:
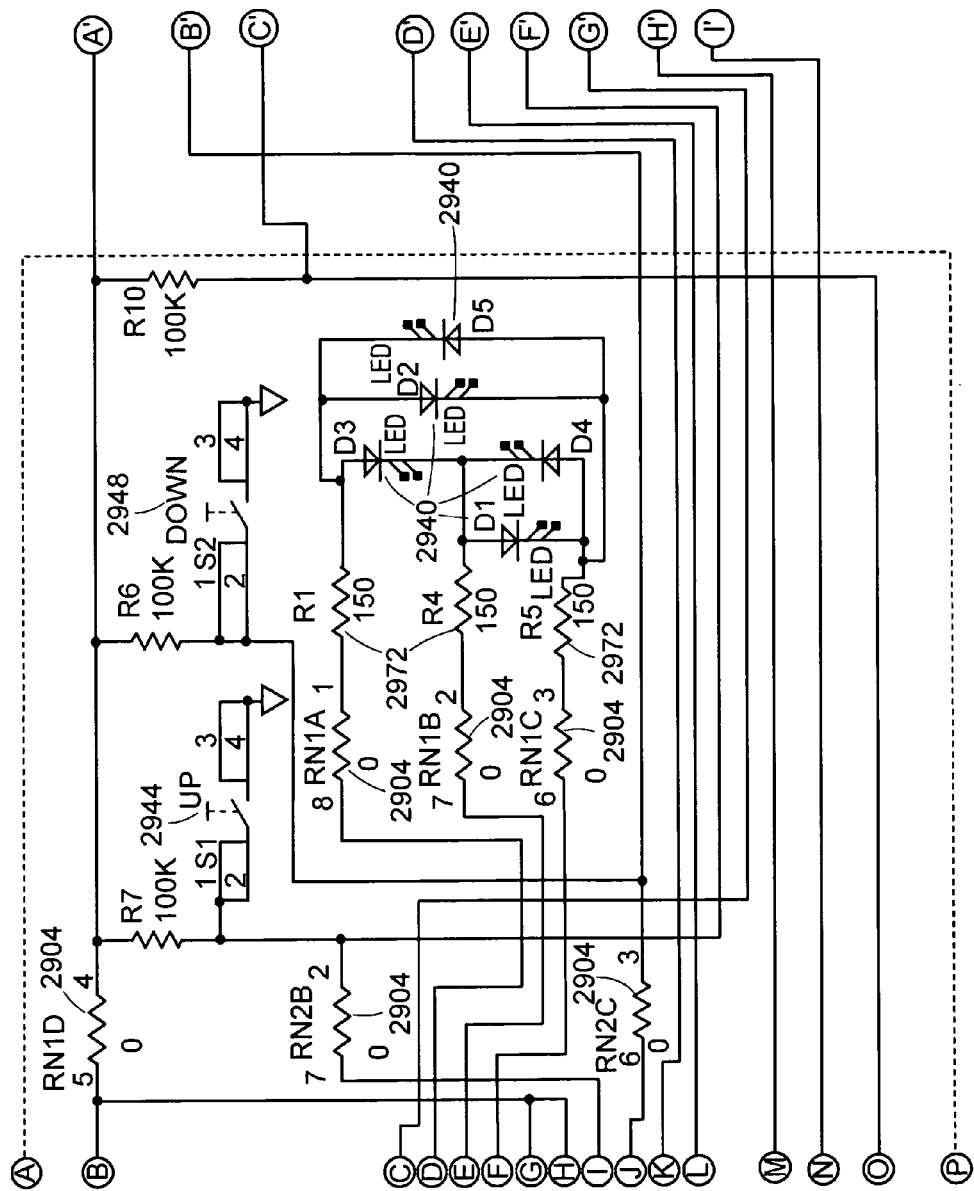
Figure 35C:
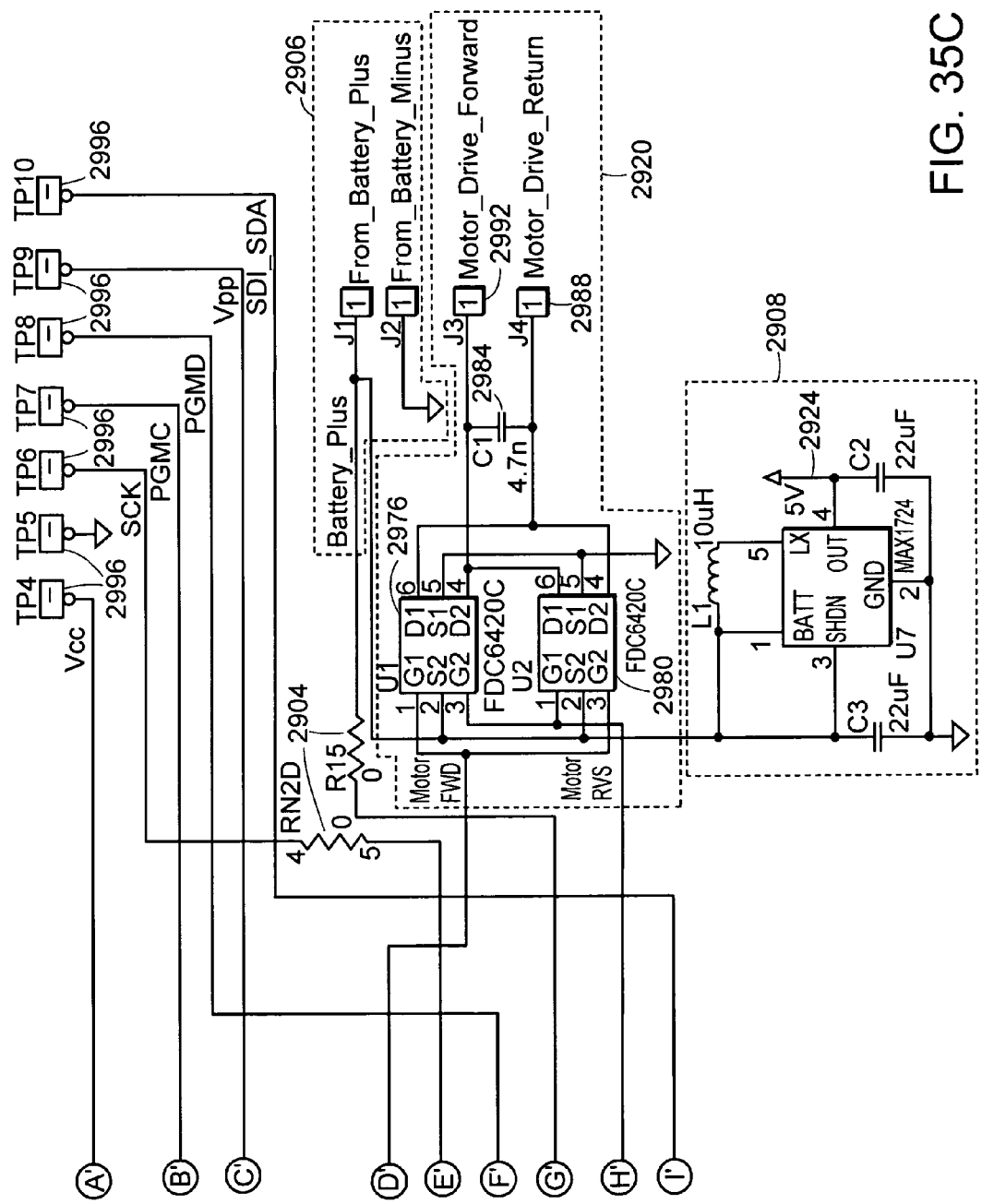
Figures 36, 36A:
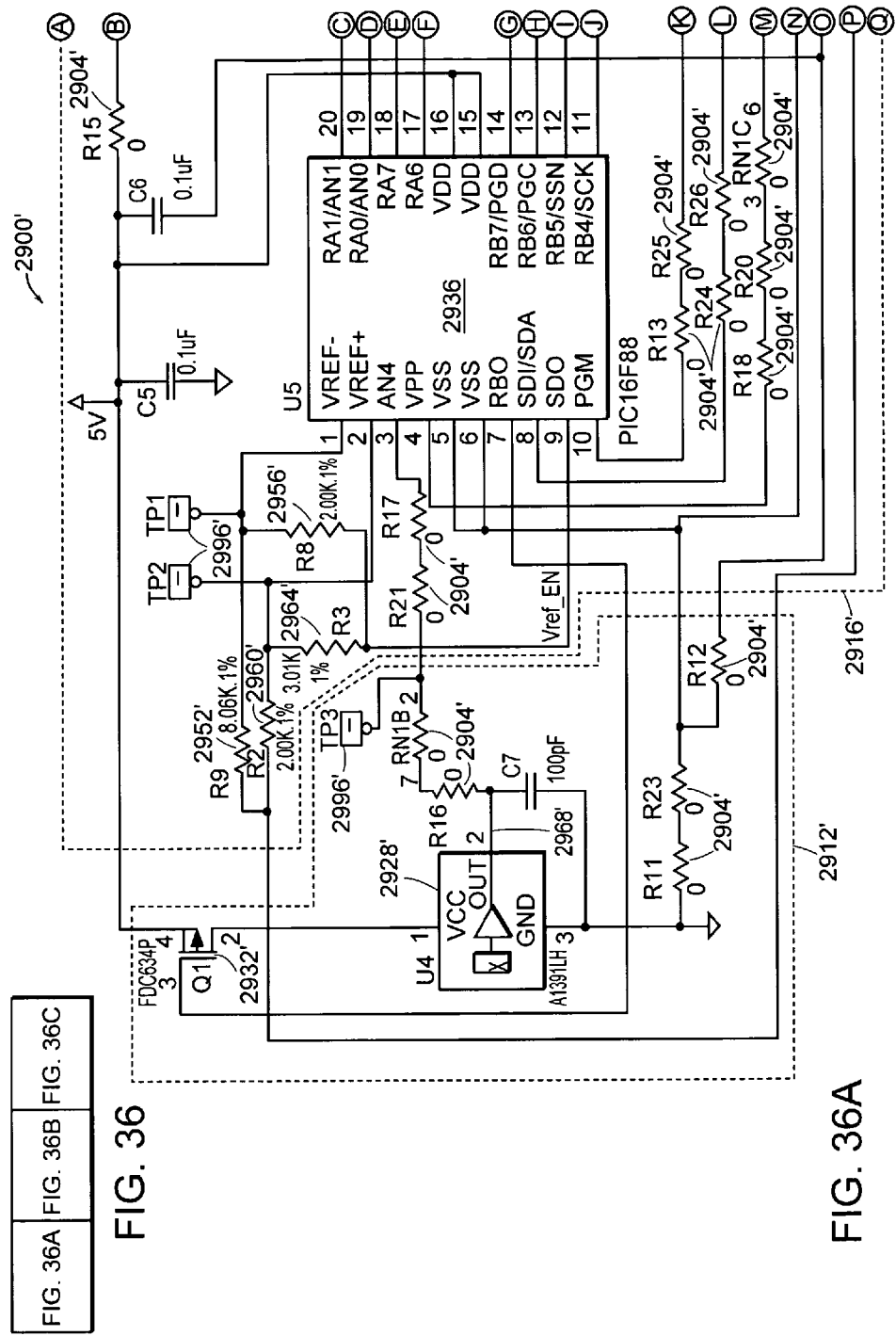
FIG. 36 is a circuit diagram of one embodiment of the intelligent system of FIG. 1 for a right shoe.
Figure 36B:
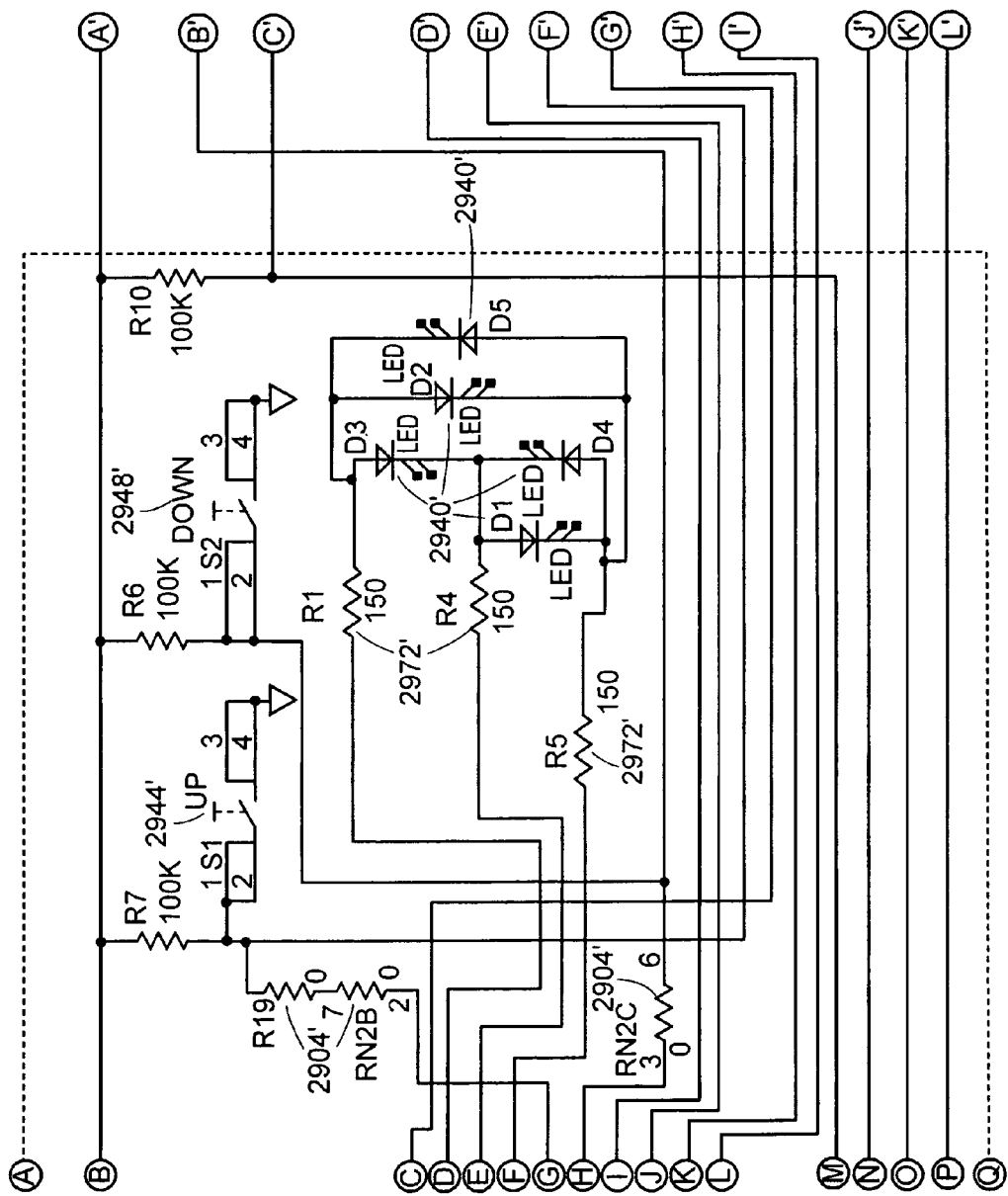
Figure 36C:
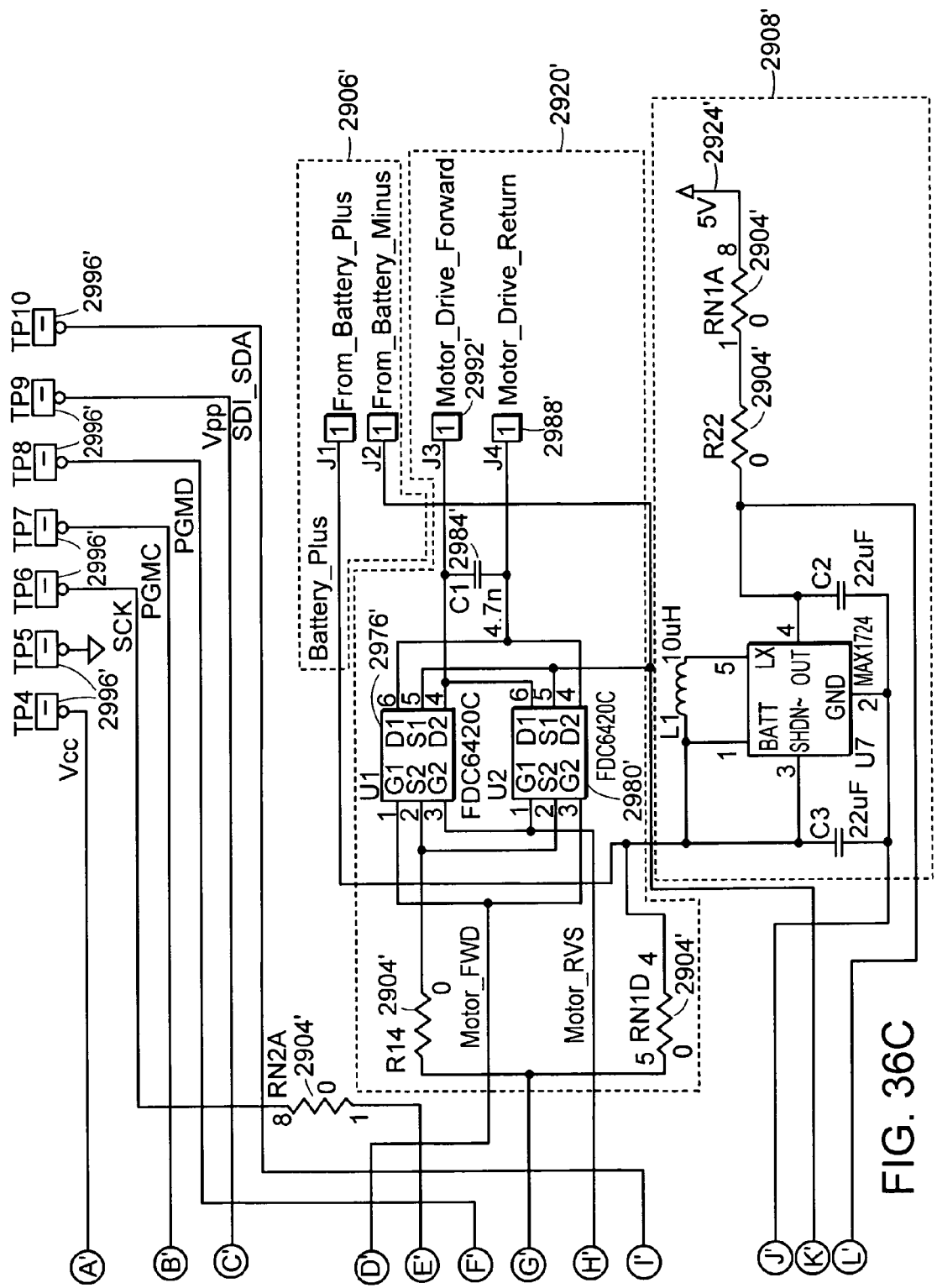

FIG. 35 illustrates one embodiment of an electrical circuit 2900 suitable for implementing an intelligent system 106 in a left shoe in accordance with the invention. FIG. 36 illustrates one embodiment of another electrical circuit 2900' suitable for implementing the intelligent system 106 in a right shoe in accordance with the invention. As illustrated, the electrical circuits 2900, 2900' are similar in all respects except that each circuit 2900, 2900' includes a different number of, and a different placement of, 0Ω jumper resistors 2904, 2904'. For each circuit, the presence of a 0Ω jumper resistor 2904, 2904' is necessary when one physical wire is to cross over another. In addition, the number and placement of the 0Ω jumper resistors 2904, 2904' differ in each circuit 2900, 2900', because the physical layout and orientation of the circuits 2900, 2900' differ in the left and rights shoes. Other than the different number and placement of the 0Ω jumper resistors 2904, 2904' in the left and right shoes, however, the electrical connections in the two circuits 2900, 2900' are the same. Accordingly, only the electrical circuit 2900 that is suitable for implementing the intelligent system 106 in a wearer's left shoe is discussed below.

With reference to FIG. 35, the electrical circuit 2900 includes a power source 2906, a voltage regulator system 2908, a sensing system 2912, a control system 2916, and an actuation system 2920. In the embodiment illustrated, the power source 2906 is a 3.0 V battery and the voltage regulator system 2908 is a step-up DC-DC voltage regulator system that employs the MAX1724 step-up DC/DC converter manufactured by Maxim Integrated Products of Sunnyvale, Calif. The 3.0 V input voltage of the power source 2906 is stepped-up to a higher 5.0 V output voltage at the output 2924 of the MAX1724 step-up DC/DC converter. It should be understood, however, that other types of power sources and voltage regulator systems may be used in the electrical circuit 2900.

The sensing system 2912 includes a sensor 2928 (e.g., a linear ratiometric hall effect sensor) and a switch 2932. The control system 2916 includes a microcontroller 2936 (e.g., the PIC16F88 microcontroller manufactured by Microchip Technology, Inc. of Chandler, Ariz.), five electro-luminescent elements 2940 (e.g., light emitting diodes), and two switches 2944, 2948.

The 5.0 V output 2924 of the voltage regulator system 2908 is connected to pins 15 and 16 of the microcontroller 2936 in order to power the microcontroller 2936. Pins 5 and 6 of the microcontroller 2936 are connected to ground to provide the microcontroller 2936 with a ground reference. A reference voltage of approximately 1.0 V is provided to pin 1 of the microcontroller 2936; however, this reference voltage may be varied by choosing appropriate values for resistors 2952 and 2956, which together form a voltage divider. Similarly, a reference voltage of approximately 3.0 V is provided to pin 2 of the microcontroller 2936, but this reference voltage may be varied by choosing appropriate values for resistors 2960 and 2964, which together form a voltage divider.

The sensor 2928 measures the strength of the magnetic field present in the sole 104 of the article of footwear 100 and outputs at terminal 2968 an analog voltage representative of the strength of the magnetic field. Typically, the analog voltage output by the sensor 2928 is between about 1.0 V and about 2.5 V. In one embodiment, the sensor 2928 outputs smaller voltages for stronger magnetic fields and, accordingly, for greater amounts of compression in the sole 104. The analog voltage output by the sensor 2928 is received at pin 3 of the microcontroller 2936, is compared by the microcontroller 2936 to the reference voltages present at its pins 1 and 2, and is converted by the microcontroller to a digital value using an A/D converter. This digital value, which in one embodiment is smaller for stronger magnetic fields and, accordingly, for greater amounts of compression in the sole 104, is then used by the microcontroller 2936 to implement the method 2300 described above.

In one embodiment, the sensor 2928 is turned on to measure magnetic field strength, as described above, and then off to conserve power. Specifically, to turn on the sensor 2928, the microcontroller 2936 first outputs a low voltage from its pin 7. This in turn causes the switch 2932 to close, thereby connecting the 5.0 V output 2924 of the voltage regulator system 2908 to the sensor 2928 and powering the sensor 2928. To turn off the sensor 2928, the microcontroller 2936 outputs a high voltage from its pin 7. This in turn causes the switch 2932 to open, thereby disconnecting the 5.0 V output 2924 of the voltage regulator system 2908 from the sensor 2928 and turning off the sensor 2928. In one embodiment, the switch 2932 is a p-Channel MOSFET.

Similarly, to conserve power, the microcontroller 2936 may turn off the voltage reference implemented at its pins 1 and 2. To do so, the microcontroller 2936 outputs approximately 5.0 V at pin 9 thereof. To turn the voltage reference implemented at its pins 1 and 2 back on, the microcontroller outputs approximately 0 V at its pin 9.

The five electro-luminescent elements 2940 provide a visual output to the user. For example, the five electro-luminescent elements 2940 may be used to display the current hardness/softness setting of the sole 104. As illustrated in FIG. 35, pins 17, 18, and 19 of the microcontroller 2936 are connected, through resistors 2972, to the five electro-luminescent elements 2940. Based on the results obtained from implementing the method 2300 described above, the microcontroller 2936 controls the output/input at its pins 17, 18, and 19 to turn on or off one or several of the electro-luminescent elements 2940. The table in FIG. 37 illustrates the states of the input/output at pins 17, 18, and 19 of the microcontroller 2936 that are required to turn on several combinations of the electro-luminescent elements 2940. State "0" represents a low voltage output by the microcontroller 2936 at a particular pin; state "1" represents a high voltage output by the microcontroller 2936 at a particular pin; and state "Z" represents a high input impedance created by the microcontroller at a particular pin.

Switches 2944 and 2948 are connected between ground and pins 14 and 13, respectively, of the microcontroller 2936. As described above with respect to the method 2300, the user may close switch 2944 to connect pin 14 of the microcontroller 2936 to ground, while leaving the switch 2948 open, and thereby indicate his desire to change the hardness setting for the sole 104 to a harder setting. Similarly, the user may close switch 2948 to connect pin 13 of the microcontroller 2936 to ground, while leaving the switch 2944 open, and thereby indicate his desire to change the hardness setting for the sole 104 to a softer setting. If the user closes both switches 2944 and 2948 at the same time, the microcontroller 2936 calls the "OFF" sequence described above with respect to method 2300. The user may close either switch 2944 or 2948 by actuating push buttons, which are located on the outside of the article of footwear 100.

The actuation system 2920 includes transistor bridges 2976 and 2980, and a motor (not shown) connected in parallel with a capacitor 2984. In the embodiment illustrated in FIG. 35, the transistor bridge 2976 includes an n-Channel MOSFET (including gate G1, source S1, and drain D1) and a p-Channel MOSFET (including gate G2, source S2, and drain D2). The transistor bridge 2980 also includes an n-Channel MOSFET (including gate G1, source S1, and drain D1) and a p-Channel MOSFET (including gate G2, source S2, and drain D2). The source S1 of transistor bridge 2976 and the source S1 of transistor bridge 2980 are connected to ground. The source S2 of transistor bridge 2976 and the source S2 of transistor bridge 2980 are connected to the positive terminal of the power source 2906. The gate G1 of transistor bridge 2976 and the gate G2 of transistor bridge 2980 are connected to pin 12 of the microcontroller 2936. The gate G2 of transistor bridge 2976 and the gate G1 of transistor bridge 2980 are connected to pin 10 of the microcontroller 2936. The drain D1 of transistor bridge 2976 and the drain D2 of transistor bridge 2980 are connected to the motor drive return terminal 2988 of the motor. The drain D2 of the transistor bridge 2976 and the drain D1 of the transistor bridge 2980 are connected to the motor drive forward terminal 2992 of the motor.

As illustrated in the table of FIG. 38, in order to drive the motor forward, the microcontroller 2936 outputs a high voltage at its pin 12 and a low voltage at its pin 10. This turns on the MOSFETs of transistor bridge 2976 and turns off the MOSFETs of transistor bridge 2980. As a result, the motor drive forward terminal 2992 is connected to the positive terminal of the power source 2906 and the motor drive return terminal 2988 is connected to ground, driving the motor forward. In order to drive the motor backward, the microcontroller 2936 outputs a low voltage at its pin 12 and a high voltage at its pin 10. This turns off the MOSFETs of transistor bridge 2976 and turns on the MOSFETs of transistor bridge 2980. As a result, the motor drive forward terminal 2992 is connected to ground and the motor drive return terminal 2988 is connected to the positive terminal of the power source 2906, driving the motor backward. If the microcontroller 2936 outputs a high voltage at both its pin 10 and its pin 12, or a low voltage at both its pin 10 and its pin 12, the motor is stopped and remains idle.

The positive terminal of the power source 2906 is also connected to pin 20 of the microcontroller 2936. As such, the microcontroller 2936 can sense the voltage at the positive terminal of the power source (e.g., can sense a battery voltage) and can use the sensed voltage in performing the steps of the method 2300 described above. For example, as described above, the microcontroller 2936 can determine from the sensed voltage whether the motor is blocked and, if so, can stall the motor.

Pin 4 of the microcontroller 2936 is the active low reset pin of the microcontroller 2936. It allows the microcontroller 2936 to be reset during testing/debugging, but is not used when a wearer is walking/running in the article of footwear 100. Similarly, pins 8 and 11 of the microcontroller 2936 are used during testing/debugging, but are not used when the wearer is walking/running in the article of footwear 100. Specifically, pin 8 of the microcontroller 2936 is a data pin, which allows for the transfer of data, and pin 11 of the microcontroller 2936 is a clock pin.

In addition, the electrical circuit 2900 includes a plurality of test points 2996 (i.e., test points TP1 through TP10) that are used during testing/debugging and when the power source 2906 is disconnected from the circuit 2900, but that are not used when the wearer is walking/running in the article of footwear 100. For example, test point TP1 provides the microcontroller 2936 with a reference voltage of approximately 1.0 V; test point TP2 provides the microcontroller 2936 with a reference voltage of approximately 3.0 V; test point TP3 provides a simulated reading from the sensor 2928 to the microcontroller 2936; test point TP4 provides power to the microcontroller 2936; and test point TP5 provides the electrical circuit 2900 with a reference ground. Test point TP6 connects to the clock pin 11 of the microcontroller 2936 and test point TP9 allows the microcontroller 2936 to be reset. Test points TP7, TP8, and TP10 allow data to be transferred to and from the microcontroller 2936 during testing/debugging.

In one embodiment, for example, test points TP7 and TP8 may simulate the opening and closing of the switches 2948 and 2944, respectively, during testing/debugging.

Figure 39A:
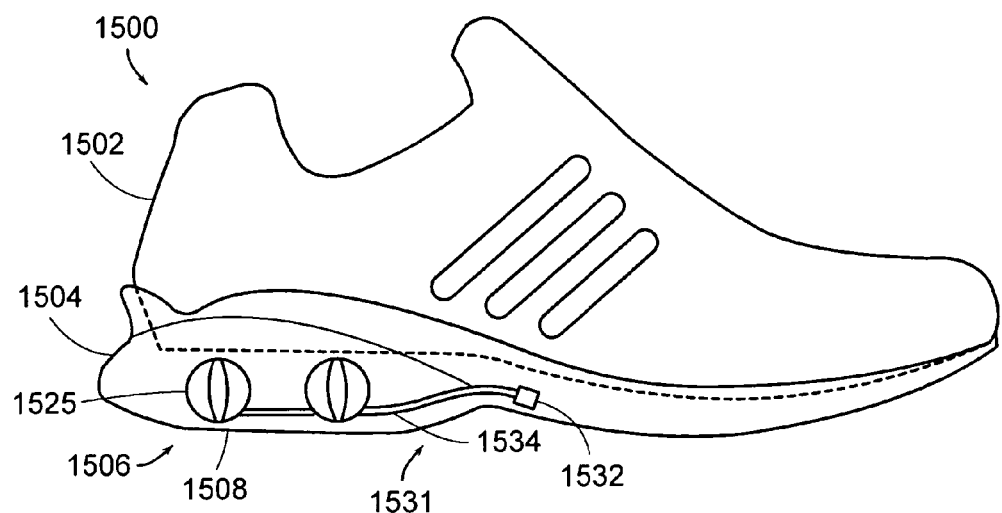
FIG. 39A is a schematic side view of an article of footwear including an alternative embodiment of an intelligent system in accordance with the invention.
Figure 39B:
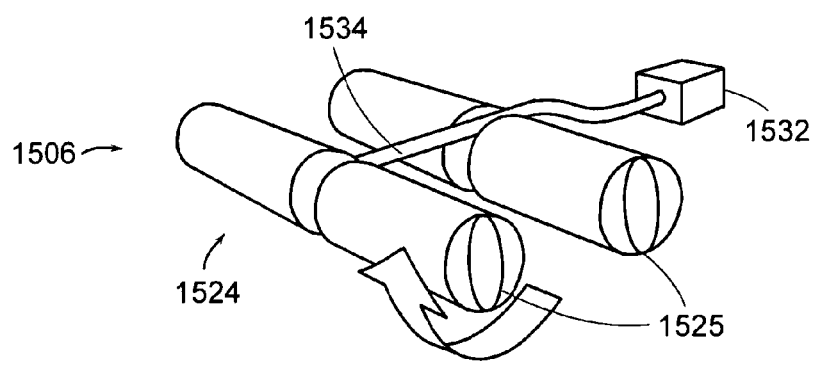
FIG. 39B is a schematic perspective view of a portion of the intelligent system of FIG. 39A.

FIGS. 39A and 39B depict an article of footwear 1500 including an alternative intelligent system 1506. The article of footwear 1500 includes an upper 1502, a sole 1504, and the intelligent system 1506. The intelligent system 1506 is disposed in the rearfoot portion 1508 of the sole 1504. The intelligent system 1506 includes a driver 1531 and an adjustable element 1524 of one or more similar components. The adjustable element 1524 is shown in greater detail in FIG. 39B and includes two dual density tuning rods 1525 that are rotated in response to a corrective driver signal to modify a performance characteristic of the footwear 1500. The dual density rods 1525 have an anisotropic property and are described in detail in U.S. Pat. No. 6,807,753, the entire disclosure of which is hereby incorporated herein by reference. The dual density rods 1525 are rotated by the motor 1532 and the transmission element 1534 to make the sole 1504 harder or softer. The transmission element 1534 is coupled to the dual density rods 1525 at about a lateral midpoint of the rods 1525, for example by a rack and pinion or worm and wheel arrangement.

FIG. 40A depicts an article of footwear 1600 including an alternative intelligent system 1606. FIGS. 40B-40D depict the adjustable element 1624 in various states of operation. The article of footwear 1600 includes an upper 1602, a sole 1604, and the intelligent system 1606. The intelligent system 1606 includes a driver 1631 and an adjustable element 1624. The adjustable element 1624 includes two multi-density plates 1625, 1627. One of the plates, in this embodiment lower plate 1627, is slid relative to the other plate, in this embodiment upper plate 1625, by the driver 1631, in response to the corrective driver signal to modify the performance characteristic of the shoe (arrow 1680).

The plates 1625, 1627 are made of alternating density materials. In particular, the plates 1625, 1627 are made up of alternating strips of a relatively soft material 1671 and a relatively hard material 1673. The alignment of the different density portions of the plates 1625, 1627 determines the performance characteristic of the shoe. In FIG. 40B, the relatively hard materials 1673 are substantially aligned, thereby resulting in a relatively hard adjustable element 1624. In FIG. 40C, the different density materials 1671, 1673 are only partially aligned, thereby resulting in a softer adjustable element 1624. In FIG. 40D, the relatively hard materials 1673 and the relative soft materials 1671 are substantially aligned, thereby resulting in the softest possible adjustable element 1624.

Figure 41A:
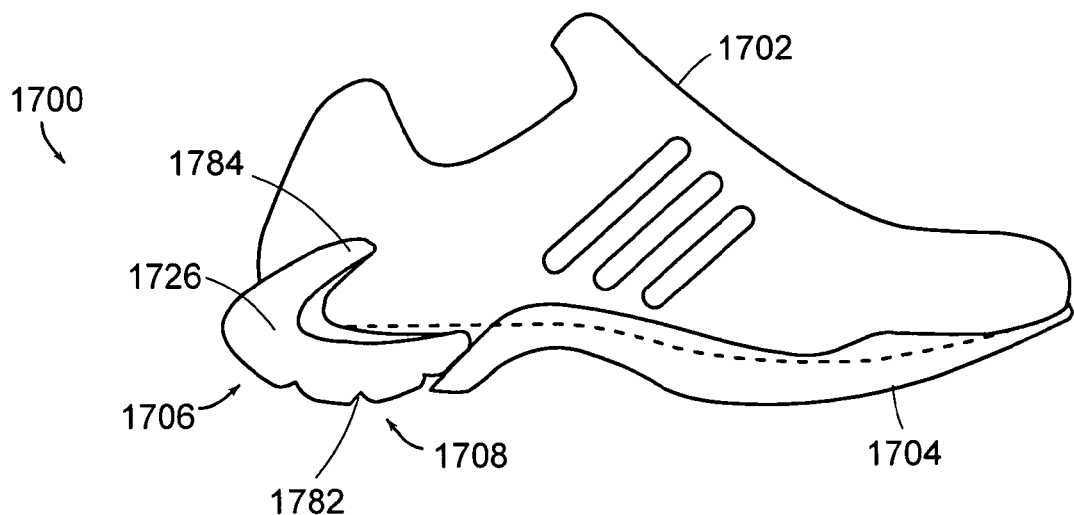
FIG. 41A is a schematic side view of an article of footwear including yet another alternative embodiment of an intelligent system in accordance with the invention.
Figure 41B:
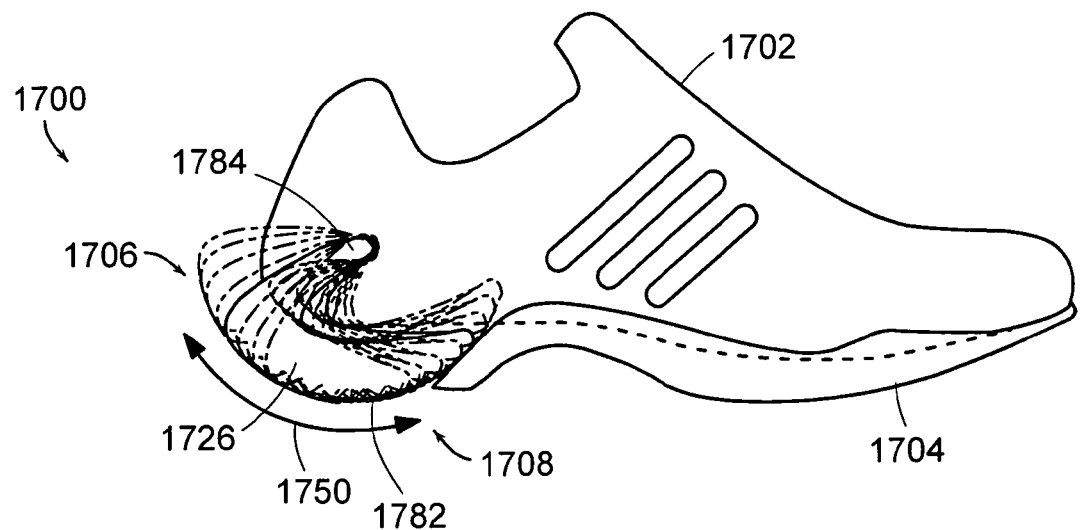
FIG. 41B is a schematic side view of the intelligent system of FIG. 41A throughout a range of adjustment.

FIGS. 41A and 41B depict an article of footwear 1700 including an alternative intelligent system 1706. The article of footwear 1700 includes an upper 1702, a sole 1704, and the intelligent system 1706. The intelligent system 1706 is disposed in the rearfoot portion 1708 of the sole 1704. The intelligent system 1706 includes a driver 1731 (not shown, but similar to those described hereinabove) and an adjustable element 1724. The adjustable element 1724 is a multi-density heel portion 1726 that swivels relative to the sole 1704 (see arrow 1750 in FIG. 41B). Swiveling the heel portion 1726 modifies the mechanical properties of the footwear 1700 at a heel strike zone 1782. The heel portion 1726 swivels about a pivot point 1784 in response to a force from the driver 1731.

The various components of the adjustable elements described herein can be manufactured by, for example, injection molding or extrusion and optionally a combination of subsequent machining operations. Extrusion processes may be used to provide a uniform shape, such as a single monolithic frame. Insert molding can then be used to provide the desired geometry of the open spaces, or the open spaces could be created in the desired locations by a subsequent machining operation. Other manufacturing techniques include melting or bonding additional elements. For example, the cylinders 448 may be joined with a liquid epoxy or a hot melt adhesive, such as EVA. In addition to adhesive bonding, components can be solvent bonded, which entails using a solvent to facilitate fusing of various components or fused together during a foaming process.

The various components can be manufactured from any suitable polymeric material or combination of polymeric materials, either with or without reinforcement. Suitable materials include: polyurethanes, such as a thermoplastic polyurethane (TPU); EVA; thermoplastic polyether block amides, such as the Pebax® brand sold by Elf Atochem; thermoplastic polyester elastomers, such as the Hytrel® brand sold by DuPont; thermoplastic elastomers, such as the Santoprene® brand sold by Advanced Elastomer Systems, L.P.; thermoplastic olefin; nylons, such as nylon 12, which may include 10 to 30 percent or more glass fiber reinforcement; silicones; polyethylenes; acetal; and equivalent materials. Reinforcement, if used, may be by inclusion of glass or carbon graphite fibers or para-aramid fibers, such as the Kevlar® brand sold by DuPont, or other similar method. Also, the polymeric materials may be used in combination with other materials, for example natural or synthetic rubber. Other suitable materials will be apparent to those skilled in the art.

In a particular embodiment, the expansion element 126 can be made of one or more various density foams, non-foamed polymer materials, and/or skeletal elements. For example, the cylinder could be made of Hytrel® 4069 or 5050 with a 45 Asker C foamed EVA core. In another embodiment, the cylinder is made of Hytrel® 5556 without an inner core foam. The expansion element 126 can have a hardness in the range of about 40 to about 70 Asker C, preferably between about 45 and about 65 Asker C, and more preferably about 55 Asker C. In an alternative embodiment, the tuning rods 1525, the multiple density plates 1625, 1627, or the upper and lower support plates 114, 116 may be coated with an anti-friction coating, such as a paint including Teflon® material sold by DuPont or a similar substance. The various components can be color coded to indicate to a wearer the specific performance characteristics of the system and clear windows can be provided along the edge of the sole. The size and shape of the various components can vary to suit a particular application. In one embodiment, the expansion element 126 can be about 10 mm to about 40 mm in diameter, preferably about 20 mm to about 30 mm, and more preferably about 25 mm. The length of the expansion element 126 can be about 50 mm to about 100 mm, preferably about 75 mm to about 90 mm, and more preferably 85 mm.

In addition, the expansion element 126 can be integrally formed by a process called reverse injection, in which the cylinder 142 itself forms the mold for the foam core 144. Such a process can be more economical than conventional manufacturing methods, because a separate core mold is not required. The expansion element 126 can also be formed in a single step called dual injection, where two or more materials of differing densities are injected simultaneously to create integrally the cylinder 142 and the core 144.

Figure 42:
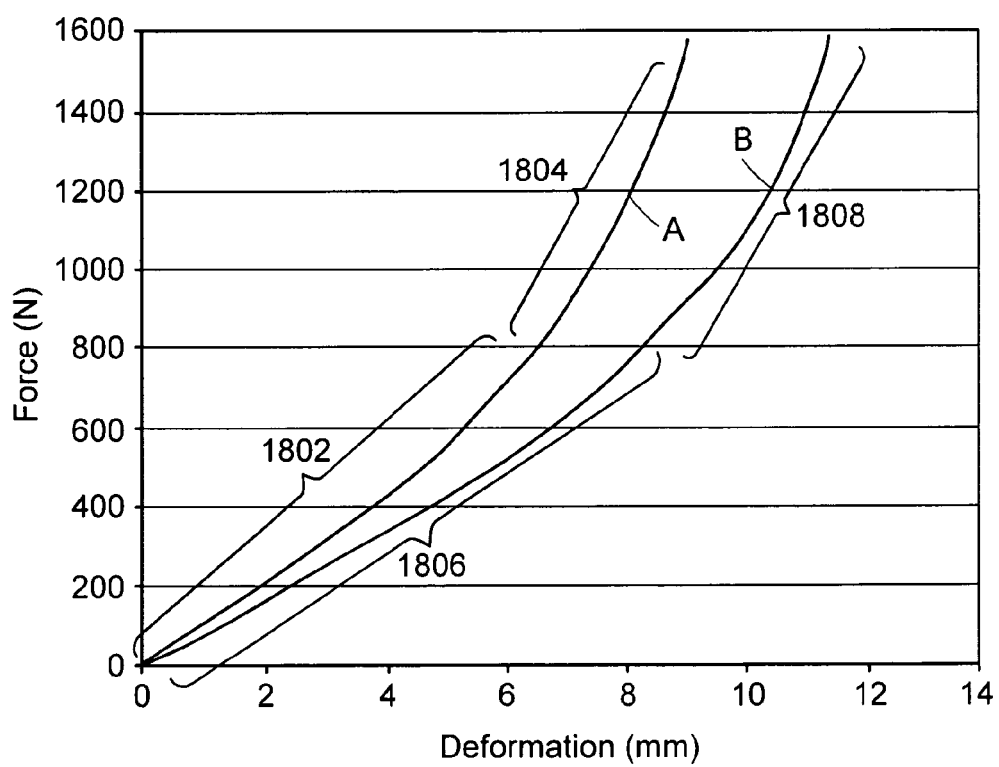
FIG. 42 is a graph depicting a performance characteristic of a specific embodiment of an adjustable element.

FIG. 42 is a graph depicting a performance characteristic of an adjustable element at two different settings (curves A and B). The graph depicts the amount of deformation of the adjustable element in a loaded condition, i.e., under compression. As can be seen, each curve A, B has two distinct slopes 1802, 1804, 1806, 1808. The first slope 1802, 1806 of each curve generally represents the adjustable element from first contact until the adjustable element contacts the limiter. During this phase, the resistance to compression comes from the combined effect of the structural wall and core of the adjustable element, which compress when loaded. The second slope 1804, 1808 of each curve represents the adjustable element under compression while in contact with the limiter. During this phase, very little additional deformation of the adjustable element is possible and the additional force attempts to bend or buckle the structural wall.

At setting A, which is a relatively hard setting, the adjustable element deforms about 6.5 mm when a force of 800 N is applied to the adjustable element, as represented by slope 1802. At this point, the adjustable element has contacted the limiter and very little additional deformation is possible. As slope 1804 represents, the additional deformation of the adjustable element is only about 2 mm after an additional force of 800 N is applied to the adjustable element. At setting B, which is a relatively soft setting, the adjustable element deforms about 8.5 mm when a force of 800 N is applied to the adjustable element, as represented by slope 1806. At this point, the adjustable element has contacted the limiter and very little additional deformation is possible. As slope 1808 represents, the additional deformation of the adjustable element is only about 2.5 mm after an additional force of 800 N is applied to the adjustable element.

Figure 43:
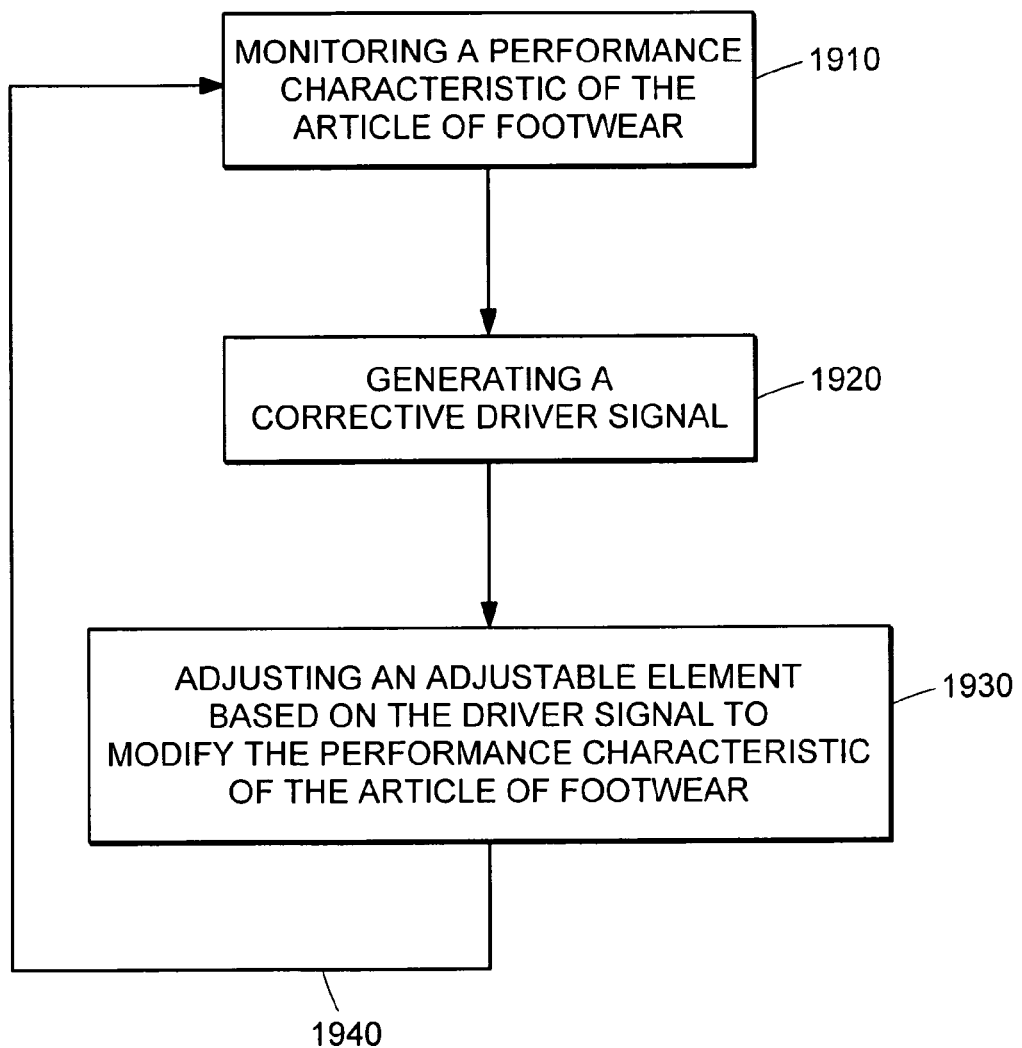
FIG. 43 is a flow chart depicting one embodiment of a method of modifying a performance characteristic of an article of footwear during use.

FIG. 43 depicts a flow chart representing a method of modifying a performance characteristic of an article of footwear during use. The method includes monitoring the performance characteristic of the article of footwear (step 1910), generating a corrective driver signal based on the monitored performance characteristic (step 1920), and adjusting an adjustable element based on the driver signal to modify the performance characteristic of the article of footwear (step 1930). In a particular embodiment, the steps are repeated until a threshold value of the performance characteristic is obtained (step 1940).

Figure 44A:
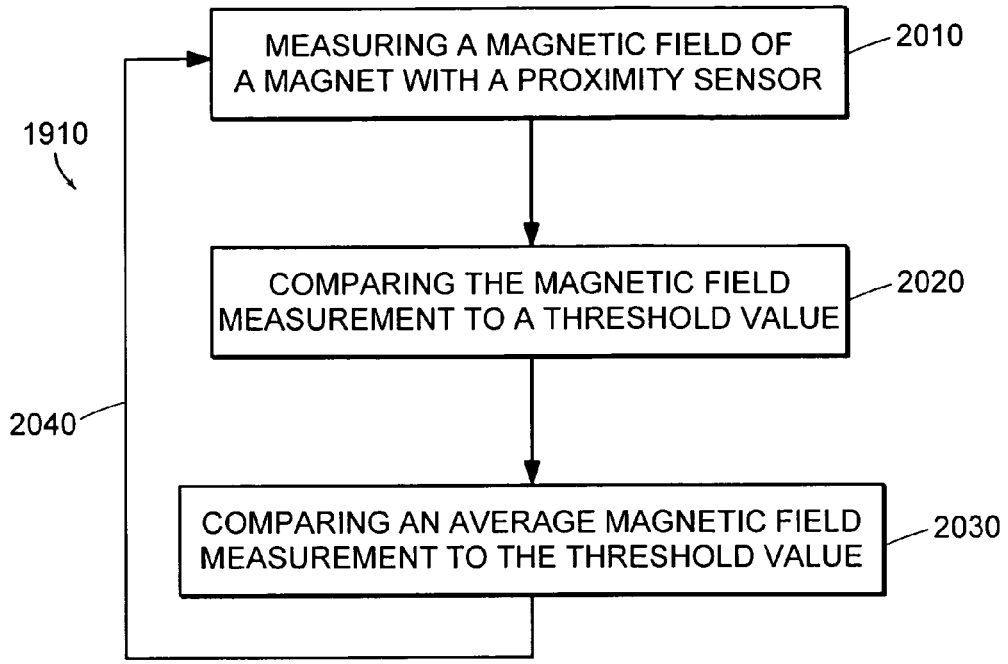
FIGS. 44A and 44B are flow charts depicting additional embodiments of the method of FIG. 43.

One possible embodiment of the monitoring step 1910 is expanded in FIG. 44A. As shown, monitoring the performance characteristic involves measuring a magnetic field of a magnet with a proximity-type sensor (substep 2010) and comparing the magnetic field measurement to a threshold value (substep 2020). Optionally, monitoring the performance characteristic may include taking multiple measurements of the magnetic field and taking an average of some number of measurements. The system then compares the average magnetic field measurement to the threshold value (optional substep 2030). The system could repeat these steps as necessary (optional substep 2040) until the magnetic field measurement is substantially equal to the threshold value, or within a predetermined value range.

Figure 44B:
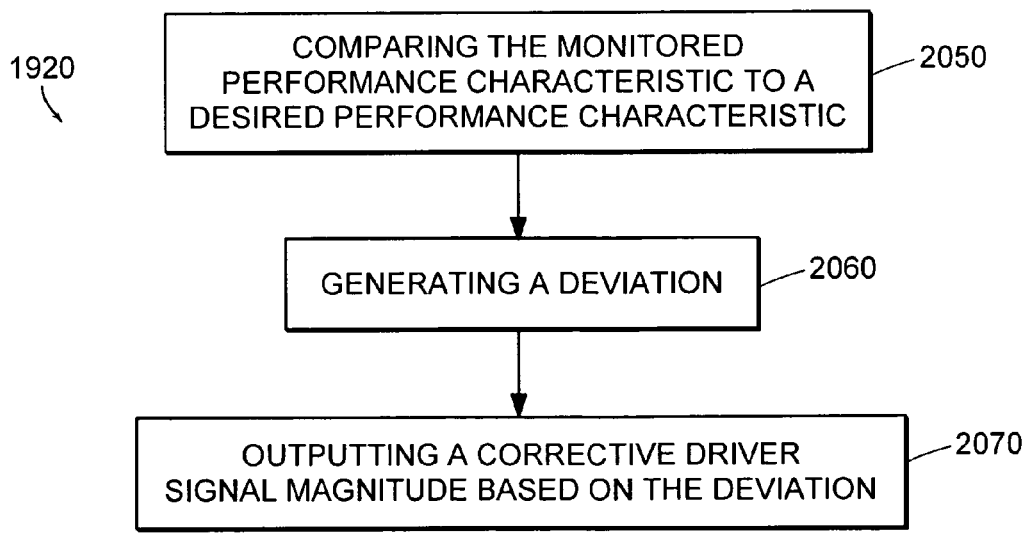

One possible embodiment of the generating step 1920 is expanded in FIG. 44B. As shown, generating the corrective driver signal involves comparing the monitored performance characteristic to a desired performance characteristic (substep 2050), generating a deviation (substep 2060), and outputting a corrective driver signal magnitude based on the deviation (substep 2070). In one embodiment, the corrective driver signal has a predetermined magnitude, such that a predetermined amount of correction is made to the performance characteristic. In this way, the system makes incremental changes to the performance characteristic that are relatively imperceptible to the wearer, thereby eliminating the need for the wearer to adapt to the changing performance characteristic.

Figure 45:
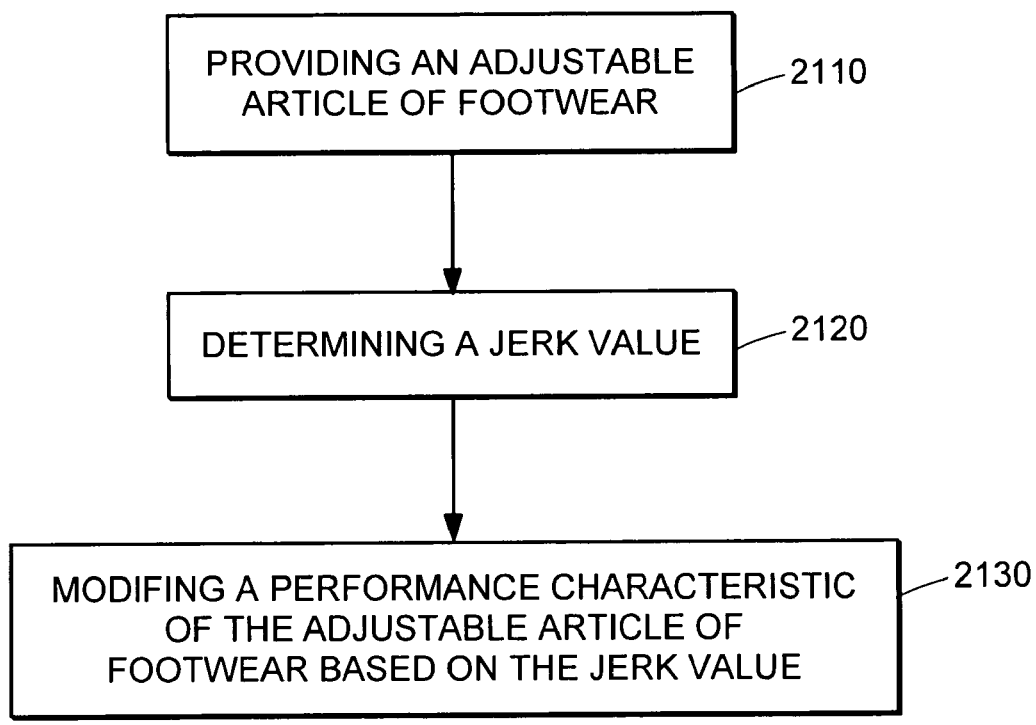
FIG. 45 is a flow chart depicting one embodiment of a method of providing comfort in an article of footwear.

FIG. 45 depicts a flow chart representing a method of providing comfort in an article of footwear. The method includes providing an adjustable article of footwear (step 2110) and determining a jerk value (step 2120). Jerk is represented as a change of acceleration over a change in time ($\Delta a/\Delta t$). The jerk value can be derived from the distance measurement, based on the changing magnetic field, over a known time period. A control system records the change in the magnetic field over time and is able to process these measurements to arrive at the jerk value. The method may further include modifying a performance characteristic of the adjustable article of footwear based on the jerk value (optional step 2130), for example, to keep the jerk value below a predetermined maximum value.

Having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. An intelligent footwear system comprising:
   an article of footwear;
   a system for monitoring a state of the article of footwear, the monitoring system at least partially disposed in the article of footwear, wherein the monitoring system comprises a sensor for tracking a state of the article of footwear and a transmitter for transmitting an electrical signal corresponding to the state of the article of footwear; and
   a device located remotely from the article of footwear and in communication with the monitoring system, wherein the device comprises a receiver to receive the electrical signal and a display to display information corresponding to the state of the article of footwear;
   wherein the state of the article of footwear corresponds to at least one mechanical property of the article of footwear selected from the group consisting of absolute compression, rate of compression, frequency of compression, change in rate of compression, uneven compression, time to peak compression, time to recovery, time of flight phase, time of stance phase, stability, stiffness, resiliency, compliancy, elasticity, damping, energy storage, cushioning, and comfort.

2. The intelligent footwear system of claim 1, wherein the sensor continuously tracks the state of the article of footwear.

3. The intelligent footwear system of claim 2, wherein the device continuously displays the information corresponding to the state of the article of footwear.

4. The intelligent footwear system of claim 1, wherein the sensor tracks performance of a wearer of the article of footwear.

5. The intelligent footwear system of claim 4, wherein the sensor continuously tracks the performance of the wearer of the article of footwear.

6. The intelligent footwear system of claim 4, wherein the transmitter transmits a second electrical signal corresponding to the performance of the wearer of the article of footwear and the device is configured to receive the second electrical signal and to display information corresponding to the performance.

7. The intelligent footwear system of claim 4, wherein the performance of the wearer of the article of footwear is selected from the group consisting of distance traveled, pace, and location.

8. The intelligent footwear system of claim 1 further comprising a processor disposed remotely from the article of footwear, the processor configured to analyze the information corresponding to the state of the article of footwear.

9. The intelligent footwear system of claim 8, wherein the device further comprises the processor.

10. The intelligent footwear system of claim 8, wherein information corresponding to an analysis of the state of the article of footwear by the processor is selected from the group consisting of stride frequency, change in speed, uphill motion, downhill motion, velocity, acceleration, and jerk.

11. An intelligent footwear system comprising:
an article of footwear;
a system for monitoring a state of the article of footwear, the monitoring system at least partially disposed in the article of footwear, wherein the monitoring system comprises:
    a sensor for tracking a state of the article of footwear;
    a processor for analyzing the state of the article of footwear and converting data corresponding to at least one of the state of the article of footwear and an analysis of the state of the article of footwear into an electrical signal; and
    a transmitter for transmitting the electrical signal; and
a device located remotely from the article of footwear and in communication with the monitoring system, wherein the device comprises a receiver to receive the electrical signal and a display to display at least one of information corresponding to the state of the article of footwear and information corresponding to the analysis of the state of the article of footwear;
wherein the state of the article of footwear corresponds to at least one mechanical property of the article of footwear selected from the group consisting of absolute compression, rate of compression, frequency of compression, change in rate of compression, uneven compression, time to peak compression, time to recovery, time of flight phase, time of stance phase, stability, stiffness, resiliency, compliancy, elasticity, damping, energy storage, cushioning, and comfort.

12. The intelligent footwear system of claim 11, wherein the sensor continuously tracks the state of the article of footwear.

13. The intelligent footwear system of claim 12, wherein the device continuously displays at least one of the information corresponding to the state of the article of footwear and the information corresponding to the analysis of the state of the article of footwear.

14. The intelligent footwear system of claim 11, wherein the information corresponding to the analysis of the state of the article of footwear is selected from the group consisting of stride frequency, change in speed, uphill motion, downhill motion, velocity, acceleration, and jerk.

15. The intelligent footwear system of claim 11, wherein the sensor tracks performance of a wearer of the article of footwear.

16. The intelligent footwear system of claim 15, wherein the sensor continuously tracks the performance of the wearer of the article of footwear.

17. The intelligent footwear system of claim 15, wherein the processor analyzes the performance of the wearer of the article of footwear, the transmitter transmits a second electrical signal corresponding to at least one of the performance of the wearer of the article of footwear and an analysis of the performance of the wearer of the article of footwear, and the device is configured to receive the second electrical signal and to display information corresponding to at least one of the performance of the wearer of the article of footwear and the analysis of the performance of the wearer of the article of footwear.

18. The intelligent footwear system of claim 15, wherein the performance of the wearer of the article of footwear is selected from the group consisting of distance traveled, pace, and location.

* * * * *